US012592370B2

(12) United States Patent
Larrouy-Maumus et al.

(10) Patent No.: US 12,592,370 B2
(45) Date of Patent: Mar. 31, 2026

(54) SCREENING WITH MASS SPECTROMETRY FOR MYCOBACTERIA PRIOR TO CARDIOTHORACIC SURGERY

(71) Applicant: IMPERIAL COLLEGE INNOVATIONS LIMITED, London (GB)

(72) Inventors: Gerald Larrouy-Maumus, London (GB); Francis Drobniewski, London (GB)

(73) Assignee: Imperial College Innovations Limited, London (GB)

( * ) Notice: Subject to any disclaimer, the term of this patent is extended or adjusted under 35 U.S.C. 154(b) by 926 days.

(21) Appl. No.: 17/766,194

(22) PCT Filed: Oct. 2, 2020

(86) PCT No.: PCT/GB2020/052442
§ 371 (c)(1),
(2) Date: Apr. 1, 2022

(87) PCT Pub. No.: WO2021/064426
PCT Pub. Date: Apr. 8, 2021

(65) Prior Publication Data
US 2023/0135821 A1 May 4, 2023

(30) Foreign Application Priority Data
Oct. 4, 2019 (GB) ...................................... 1914359

(51) Int. Cl.
*H01J 49/04* (2006.01)
*G01N 33/68* (2006.01)
*H01J 49/16* (2006.01)

(52) U.S. Cl.
CPC ...... *H01J 49/0418* (2013.01); *G01N 33/6851* (2013.01); *H01J 49/164* (2013.01)

(58) Field of Classification Search
None
See application file for complete search history.

(56) References Cited

U.S. PATENT DOCUMENTS

2008/0108104 A1  5/2008  Eckstein et al.

FOREIGN PATENT DOCUMENTS

WO  2012108839 A1  8/2012

OTHER PUBLICATIONS

Baker et al., Two-Phase Hospital-Associated Outbreak of *Mycobacterium abscessus*: Investigation and Mitigation, Clinical Infectious Diseases, pp. 902-911. (Year: 2017).*
(Continued)

*Primary Examiner* — Kathryn Elizabeth Limbaugh
(74) *Attorney, Agent, or Firm* — Christensen O'Connor Johnson Kindness PLLC

(57) ABSTRACT

The invention provides a method for identifying a subject suitable for receiving a lung transplant, the method comprising: subjecting a sample to mass spectrometry analysis (in the negative ion mode or positive ion mode; preferably in the positive ion mode) and generating a mass spectrum output; wherein said sample is an isolated sample obtained from a subject that is a candidate for receiving a lung transplant; detecting one or more peak set in said mass spectrum output; wherein the presence of said one or more peak set indicates that the subject is not a suitable candidate for receiving a lung transplant; or wherein the absence of said one or more peak set indicates that the subject is a suitable candidate for receiving a lung transplant. The invention relies on the detection of peak sets specific to the membrane of pathogens, in particular mycobacteria.

16 Claims, 21 Drawing Sheets

(56) References Cited

OTHER PUBLICATIONS

International Search Report and Written Opinion mailed Mar. 11, 2021, issued in corresponding International Application No. PCT/GB2020/052442, filed Oct. 2, 2020, 28 pages.

Stephenson, Dominic, et al. "An evaluation of methods for the isolation of nontuberculous mycobacteria from patients with cystic fibrosis, bronchiectasis and patients assessed for lung transplantation." BMC Pulmonary Medicine 19.19 (2019): 1-12.

Larrouy-Maumus, Gérald, and Germain Puzo. "Mycobacterial envelope lipids fingerprint from direct MALDI-TOF MS analysis of intact bacilli." Tuberculosis 95.1 (2015): 75-85.

Pranada, Arthur B., et al. "Accurate differentiation of *Mycobacterium chimaera* from *Mycobacterium intracellulare* by MALDI-TOF MS analysis." Journal of Medical Microbiology 66.5 (2017): 670-677.

Fangous, Marie-Sarah, et al. "Classification algorithm for subspecies identification within the *Mycobacterium abscessus* species, based on matrix-assisted laser desorption ionization-time of flight mass spectrometry." Journal of clinical microbiology 52.9 (2014): 3362-3369.

Gonzalo, Ximena, et al. "Performance of lipid fingerprint-based MALDI-ToF for the diagnosis of mycobacterial infections." Clinical Microbiology and Infection <https://doi.org/10.1016/j.cmi.2020.08.027> (2020), 5 pages.

Smibert, O., et al. "*Mycobacterium abscessus* complex-a particular challenge in the setting of lung transplantation." Expert review of anti-infective therapy 14.3 (2016): 325-333.

Search Report mailed Jun. 1, 2020, issued in GB Application No. 1914359.3, filed Oct. 4, 2019, 5 pages.

Song, Sang Hoon, et al. "Electrospray ionization-tandem mass spectrometry analysis of the mycolic acid profiles for the identification of common clinical isolates of mycobacterial species." Journal of microbiological methods 77.2 (2009): 165-177.

Sriram, Raghu, et al. "Matrix-assisted laser desorption ionization-time of flight mass spectrometry (MALDI-TOF MS) for rapid identification of *Mycobacterium abscessus*." Medical Journal Armed Forces India 74.1 (2018): 22-27.

European Examination and Search Report mailed Jul. 19, 2024, in corresponding European Patent Application No. 20788865.2, filed Feb. 10, 2020, 19 pages.

Camacho, L.R., et al., "Analysis of the Phthiocerol Dimycocerosate Locus of *Mycobacterium tuberculosis*," The Journal of Biological Chemistry 276(23):19845-19854, 2001.

Laval, F., et al., "Accurate Molecular Mass Determination of Mycolic Acids by MALDI-TOF Mass Spectrometry," Analytical Chemistry 73(18):4537-4544, 2001.

Lefmann, M., et al., "Novel Mass Spectrometry-Based Tool for Genotypic Identification of Mycobacteria," Journal of Clinical Microbiology 42(1):339-346, 2004.

Malaga, W., et al., "Deciphering the Genetic Bases of the Structural Diversity of Phenolic Glycolipids in Strains of the *Mycobacterium tuberculosis* Complex," The Journal of Biological Chemistry 283(22):15177-15184, 2008.

Sarkhel, R., et al., "Methionine sulfoxide reductase A of *Salmonella typhimurium* interacts with several proteins and abets in its colonization in the chicken," BBA—General Subjects 1861:3238-3245, 2017.

Wang, R., et al., "Fragmentation of lipopolysaccharide anchors in plasma desorption mass spectrometry," Journal of Microbiological Methods 15:151-166, 1992.

* cited by examiner

Mass (m/z)

Mass (m/z)

Mass (m/z)

Mass (m/z)

Mass (m/z)

Mass (m/z)

A

Mass (*m/z*)

B

C

SCREENING WITH MASS SPECTROMETRY FOR MYCOBACTERIA PRIOR TO CARDIOTHORACIC SURGERY

CROSS REFERENCE TO RELATED APPLICATIONS

This application is the U.S. national phase of PCT/GB2020/052442 filed on Oct. 2, 2020, which claims priority to United Kingdom Application No. 1914359.3 filed on Oct. 4, 2019, each expressly incorporated herein by reference in its entirety.

The present invention relates to methods for identifying candidates for receiving a lung transplant and/or screening equipment prior to cardiothoracic surgery.

Bacterial infections are associated with complications in a number of delicate medical procedures, particularly during surgery (e.g. open-heart surgery) and organ transplantation. Notably, the ability to detect an infection in lung transplant candidates is of vital importance, as any existing infection in a candidate can spread to and colonize the transplanted lung, significantly increasing the chance of organ rejection. Indeed, an existing infection is considered by many health authorities to be a contraindication to a lung transplant (and can thus be an automatic lung transplant disqualifier). Detection of the risk of bacterial infections following cardiothoracic surgery is now a high priority for the healthcare system (e.g. for Public Health England). Notably, extra measures are put in place prior to cardiothoracic surgery (e.g. open-heart surgery) to prevent infection, as infection of the heart (or its valves) with a bacterial pathogen can severely compromise the health of the patient.

Given the urgency of deciding whether or not to proceed with such procedures, there is a need for methods of rapidly identifying the suitability of a patient for undergoing these procedures. For example, a donated lung has a finite life span, and the decision of whether or not to provide a lung transplant to a particular patient must be made with urgency. Furthermore, the ability to identify the subject's suitability is of vital importance to their quality and/or length of life. There also exists a need for rapidly screening equipment prior to surgery.

The present invention solves one or more of the above-mentioned problems.

By identifying and exploiting the presence bespoke 'lipid fingerprints' (e.g. peak sets) specific to the membrane of these pathogens (pathogens which complicate transplant and surgical procedures), the present inventors have developed a rapid mass spectrometry based method of identifying the suitability of a subject for receiving a lung transplant and/or screening equipment for a contaminant. Advantageously, analysis may be performed directly on an impure/'crude' sample (e.g. without the need to purify lipids), thus simplifying and accelerating the analysis procedure. Furthermore, the inventors have elucidated bespoke 'lipid fingerprints' (e.g. peak sets) which are indicative of the suitability of a subject for receiving lung transplantation (or suitability of operating equipment for use during surgery). For example, an isolated sample from a subject may be subjected to MS analysis, leading to a rapid MS output, and the presence of absence of said peak set in this output (which correlates with the suitability to receive said procedure) allows for the decision of whether or not to proceed with a life-changing medical procedure.

Thus, in one aspect the invention provides a method for identifying a subject suitable for receiving a lung transplant, the method comprising:

a. subjecting a sample to mass spectrometry analysis (in the negative ion mode or positive ion mode; preferably in the positive ion mode) and generating a mass spectrum output; wherein said sample is an isolated sample obtained from a subject that is a candidate for receiving a lung transplant;

b. detecting one or more peak set in said mass spectrum output;

c. wherein the presence of said one or more peak set indicates that the subject is not a suitable candidate for receiving a lung transplant; and/or (preferably or)

d. wherein the absence of said one or more peak set indicates that the subject is a suitable candidate for receiving a lung transplant.

In another aspect, there is provided a method for screening operating theatre equipment for use in cardiothoracic surgery of a subject, the method comprising:

a. subjecting a sample to mass spectrometry analysis (in the negative ion mode or positive ion mode; preferably in the positive ion mode) and generating a mass spectrum output; wherein said sample is obtained from operating theatre equipment; and b. detecting one or more peak set in said mass spectrum output;

c. wherein the presence of said one or more peak set indicates that the operating theatre equipment is not suitable to be used during cardiothoracic surgery of a subject; and/or (preferably or)

d. wherein the absence of said one or more peak set indicates that the operating theatre equipment is suitable to be used during cardiothoracic surgery of a subject.

A further aspect of the invention provides a method for identifying the presence or absence of a bacterial infection in a subject subsequent to receiving cardiothoracic surgery, the method comprising:

a. subjecting a sample to mass spectrometry analysis (in the negative ion mode or positive ion mode; preferably in the positive ion mode) and generating a mass spectrum output; wherein said sample is an isolated sample obtained from a subject that has received cardiothoracic surgery; and b. detecting one or more peak set in said mass spectrum output;

c. wherein the presence of said one or more peak set is indicative of the presence of a bacterial infection in the subject subsequent to receiving cardiothoracic surgery; and/or (preferably or)

d. wherein the absence of said one or more peak set is indicative of the absence of a bacterial infection in a subject subsequent to receiving cardiothoracic surgery.

Another aspect of the invention provides a method for detecting the presence or absence of a *Mycobacterium* in a sample, the method comprising:

a. subjecting a sample to mass spectrometry analysis (in the negative ion mode or positive ion mode; preferably in the positive ion mode) and generating a mass spectrum output; and b. detecting one or more peak set in said mass spectrum output;

c. wherein the presence of said one or more peak set is indicative of the presence of a *Mycobacterium*; and/or (preferably or)

d. wherein the absence of said one or more peak set is indicative of the absence of a *Mycobacterium*.

The term "subject" may be used interchangeably with the term "patient" throughout.

The sample may be subjected to mass spectrometry in the positive ion mode, and said one or more peak set may be selected from:

i. a first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z);

ii. a second peak set comprising at least two, three, or four (preferably at least two) defined peaks selected from: a peak having a mass-to-charge ratio (m/z) of from 1220-1223 m/z (preferably about 1221.9 m/z), a peak having a m/z of from 1459-1462 m/z (preferably about 1460.2 m/z), a peak having a m/z of from 1739-1742 m/z (preferably about 1740.5 m/z), and a peak having a m/z of from 1741-1744 m/z (preferably about 1742.5);

iii. a third peak set comprising at least two, three, or four (preferably at least two) defined peaks selected from: a peak having a m/z of from 1242-1245 m/z (preferably about 1243.9 m/z), a peak having a m/z of from 1280-1283 m/z (preferably about 1281.9 m/z), a peak having a m/z of from 1294-1297 m/z (preferably about 1295.9 m/z), and a peak having a m/z of from 1923-1926 m/z (preferably about 1924.2 m/z);

iv. a fourth peak set comprising at least two, three, four, or five (preferably at least two) defined peaks selected from: a peak having a m/z of from 1012-1015 m/z (preferably about 1013.2 m/z), a peak having a m/z of from 1121-1124 m/z (preferably about 1122.8 m/z), a peak having a m/z of from 1122-1125 m/z (preferably about 1123.8 m/z), a peak having an m/z of from 1123-1126 m/z (preferably about 1124.8 m/z), and a peak having a m/z of from 1149-1152 m/z (preferably about 1150.9 m/z);

v. a fifth peak set comprising at least two, three, four, or five (preferably at least two) defined peaks selected from: a peak having a m/z of from 1311-1314 m/z (preferably about 1312.8 m/z), a peak having a m/z of from 1339-1342 m/z (preferably about 1340.8 m/z), a peak having a m/z of from 1474-1477 m/z (preferably about 1475.8 m/z), a peak having a m/z of from 1488-1491 m/z (preferably about 1489.8 m/z), and a peak having a m/z of from 1823-1826 m/z (preferably about 1824 m/z);

vi. a sixth peak pet comprising at least two, three, four, or five (preferably at least two) defined peaks selected from: a peak having a m/z of from 1242-1245 m/z (preferably about 1243.7 m/z), a peak having a m/z of from 1256-1259 m/z (preferably about 1257.8 m/z), a peak having a m/z of from 1270-1273 m/z (preferably about 1271.8 m/z), a peak having a m/z of from 1318-1321 m/z (preferably about 1319.8 m/z), and a peak having a m/z of from 1346-1349 m/z (preferably about 1347.8 m/z);

vii. a seventh peak set comprising at least two, three, or four (preferably at least two) defined peaks selected from: a peak having a m/z of from 1294-1297 m/z (preferably about 1295.9 m/z), a peak having a m/z of from 1296-1299 m/z (preferably about 1297.9 m/z), a peak having a m/z of from 1308-1311 m/z (preferably about 1309.9 m/z), and a peak having a m/z of from 1322-1325 m/z (preferably about 1323.9 m/z);

viii. an eighth peak set comprising at least two defined peaks selected from: a peak having a m/z of from 1370-1373 m/z (preferably about 1371 m/z), and a peak having a m/z of from 1412-1415 m/z (preferably about 1413 m/z);

ix. a ninth peak set comprising at least two, three, or four (preferably at least two) defined peaks selected from: a peak having a m/z of from 2129-2132 m/z (preferably about 2130.4 m/z), a peak having a m/z of from 2171-2174 m/z (preferably about 2172.4 m/z), a peak having a m/z of from 2247-2250 m/z (preferably about 2248.5 m/z), and a peak having a m/z of from 2261-2264 m/z (preferably about 2262.5 m/z);

x. a tenth peak set comprising at least two, three, or four (preferably at least two) defined peaks selected from: a peak having a m/z of from 2273-2276 m/z (preferably about 2274.1 m/z), a peak having a m/z of from 2275-2278 m/z (preferably about 2276.1 m/z), a peak having a m/z of from 2551-2554 m/z (preferably about 2552.2 m/z), and a peak having a m/z of from 2553-2556 m/z (preferably about 2554.2 m/z);

xi. an eleventh peak set comprising at least two, three, or four (preferably at least two) defined peaks selected from: a peak having a m/z of from 1339-1342 m/z (preferably about 1340.8 m/z), a peak having a m/z of from 1353-1356 m/z (preferably about 1354.8 m/z), a peak having a m/z of from 1367-1370 m/z (preferably about 1368.8 m/z), and a peak having an m/z of from 1381-1384 m/z (preferably about 1382.8 m/z);

xii. a twelfth peak set comprising at least two, three, or four (preferably at least two) defined peaks selected from: a peak having an m/z of from 1242-1245 m/z (preferably about 1243.7 m/z), a peak having an m/z of from 1256-1259 m/z (preferably about 1257.7 m/z), a peak having an m/z of from 1270-1273 m/z (preferably about 1271.7 m/z), and a peak having an m/z of from 1298-1301 m/z (preferably about 1299.7 m/z);

xiii. a thirteenth peak set comprising at least two, three, or four (preferably at least two) defined peaks selected from: a peak having an m/z of from 1458-1461 m/z (preferably about 1459.9 m/z), a peak having an m/z of from 2718-2721 m/z (preferably about 2719.6 m/z), a peak having an m/z of from 2760-2763 m/z (preferably about 2761.6 m/z), and a peak having an m/z of from 2788-2791 m/z (preferably about 2789.7 m/z);

xiv. a fourteenth peak set comprising at least two, three, four, or five (preferably at least two) defined peaks selected from: a peak having an m/z of from 1172-1175 m/z (preferably about 1173.9 m/z), a peak having an m/z of from 1174-1177 m/z (preferably about 1175.9 m/z), a peak having an m/z of from 1883-1886 m/z (preferably about 1884.2 m/z), a peak having an m/z of from 1909-1912 m/z (preferably about 1910.2 m/z), and a peak having an m/z of from 1911-1914 m/z (preferably about 1912.2 m/z);

xv. a fifteenth peak set comprising at least two, three, or four (preferably at least two) defined peaks selected from: a peak having an m/z of from 1202-1205 m/z (preferably about 1203.6 m/z), a peak having an m/z of from 1224-1227 m/z (preferably about 1225.6 m/z), a peak having an m/z of from 1226-1229 m/z (preferably about 1227.6 m/z), and a peak having an m/z of from 1240-1243 m/z (preferably about 1241.6 m/z);

xvi. a sixteenth peak set comprising at least two, three, four, or five (preferably at least two) defined peaks selected from: a peak having an m/z of from 1318-1321 m/z (preferably about 1319.9 m/z), a peak having an m/z of from 1332-1335 m/z (preferably about 1333.9 m/z), a peak having an m/z of from 1346-1349 m/z (preferably about 1347.9 m/z), a peak having an m/z of from 1360-1363 m/z (preferably about 1361.9 m/z), and a peak having an m/z of from 1374-1377 m/z (preferably about 1375.9 m/z);

xvii. a seventeenth peak set comprising at least two, three, or four (preferably at least two) defined peaks selected from: a peak having an m/z of from 1308-1311 m/z (preferably about 1309.9 m/z), a peak having an m/z of from 1310-1313 m/z (preferably about 1311.9 m/z), a peak having an m/z of from 1324-1327 m/z (preferably about 1325.9 m/z), and a peak having an m/z of from 1338-1341 m/z (preferably about 1339.9 m/z);

xviii. an eighteenth peak set comprising at least two, three, or four (preferably at least two) defined peaks selected from: a peak having an m/z of from 1012-1015 m/z (preferably about 1013.3 m/z), a peak having an m/z of from 1028-1031 m/z (preferably about 1029.3 m/z), a peak having an m/z of from 1697-1700 m/z (preferably about 1698.2 m/z), and a peak having an m/z of from 1698-1701 m/z (preferably about 1699.2 m/z);

xix. a nineteenth peak set comprising at least two defined peaks selected from: a peak having an m/z of from 1226-1229 m/z (preferably about 1227.9 m/z), and a peak having an m/z of from 1240-1243 m/z (preferably about 1241.9 m/z);

xx. a twentieth peak set comprising at least two, three, four, or five (preferably at least two) defined peaks selected from: a peak having an m/z of from 1414-1417 m/z (preferably about 1416 m/z), a peak having an m/z of from 1443-1446 m/z (preferably about 1444 m/z), a peak having an m/z of from 1445-1448 m/z (preferably about 1446 m/z), a peak having an m/z of from 1515-1518 m/z (preferably about 1516 m/z), and a peak having an m/z of from 1543-1546 m/z (preferably about 1544 m/z);

xxi. a twenty-first peak set comprising at least two, three, four, or five (preferably at least two) defined peaks selected from: a peak having an m/z of from 1036-1039 m/z (preferably about 1037.5 m/z), a peak having an m/z of from 1259-1262 m/z (preferably about 1260.3 m/z), a peak having an m/z of from 1374-1377 m/z (preferably about 1375.7 m/z), a peak having an m/z of from 2497-2500 m/z (preferably about 2498.7 m/z), and a peak having an m/z of from 2835-2838 m/z (preferably about 2837 m/z);

xxii. a twenty-second peak set comprising at least two, three, or four (preferably at least two) defined peaks selected from: a peak having an m/z of from 1057-1060 m/z (preferably about 1058.6 m/z), a peak having an m/z of from 1498-1501 m/z (preferably about 1499.7 m/z), a peak having an m/z of from 1512-1515 m/z (preferably about 1513.7 m/z), and a peak having an m/z of from 1526-1529 m/z (preferably about 1527.7 m/z);

xxiii. a twenty-third peak set comprising at least two, three, or four (preferably at least two) defined peaks selected from: a peak having an m/z of from 1432-1435 m/z (preferably about 1433.7 m/z), a peak having an m/z of from 1446-1449 m/z (preferably about 1447.7 m/z), a peak having an m/z of from 1460-1463 m/z (preferably about 1461.7 m/z), and a peak having an m/z of from 1474-1477 m/z (preferably about 1475.7 m/z);

xxiv. a twenty-fourth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.7 m/z), a peak having an m/z of from 1270-1273 m/z (preferably about 1271.7 m/z), and a peak having an m/z of from 1284-1287 m/z (preferably about 1285.7 m/z); and xxv. a twenty-fifth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.6 m/z), a peak having an m/z of from 1270-1273 m/z (preferably about 1271.7), and a peak having an m/z of from 1284-1287 m/z (preferably about 1285.7).

In a preferable embodiment, said one or more peak set is said first peak set [e.g. comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z)]. In a preferable embodiment, said first peak set comprises at least two, or three (preferably at least two) defined peaks selected from: a peak having a m/z of from 1256-1259 m/z (preferably about 1257.8 m/z), a peak having a m/z of from 1284-1287 m/z (preferably about 1285.9 m/z), and a peak having a m/z of from 1402-1405 m/z (preferably about 1403.9 m/z).

In one embodiment, said one or more peak set is said first peak set [for example, comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z)]; and the method may further comprise detecting the absence of one or more further defined peak(s) in said mass spectrum output, wherein said one or more defined peak(s) is selected from a peak having a m/z of from 1072-1075 m/z (preferably about 1073.6 m/z), a peak having a m/z of from 1248-1251 m/z (preferably about 1249.9 m/z), a peak having a m/z of from 1260-1263 m/z (preferably about 1261.9 m/z), a peak having a m/z of from 1262-1265 m/z (preferably about 1263.9 m/z), a peak having a m/z of from 1274-1277 m/z (preferably about 1275.9 m/z), a peak having a m/z of from 1276-1279 m/z (preferably about 1277.9 m/z), a peak having a m/z of from 1288-1291 m/z (preferably about 1289.9 m/z), a peak having a m/z of from 1290-1293 m/z (preferably about 1291.9 m/z), a peak having a m/z of from 1294-1297 m/z (preferably about 1295.9 m/z), a peak having a m/z of from 1304-1307 m/z (preferably about 1305.9 m/z), a peak having a m/z of from 1308-1311 m/z (preferably about 1309.9 m/z), a peak having a m/z of from 1310-1313 m/z (preferably about 1311.9 m/z), a peak having a m/z of from 1314-1317 m/z (preferably about 1315.9 m/z), a peak having a m/z of from 1318-1321 m/z (preferably about 1319.9 m/z), a peak having a m/z of from 1320-1323 m/z (preferably about 1321.9 m/z), a peak having a m/z of from 1322-1325 m/z (preferably about 1323.9 m/z), a peak having a m/z of from 1324-1327 m/z (preferably about 1325.9 m/z), a peak having a m/z of from 1332-1335 m/z (preferably about 1333.9 m/z), a peak having a m/z of from 1336-1339 m/z (preferably about 1337.9 m/z), a peak having a m/z of from 1338-1341 m/z (preferably about 1339.9 m/z), a peak having a m/z of from 1719-1722 m/z (preferably about 1720.1 m/z), a peak having a m/z of from 1735-1738 m/z (preferably about 1736.1 m/z), a peak having a m/z of from 1747-1750 m/z (preferably about 1748.1 m/z), a peak having a m/z of from 1761-1764 m/z (preferably about 1762.1 m/z), a peak having a m/z of from 1764-1767 m/z (preferably about 1765.1 m/z), and a peak having a m/z of from 1789-1792 m/z (preferably about 1790.1 m/z). Said reference to "one or more further defined peak(s)" may mean two or more further defined peak(s), three or more further defined peak(s), four or more further defined peak(s), five or more further defined peak(s), or may mean all of said further defined peaks.

In one embodiment, said one or more peak set is said first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z); and the method may further comprise detecting the absence of one or more further defined peak(s) in said mass spectrum output, wherein said one or more defined peak(s) is selected from a peak having a m/z of from 1072-1075 m/z (preferably about 1073.6 m/z), a peak having a m/z of from 1248-1251 m/z (preferably about 1249.9 m/z), a peak having a m/z of from 1260-1263 m/z (preferably about 1261.9 m/z), a peak having a m/z of from 1262-1265 m/z (preferably about 1263.9 m/z), a peak having a m/z of from 1274-1277 m/z (preferably about 1275.9 m/z), a peak having a m/z of from 1276-1279 m/z (preferably about 1277.9 m/z), a peak having a m/z of from 1288-1291 m/z (preferably about 1289.9 m/z), a peak having a m/z of from 1290-1293 m/z (preferably about 1291.9 m/z), a peak having a m/z of from 1294-1297 m/z (preferably about 1295.9 m/z), a peak having a m/z of from 1304-1307 m/z (preferably about 1305.9 m/z), a peak having a m/z of from 1308-1311 m/z (preferably about 1309.9 m/z), a peak having a m/z of from 1310-1313 m/z (preferably about 1311.9 m/z), a peak having a m/z of from 1314-1317 m/z (preferably about 1315.9 m/z), a peak having a m/z of from 1318-1321 m/z (preferably about 1319.9 m/z), a peak having a m/z of from 1320-1323 m/z (preferably about 1321.9 m/z), a peak having a m/z of from 1322-1325 m/z (preferably about 1323.9 m/z), a peak having a m/z of from 1324-1327 m/z (preferably about 1325.9 m/z), a peak having a m/z of from 1332-1335 m/z (preferably about 1333.9 m/z), a peak having a m/z of from 1336-1339 m/z (preferably about 1337.9 m/z), and a peak having a m/z of from 1338-1341 m/z (preferably about 1339.9 m/z). Said reference to "one or more further defined peak(s)" may mean two or more further defined peak(s), three or more further defined peak(s), four or more further defined peak(s), five or more further defined peak(s), or may mean all of said further defined peaks.

In one embodiment, said one or more peak set is said first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z); and the method may further comprise detecting the absence of one or more further defined peak(s) in said mass spectrum output, wherein said one or more defined peak(s) is selected from a peak having a m/z of from 1072-1075 m/z (preferably about 1073.6 m/z), a peak having a m/z of from 1248-1251 m/z (preferably about 1249.9 m/z), a peak having a m/z of from 1262-1265 m/z (preferably about 1263.9 m/z), a peak having a m/z of from 1308-1311 m/z (preferably about 1309.9 m/z), a peak having a m/z of from 1320-1323 m/z (preferably about 1321.9 m/z), a peak having a m/z of from 1719-1722 m/z (preferably about 1720.1 m/z), a peak having a m/z of from 1735-1738 m/z (preferably about 1736.1 m/z), a peak having a m/z of from 1747-1750 m/z (preferably about 1748.1 m/z), a peak having a m/z of from 1761-1764 m/z (preferably about 1762.1 m/z), a peak having a m/z of from 1764-1767 m/z (preferably about 1765.1 m/z), and a peak having a m/z of from 1789-1792 m/z (preferably about 1790.1 m/z).

In one embodiment, said one or more peak set is said first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z); and the method may further comprise detecting the absence of one or more further defined peak(s) in said mass spectrum output, wherein said one or more defined peak(s) is selected from a peak having a m/z of from 1072-1075 m/z (preferably about 1073.6 m/z), a peak having a m/z of from 1248-1251 m/z (preferably about 1249.9 m/z), a peak having a m/z of from 1262-1265 m/z (preferably about 1263.9 m/z), a peak having a m/z of from 1308-1311 m/z (preferably about 1309.9 m/z), and a peak having a m/z of from 1320-1323 m/z (preferably about 1321.9 m/z).

In one embodiment, said one or more peak set is said first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z); and the method may further comprise detecting the presence of one or more further defined peak(s) in said mass spectrum output, wherein said one or more defined peak(s) is selected from a peak having a m/z of from 1210-1213 m/z (preferably about 1211.8 m/z), a peak having a m/z of from 1398-1401 m/z (preferably about 1399.9 m/z), a peak having a m/z of from 1400-1403 m/z (preferably about 1401.9 m/z), a peak having a m/z of from 1412-1415 m/z (preferably about 1413.9 m/z), a peak having a m/z of from 1414-1417 m/z (preferably about 1415.9 m/z), a peak having a m/z of from 1426-1429 m/z (preferably about 1427.9 m/z), a peak having a m/z of from 1428-1431 m/z (preferably about 1429.9 m/z), a peak having a m/z of from 1442-1445 m/z (preferably about 1443.9 m/z), a peak having a m/z of from 1444-1447 m/z (preferably about 1445.9 m/z), a peak having a m/z of from 1456-1459 m/z (preferably about 1457.9 m/z), a peak having a m/z of from 1458-1461 m/z (preferably about 1459.9 m/z), and a peak having a m/z of from 1472-1475 m/z (preferably about 1474 m/z). Said reference to "one or more further defined peak(s)" may mean two or more further defined peak(s), three or more further defined peak(s), four or more further defined peak(s), five or more further defined peak(s), or may mean all of said further defined peaks.

Throughout the present disclosure, a peak may preferably be considered "absent" (in the mass spectrum output) when the peak has an intensity that is less than about 10% relative to the intensity of the most intense peak (e.g. corresponding to the most abundant analyte) in the mass spectrum output. In such cases, the peak may have an intensity below a threshold for the peak to be considered "present" in the mass spectrum output. Thus, for example, a peak (e.g. with a relative intensity of <10%) may be present in the mass spectrum output, but considered "absent" for failure to display an intensity above a threshold.

Similarly, throughout the present disclosure, a peak may preferably be considered "present" (in the mass spectrum output) when the peak has an intensity that is at least about 10% relative to the intensity of the most intense peak (e.g. corresponding to the most abundant analyte) in the mass spectrum output. In such cases, the peak may have an intensity above a threshold for the peak to be considered "present" in the mass spectrum output.

Thus, in one aspect the invention provides a method for identifying a subject suitable for receiving a lung transplant, the method comprising:

a. subjecting a sample to mass spectrometry analysis in the positive ion mode and generating a mass spectrum output; wherein said sample is an isolated sample obtained from a subject that is a candidate for receiving a lung transplant;

b. detecting one or more peak set in said mass spectrum output;

c. wherein said one or more peak set is selected from:

i. a first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z);

ii. a second peak set comprising at least two, three, or four (preferably at least two) defined peaks selected from: a peak having a mass-to-charge ratio (m/z) of from 1220-1223 m/z (preferably about 1221.9 m/z), a peak having a m/z of from 1459-1462 m/z (preferably about 1460.2 m/z), a peak having a m/z of from 1739-1742 m/z (preferably about 1740.5 m/z), and a peak having a m/z of from 1741-1744 m/z (preferably about 1742.5);

iii. a third peak set comprising at least two, three, or four (preferably at least two) defined peaks selected from: a peak having a m/z of from 1242-1245 m/z (preferably about 1243.9 m/z), a peak having a m/z of from 1280-1283 m/z (preferably about 1281.9 m/z), a peak having a m/z of from 1294-1297 m/z (preferably about 1295.9 m/z), and a peak having a m/z of from 1923-1926 m/z (preferably about 1924.2 m/z);

iv. a fourth peak set comprising at least two, three, four, or five (preferably at least two) defined peaks selected from: a peak having a m/z of from 1012-1015 m/z (preferably about 1013.2 m/z), a peak having a m/z of from 1121-1124 m/z (preferably about 1122.8 m/z), a peak having a m/z of from 1122-1125 m/z (preferably about 1123.8 m/z), a peak having an m/z of from 1123-1126 m/z (preferably about 1124.8 m/z), and a peak having a m/z of from 1149-1152 m/z (preferably about 1150.9 m/z);

v. a fifth peak set comprising at least two, three, four, or five (preferably at least two) defined peaks selected from: a peak having a m/z of from 1311-

1314 m/z (preferably about 1312.8 m/z), a peak having a m/z of from 1339-1342 m/z (preferably about 1340.8 m/z), a peak having a m/z of from 1474-1477 m/z (preferably about 1475.8 m/z), a peak having a m/z of from 1488-1491 m/z (preferably about 1489.8 m/z), and a peak having a m/z of from 1823-1826 m/z (preferably about 1824 m/z);

vi. a sixth peak pet comprising at least two, three, four, or five (preferably at least two) defined peaks selected from: a peak having a m/z of from 1242-1245 m/z (preferably about 1243.7 m/z), a peak having a m/z of from 1256-1259 m/z (preferably about 1257.8 m/z), a peak having a m/z of from 1270-1273 m/z (preferably about 1271.8 m/z), a peak having a m/z of from 1318-1321 m/z (preferably about 1319.8 m/z), and a peak having a m/z of from 1346-1349 m/z (preferably about 1347.8 m/z);

vii. a seventh peak set comprising at least two, three, or four (preferably at least two) defined peaks selected from: a peak having a m/z of from 1294-1297 m/z (preferably about 1295.9 m/z), a peak having a m/z of from 1296-1299 m/z (preferably about 1297.9 m/z), a peak having a m/z of from 1308-1311 m/z (preferably about 1309.9 m/z), and a peak having a m/z of from 1322-1325 m/z (preferably about 1323.9 m/z);

viii. an eighth peak set comprising at least two defined peaks selected from: a peak having a m/z of from 1370-1373 m/z (preferably about 1371 m/z), and a peak having a m/z of from 1412-1415 m/z (preferably about 1413 m/z);

ix. a ninth peak set comprising at least two, three, or four (preferably at least two) defined peaks selected from: a peak having a m/z of from 2129-2132 m/z (preferably about 2130.4 m/z), a peak having a m/z of from 2171-2174 m/z (preferably about 2172.4 m/z), a peak having a m/z of from 2247-2250 m/z (preferably about 2248.5 m/z), and a peak having a m/z of from 2261-2264 m/z (preferably about 2262.5 m/z);

x. a tenth peak set comprising at least two, three, or four (preferably at least two) defined peaks selected from: a peak having a m/z of from 2273-2276 m/z (preferably about 2274.1 m/z), a peak having a m/z of from 2275-2278 m/z (preferably about 2276.1 m/z), a peak having a m/z of from 2551-2554 m/z (preferably about 2552.2 m/z), and a peak having a m/z of from 2553-2556 m/z (preferably about 2554.2 m/z);

xi. an eleventh peak set comprising at least two, three, or four (preferably at least two) defined peaks selected from: a peak having a m/z of from 1339-1342 m/z (preferably about 1340.8 m/z), a peak having a m/z of from 1353-1356 m/z (preferably about 1354.8 m/z), a peak having a m/z of from 1367-1370 m/z (preferably about 1368.8 m/z), and a peak having an m/z of from 1381-1384 m/z (preferably about 1382.8 m/z);

xii. a twelfth peak set comprising at least two, three, or four (preferably at least two) defined peaks selected from: a peak having an m/z of from 1242-1245 m/z (preferably about 1243.7 m/z), a peak having an m/z of from 1256-1259 m/z (preferably about 1257.7 m/z), a peak having an m/z of from 1270-1273 m/z (preferably about 1271.7 m/z), and a peak having an m/z of from 1298-1301 m/z (preferably about 1299.7 m/z);

xiii. a thirteenth peak set comprising at least two, three, or four (preferably at least two) defined peaks selected from: a peak having an m/z of from 1458-1461 m/z (preferably about 1459.9 m/z), a peak having an m/z of from 2718-2721 m/z (preferably about 2719.6 m/z), a peak having an m/z of from 2760-2763 m/z (preferably about 2761.6 m/z), and a peak having an m/z of from 2788-2791 m/z (preferably about 2789.7 m/z);

xiv. a fourteenth peak set comprising at least two, three, four, or five (preferably at least two) defined peaks selected from: a peak having an m/z of from 1172-1175 m/z (preferably about 1173.9 m/z), a peak having an m/z of from 1174-1177 m/z (preferably about 1175.9 m/z), a peak having an m/z of from 1883-1886 m/z (preferably about 1884.2 m/z), a peak having an m/z of from 1909-1912 m/z (preferably about 1910.2 m/z), and a peak having an m/z of from 1911-1914 m/z (preferably about 1912.2 m/z);

xv. a fifteenth peak set comprising at least two, three, or four (preferably at least two) defined peaks selected from: a peak having an m/z of from 1202-1205 m/z (preferably about 1203.6 m/z), a peak having an m/z of from 1224-1227 m/z (preferably about 1225.6 m/z), a peak having an m/z of from 1226-1229 m/z (preferably about 1227.6 m/z), and a peak having an m/z of from 1240-1243 m/z (preferably about 1241.6 m/z);

xvi. a sixteenth peak set comprising at least two, three, four, or five (preferably at least two) defined peaks selected from: a peak having an m/z of from 1318-1321 m/z (preferably about 1319.9 m/z), a peak having an m/z of from 1332-1335 m/z (preferably about 1333.9 m/z), a peak having an m/z of from 1346-1349 m/z (preferably about 1347.9 m/z), a peak having an m/z of from 1360-1363 m/z (preferably about 1361.9 m/z), and a peak having an m/z of from 1374-1377 m/z (preferably about 1375.9 m/z);

xvii. a seventeenth peak set comprising at least two, three, or four (preferably at least two) defined peaks selected from: a peak having an m/z of from 1308-1311 m/z (preferably about 1309.9 m/z), a peak having an m/z of from 1310-1313 m/z (preferably about 1311.9 m/z), a peak having an m/z of from 1324-1327 m/z (preferably about 1325.9 m/z), and a peak having an m/z of from 1338-1341 m/z (preferably about 1339.9 m/z);

xviii. an eighteenth peak set comprising at least two, three, or four (preferably at least two) defined peaks selected from: a peak having an m/z of from 1012-1015 m/z (preferably about 1013.3 m/z), a peak having an m/z of from 1028-1031 m/z (preferably about 1029.3 m/z), a peak having an m/z of from 1697-1700 m/z (preferably about 1698.2 m/z), and a peak having an m/z of from 1698-1701 m/z (preferably about 1699.2 m/z);

xix. a nineteenth peak set comprising at least two defined peaks selected from: a peak having an m/z of from 1226-1229 m/z (preferably about 1227.9 m/z), and a peak having an m/z of from 1240-1243 m/z (preferably about 1241.9 m/z);

xx. a twentieth peak set comprising at least two, three, four, or five (preferably at least two) defined peaks selected from: a peak having an m/z of from 1414-1417 m/z (preferably about 1416 m/z), a peak having an m/z of from 1443-1446 m/z (preferably about 1444 m/z), a peak having an m/z of from 1445-1448 m/z (preferably about 1446 m/z), a peak having an m/z of from 1515-1518 m/z (preferably about 1516 m/z), and a peak having an m/z of from 1543-1546 m/z (preferably about 1544 m/z);

xxi. a twenty-first peak set comprising at least two, three, four, or five (preferably at least two) defined peaks selected from: a peak having an m/z of from 1036-1039 m/z (preferably about 1037.5 m/z), a peak having an m/z of from 1259-1262 m/z (preferably about 1260.3 m/z), a peak having an m/z of from 1374-1377 m/z (preferably about 1375.7 m/z), a peak having an m/z of from 2497-2500 m/z (preferably about 2498.7 m/z), and a peak having an m/z of from 2835-2838 m/z (preferably about 2837 m/z);

xxii. a twenty-second peak set comprising at least two, three, or four (preferably at least two) defined peaks selected from: a peak having an m/z of from 1057-1060 m/z (preferably about 1058.6 m/z), a peak having an m/z of from 1498-1501 m/z (preferably about 1499.7 m/z), a peak having an m/z of from 1512-1515 m/z (preferably about 1513.7 m/z), and a peak having an m/z of from 1526-1529 m/z (preferably about 1527.7 m/z);

xxiii. a twenty-third peak set comprising at least two, three, or four (preferably at least two) defined peaks selected from: a peak having an m/z of from 1432-1435 m/z (preferably about 1433.7 m/z), a peak having an m/z of from 1446-1449 m/z (preferably about 1447.7 m/z), a peak having an m/z of from 1460-1463 m/z (preferably about 1461.7 m/z), and a peak having an m/z of from 1474-1477 m/z (preferably about 1475.7 m/z);

xxiv. a twenty-fourth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.7 m/z), a peak having an m/z of from 1270-1273 m/z (preferably about 1271.7 m/z), and a peak having an m/z of from 1284-1287 m/z (preferably about 1285.7 m/z); and xxv. a twenty-fifth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.6 m/z), a peak having an m/z of from 1270-1273 m/z (preferably about 1271.7), and a peak having an m/z of from 1284-1287 m/z (preferably about 1285.7);

d. wherein the presence of said one or more peak set indicates that the subject is not a suitable candidate for receiving a lung transplant; and/or (preferably or)

e. wherein the absence of said one or more peak set indicates that the subject is a suitable candidate for receiving a lung transplant.

In a preferable embodiment, a method of the invention comprises detecting the presence or absence in a mass spectrum output of one or more peak set selected from: said fourth peak set, said fifth peak set, said seventh peak set, said eighth peak set, said ninth peak set, said tenth peak set, said eleventh peak set, said twelfth peak set, said fifteenth peak set, said seventeenth peak set, said eighteenth peak set, said nineteenth peak set, said twenty-first peak set, said twenty-second peak set, said twenty-fourth peak set, and said twenty-fifth peak set.

In another aspect, there is proved a method for screening operating theatre equipment for use in cardiothoracic surgery of a subject, the method comprising:

a. subjecting a sample to mass spectrometry analysis in the positive ion mode and generating a mass spectrum output; wherein said sample is obtained from operating theatre equipment; and b. detecting one or more peak set in said mass spectrum output;

c. wherein said one or more peak set is selected from:

i. a first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z);

ii. a second peak set comprising at least two, three, or four (preferably at least two) defined peaks selected from: a peak having a mass-to-charge ratio (m/z) of from 1220-1223 m/z (preferably about 1221.9 m/z), a peak having a m/z of from 1459-1462 m/z (preferably about 1460.2 m/z), a peak having a m/z of from 1739-1742 m/z (preferably about 1740.5 m/z), and a peak having a m/z of from 1741-1744 m/z (preferably about 1742.5);

iii. a third peak set comprising at least two, three, or four (preferably at least two) defined peaks selected from: a peak having a m/z of from 1242-1245 m/z (preferably about 1243.9 m/z), a peak having a m/z of from 1280-1283 m/z (preferably about 1281.9 m/z), a peak having a m/z of from 1294-1297 m/z (preferably about 1295.9 m/z), and a peak having a m/z of from 1923-1926 m/z (preferably about 1924.2 m/z);

iv. a fourth peak set comprising at least two, three, four, or five (preferably at least two) defined peaks selected from: a peak having a m/z of from 1012-1015 m/z (preferably about 1013.2 m/z), a peak having a m/z of from 1121-1124 m/z (preferably about 1122.8 m/z), a peak having a m/z of from 1122-1125 m/z (preferably about 1123.8 m/z), a peak having an m/z of from 1123-1126 m/z (preferably about 1124.8 m/z), and a peak having a m/z of from 1149-1152 m/z (preferably about 1150.9 m/z);

v. a fifth peak set comprising at least two, three, four, or five (preferably at least two) defined peaks selected from: a peak having a m/z of from 1311-1314 m/z (preferably about 1312.8 m/z), a peak having a m/z of from 1339-1342 m/z (preferably about 1340.8 m/z), a peak having a m/z of from 1474-1477 m/z (preferably about 1475.8 m/z), a peak having a m/z of from 1488-1491 m/z (preferably about 1489.8 m/z), and a peak having a m/z of from 1823-1826 m/z (preferably about 1824 m/z);

vi. a sixth peak pet comprising at least two, three, four, or five (preferably at least two) defined peaks selected from: a peak having a m/z of from 1242-1245 m/z (preferably about 1243.7 m/z), a peak having a m/z of from 1256-1259 m/z (preferably about 1257.8 m/z), a peak having a m/z of from 1270-1273 m/z (preferably about 1271.8 m/z), a peak having a m/z of from 1318-1321 m/z (preferably about 1319.8 m/z), and a peak having a m/z of from 1346-1349 m/z (preferably about 1347.8 m/z);

vii. a seventh peak set comprising at least two, three, or four (preferably at least two) defined peaks selected from: a peak having a m/z of from 1294-1297 m/z (preferably about 1295.9 m/z), a peak having a m/z of from 1296-1299 m/z (preferably about 1297.9 m/z), a peak having a m/z of from 1308-1311 m/z (preferably about 1309.9 m/z), and a peak having a m/z of from 1322-1325 m/z (preferably about 1323.9 m/z);

viii. an eighth peak set comprising at least two defined peaks selected from: a peak having a m/z of from 1370-1373 m/z (preferably about 1371 m/z), and a peak having a m/z of from 1412-1415 m/z (preferably about 1413 m/z);

ix. a ninth peak set comprising at least two, three, or four (preferably at least two) defined peaks selected from: a peak having a m/z of from 2129-2132 m/z (preferably about 2130.4 m/z), a peak having a m/z of from 2171-2174 m/z (preferably about 2172.4 m/z), a peak having a m/z of from 2247-2250 m/z (preferably about 2248.5 m/z), and a peak having a m/z of from 2261-2264 m/z (preferably about 2262.5 m/z);

x. a tenth peak set comprising at least two, three, or four (preferably at least two) defined peaks selected from: a peak having a m/z of from 2273-2276 m/z (preferably about 2274.1 m/z), a peak having a m/z of from 2275-2278 m/z (preferably about 2276.1 m/z), a peak having a m/z of from 2551-2554 m/z (preferably about 2552.2 m/z), and a peak having a m/z of from 2553-2556 m/z (preferably about 2554.2 m/z);

xi. an eleventh peak set comprising at least two, three, or four (preferably at least two) defined peaks selected from: a peak having a m/z of from 1339-1342 m/z (preferably about 1340.8 m/z), a peak having a m/z of from 1353-1356 m/z (preferably about 1354.8 m/z), a peak having a m/z of from 1367-1370 m/z (preferably about 1368.8 m/z), and a peak having an m/z of from 1381-1384 m/z (preferably about 1382.8 m/z);

xii. a twelfth peak set comprising at least two, three, or four (preferably at least two) defined peaks selected from: a peak having an m/z of from 1242-1245 m/z (preferably about 1243.7 m/z), a peak having an m/z of from 1256-1259 m/z (preferably about 1257.7 m/z), a peak having an m/z of from 1270-1273 m/z (preferably about 1271.7 m/z), and a peak having an m/z of from 1298-1301 m/z (preferably about 1299.7 m/z);

xiii. a thirteenth peak set comprising at least two, three, or four (preferably at least two) defined peaks selected from: a peak having an m/z of from 1458-1461 m/z (preferably about 1459.9 m/z), a peak having an m/z of from 2718-2721 m/z (preferably about 2719.6 m/z), a peak having an m/z of from 2760-2763 m/z (preferably about 2761.6 m/z), and a peak having an m/z of from 2788-2791 m/z (preferably about 2789.7 m/z);

xiv. a fourteenth peak set comprising at least two, three, four, or five (preferably at least two) defined peaks selected from: a peak having an m/z of from 1172-1175 m/z (preferably about 1173.9 m/z), a peak having an m/z of from 1174-1177 m/z (preferably about 1175.9 m/z), a peak having an m/z of from 1883-1886 m/z (preferably about 1884.2 m/z), a peak having an m/z of from 1909-1912 m/z (preferably about 1910.2 m/z), and a peak having an m/z of from 1911-1914 m/z (preferably about 1912.2 m/z);

xv. a fifteenth peak set comprising at least two, three, or four (preferably at least two) defined peaks selected from: a peak having an m/z of from 1202-1205 m/z (preferably about 1203.6 m/z), a peak having an m/z of from 1224-1227 m/z (preferably about 1225.6 m/z), a peak having an m/z of from 1226-1229 m/z (preferably about 1227.6 m/z), and a peak having an m/z of from 1240-1243 m/z (preferably about 1241.6 m/z);

xvi. a sixteenth peak set comprising at least two, three, four, or five (preferably at least two) defined peaks selected from: a peak having an m/z of from 1318-1321 m/z (preferably about 1319.9 m/z), a peak having an m/z of from 1332-1335 m/z (preferably about 1333.9 m/z), a peak having an m/z of from 1346-1349 m/z (preferably about 1347.9 m/z), a peak having an m/z of from 1360-1363 m/z (preferably about 1361.9 m/z), and a peak having an m/z of from 1374-1377 m/z (preferably about 1375.9 m/z);

xvii. a seventeenth peak set comprising at least two, three, or four (preferably at least two) defined peaks selected from: a peak having an m/z of from 1308-1311 m/z (preferably about 1309.9 m/z), a peak having an m/z of from 1310-1313 m/z (preferably about 1311.9 m/z), a peak having an m/z of from 1324-1327 m/z (preferably about 1325.9 m/z), and a peak having an m/z of from 1338-1341 m/z (preferably about 1339.9 m/z);

xviii. an eighteenth peak set comprising at least two, three, or four (preferably at least two) defined peaks selected from: a peak having an m/z of from 1012-1015 m/z (preferably about 1013.3 m/z), a peak having an m/z of from 1028-1031 m/z (preferably about 1029.3 m/z), a peak having an m/z of from 1697-1700 m/z (preferably about 1698.2 m/z), and a peak having an m/z of from 1698-1701 m/z (preferably about 1699.2 m/z);

xix. a nineteenth peak set comprising at least two defined peaks selected from: a peak having an m/z of from 1226-1229 m/z (preferably about 1227.9 m/z), and a peak having an m/z of from 1240-1243 m/z (preferably about 1241.9 m/z);

xx. a twentieth peak set comprising at least two, three, four, or five (preferably at least two) defined peaks selected from: a peak having an m/z of from 1414-1417 m/z (preferably about 1416 m/z), a peak having an m/z of from 1443-1446 m/z (preferably about 1444 m/z), a peak having an m/z of from 1445-1448 m/z (preferably about 1446 m/z), a peak having an m/z of from 1515-1518 m/z (preferably about 1516 m/z), and a peak having an m/z of from 1543-1546 m/z (preferably about 1544 m/z);

xxi. a twenty-first peak set comprising at least two, three, four, or five (preferably at least two) defined peaks selected from: a peak having an m/z of from 1036-1039 m/z (preferably about 1037.5 m/z), a peak having an m/z of from 1259-1262 m/z (preferably about 1260.3 m/z), a peak having an m/z of from 1374-1377 m/z (preferably about 1375.7 m/z), a peak having an m/z of from 2497-2500 m/z (preferably about 2498.7 m/z), and a peak having an m/z of from 2835-2838 m/z (preferably about 2837 m/z);

xxii. a twenty-second peak set comprising at least two, three, or four (preferably at least two) defined peaks selected from: a peak having an m/z of from 1057-1060 m/z (preferably about 1058.6 m/z), a peak having an m/z of from 1498-1501 m/z (preferably about 1499.7 m/z), a peak having an m/z of from 1512-1515 m/z (preferably about 1513.7 m/z), and a peak having an m/z of from 1526-1529 m/z (preferably about 1527.7 m/z);

xxiii. a twenty-third peak set comprising at least two, three, or four (preferably at least two) defined peaks selected from: a peak having an m/z of from 1432-1435 m/z (preferably about 1433.7 m/z), a peak having an m/z of from 1446-1449 m/z (preferably about 1447.7 m/z), a peak having an m/z of from 1460-1463 m/z (preferably about 1461.7 m/z), and a peak having an m/z of from 1474-1477 m/z (preferably about 1475.7 m/z);

xxiv. a twenty-fourth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.7 m/z), a peak having an m/z of from 1270-1273 m/z (preferably about 1271.7 m/z), and a peak having an m/z of from 1284-1287 m/z (preferably about 1285.7 m/z); and xxv. a twenty-fifth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.6 m/z), a peak having an m/z of from 1270-1273 m/z (preferably about 1271.7), and a peak having an m/z of from 1284-1287 m/z (preferably about 1285.7);

d. wherein the presence of said one or more peak set indicates that the operating theatre equipment is not suitable to be used during cardiothoracic surgery of a subject; and/or e. wherein the absence of said one or more peak set indicates that the operating theatre equipment is suitable to be used during cardiothoracic surgery of a subject.

Said cardiothoracic surgery may be a lung transplant and/or open-heart surgery. For example, said cardiothoracic surgery may be a lung transplant. In a preferable embodiment, the cardiothoracic is open heart surgery (e.g. cardiac surgery).

An "operating theatre" (also known as an "operating room", "operating suite", or "operation suite") is a facility within a hospital or other medical care centre where surgical operations are carried out (typically in an aseptic environment).

The term "operating theatre equipment" refers to the medical and surgical devises employed during surgery, such as a scalpel, a heart monitor, a heater-cooler device (e.g. and the like). Such equipment should ideally be aseptic.

In a preferable embodiment, the operating theatre equipment is in fluid contact with the subject during cardiothoracic surgery and/or comes into direct contact with the subject during cardiothoracic surgery.

In one embodiment, the operating theatre is in fluid communication with the subject's own natural fluid system. For example, the operating theatre may be in fluid communication with the subject's circulatory system.

In a preferable embodiment, the operating theatre equipment is a heater-cooler device. The heater-cooler device may be the 3T heater-cooler unit (from Livallova).

The skilled person understands that a "heater-cooler device" means equipment typically used during cardiothoracic surgery (e.g. during cardiopulmonary bypass) to help regulate the temperature of a patient's blood during cardiac, vascular or transplant surgery. Typically, the device uses water to warm or cool the blood as it is circulated outside of the patient's body (e.g. and circulated through the device).

A further aspect of the invention provides a method for identifying the presence or absence of a bacterial infection in a subject subsequent to receiving cardiothoracic surgery, the method comprising:

a. subjecting a sample to mass spectrometry analysis in the positive ion mode and generating a mass spectrum output; wherein said sample is an isolated sample obtained from a subject that has received cardiothoracic surgery; and b. detecting one or more peak set in said mass spectrum output;

c. wherein said one or more peak set is selected from:

i. a first peak set comprising at least two, three, or four (preferably at least two) defined peaks selected from: a peak having a m/z of from 1256-1259 m/z (preferably about 1257.8 m/z), a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z);

ii. a second peak set comprising at least two, three, or four (preferably at least two) defined peaks selected from: a peak having a mass-to-charge ratio (m/z) of from 1220-1223 m/z (preferably about 1221.9 m/z), a peak having a m/z of from 1459-1462 m/z (preferably about 1460.2 m/z), a peak having a m/z of from 1739-1742 m/z (preferably about 1740.5 m/z), and a peak having a m/z of from 1741-1744 m/z (preferably about 1742.5);

iii. a third peak set comprising at least two, three, or four (preferably at least two) defined peaks selected from: a peak having a m/z of from 1242-1245 m/z (preferably about 1243.9 m/z), a peak having a m/z of from 1280-1283 m/z (preferably about 1281.9 m/z), a peak having a m/z of from 1294-1297 m/z (preferably about 1295.9 m/z), and a peak having a m/z of from 1923-1926 m/z (preferably about 1924.2 m/z);

iv. a fourth peak set comprising at least two, three, four, or five (preferably at least two) defined peaks selected from: a peak having a m/z of from 1012-1015 m/z (preferably about 1013.2 m/z), a peak having a m/z of from 1121-1124 m/z (preferably about 1122.8 m/z), a peak having a m/z of from 1122-1125 m/z (preferably about 1123.8 m/z), a peak having an m/z of from 1123-1126 m/z (preferably about 1124.8 m/z), and a peak having a m/z of from 1149-1152 m/z (preferably about 1150.9 m/z);

v. a fifth peak set comprising at least two, three, four, or five (preferably at least two) defined peaks selected from: a peak having a m/z of from 1311-1314 m/z (preferably about 1312.8 m/z), a peak having a m/z of from 1339-1342 m/z (preferably about 1340.8 m/z), a peak having a m/z of from 1474-1477 m/z (preferably about 1475.8 m/z), a peak having a m/z of from 1488-1491 m/z (preferably about 1489.8 m/z), and a peak having a m/z of from 1823-1826 m/z (preferably about 1824 m/z);

vi. a sixth peak pet comprising at least two, three, four, or five (preferably at least two) defined peaks selected from: a peak having a m/z of from 1242-1245 m/z (preferably about 1243.7 m/z), a peak having a m/z of from 1256-1259 m/z (preferably about 1257.8 m/z), a peak having a m/z of from 1270-1273 m/z (preferably about 1271.8 m/z), a peak having a m/z of from 1318-1321 m/z (preferably about 1319.8 m/z), and a peak having a m/z of from 1346-1349 m/z (preferably about 1347.8 m/z);

vii. a seventh peak set comprising at least two, three, or four (preferably at least two) defined peaks selected from: a peak having a m/z of from 1294-1297 m/z (preferably about 1295.9 m/z), a peak having a m/z of from 1296-1299 m/z (preferably about 1297.9 m/z), a peak having a m/z of from 1308-1311 m/z (preferably about 1309.9 m/z), and a peak having a m/z of from 1322-1325 m/z (preferably about 1323.9 m/z);

viii. an eighth peak set comprising at least two defined peaks selected from: a peak having a m/z of from 1370-1373 m/z (preferably about 1371 m/z), and a peak having a m/z of from 1412-1415 m/z (preferably about 1413 m/z);

ix. a ninth peak set comprising at least two, three, or four (preferably at least two) defined peaks selected from: a peak having a m/z of from 2129-2132 m/z (preferably about 2130.4 m/z), a peak having a m/z of from 2171-2174 m/z (preferably about 2172.4 m/z), a peak having a m/z of from 2247-2250 m/z (preferably about 2248.5 m/z), and a peak having a m/z of from 2261-2264 m/z (preferably about 2262.5 m/z);

x. a tenth peak set comprising at least two, three, or four (preferably at least two) defined peaks selected from: a peak having a m/z of from 2273-2276 m/z (preferably about 2274.1 m/z), a peak having a m/z of from 2275-2278 m/z (preferably about 2276.1 m/z), a peak having a m/z of from 2551-2554 m/z (preferably about 2552.2 m/z), and a peak having a m/z of from 2553-2556 m/z (preferably about 2554.2 m/z);

xi. an eleventh peak set comprising at least two, three, or four (preferably at least two) defined peaks selected from: a peak having a m/z of from 1339-1342 m/z (preferably about 1340.8 m/z), a peak having a m/z of from 1353-1356 m/z (preferably about 1354.8 m/z), a peak having a m/z of from 1367-1370 m/z (preferably about 1368.8 m/z), and a peak having an m/z of from 1381-1384 m/z (preferably about 1382.8 m/z);

xii. a twelfth peak set comprising at least two, three, or four (preferably at least two) defined peaks selected from: a peak having an m/z of from 1242-1245 m/z (preferably about 1243.7 m/z), a peak having an m/z of from 1256-1259 m/z (preferably about 1257.7 m/z), a peak having an m/z of from 1270-1273 m/z (preferably about 1271.7 m/z), and a peak having an m/z of from 1298-1301 m/z (preferably about 1299.7 m/z);

xiii. a thirteenth peak set comprising at least two, three, or four (preferably at least two) defined peaks selected from: a peak having an m/z of from 1458-1461 m/z (preferably about 1459.9 m/z), a peak having an m/z of from 2718-2721 m/z (preferably about 2719.6 m/z), a peak having an m/z of from 2760-2763 m/z (preferably about 2761.6 m/z), and a peak having an m/z of from 2788-2791 m/z (preferably about 2789.7 m/z);

xiv. a fourteenth peak set comprising at least two, three, four, or five (preferably at least two) defined peaks selected from: a peak having an m/z of from 1172-1175 m/z (preferably about 1173.9 m/z), a peak having an m/z of from 1174-1177 m/z (preferably about 1175.9 m/z), a peak having an m/z of from 1883-1886 m/z (preferably about 1884.2 m/z), a peak having an m/z of from 1909-1912 m/z (preferably about 1910.2 m/z), and a peak having an m/z of from 1911-1914 m/z (preferably about 1912.2 m/z);

xv. a fifteenth peak set comprising at least two, three, or four (preferably at least two) defined peaks selected from: a peak having an m/z of from 1202-1205 m/z (preferably about 1203.6 m/z), a peak having an m/z of from 1224-1227 m/z (preferably about 1225.6 m/z), a peak having an m/z of from 1226-1229 m/z (preferably about 1227.6 m/z), and a peak having an m/z of from 1240-1243 m/z (preferably about 1241.6 m/z);

xvi. a sixteenth peak set comprising at least two, three, four, or five (preferably at least two) defined peaks selected from: a peak having an m/z of from 1318-1321 m/z (preferably about 1319.9 m/z), a peak having an m/z of from 1332-1335 m/z (preferably about 1333.9 m/z), a peak having an m/z of from 1346-1349 m/z (preferably about 1347.9 m/z), a peak having an m/z of from 1360-1363 m/z (preferably about 1361.9 m/z), and a peak having an m/z of from 1374-1377 m/z (preferably about 1375.9 m/z);

xvii. a seventeenth peak set comprising at least two, three, or four (preferably at least two) defined peaks selected from: a peak having an m/z of from 1308-1311 m/z (preferably about 1309.9 m/z), a peak having an m/z of from 1310-1313 m/z (preferably about 1311.9 m/z), a peak having an m/z of from 1324-1327 m/z (preferably about 1325.9 m/z), and a peak having an m/z of from 1338-1341 m/z (preferably about 1339.9 m/z);

xviii. an eighteenth peak set comprising at least two, three, or four (preferably at least two) defined peaks selected from: a peak having an m/z of from 1012-1015 m/z (preferably about 1013.3 m/z), a peak having an m/z of from 1028-1031 m/z (preferably about 1029.3 m/z), a peak having an m/z of from 1697-1700 m/z (preferably about 1698.2 m/z), and a peak having an m/z of from 1698-1701 m/z (preferably about 1699.2 m/z);

xix. a nineteenth peak set comprising at least two defined peaks selected from: a peak having an m/z of from 1226-1229 m/z (preferably about 1227.9 m/z), and a peak having an m/z of from 1240-1243 m/z (preferably about 1241.9 m/z);

xx. a twentieth peak set comprising at least two, three, four, or five (preferably at least two) defined peaks selected from: a peak having an m/z of from 1414-1417 m/z (preferably about 1416 m/z), a peak having an m/z of from 1443-1446 m/z (preferably about 1444 m/z), a peak having an m/z of from 1445-1448 m/z (preferably about 1446 m/z), a peak having an m/z of from 1515-1518 m/z (preferably about 1516 m/z), and a peak having an m/z of from 1543-1546 m/z (preferably about 1544 m/z);

xxi. a twenty-first peak set comprising at least two, three, four, or five (preferably at least two) defined peaks selected from: a peak having an m/z of from 1036-1039 m/z (preferably about 1037.5 m/z), a peak having an m/z of from 1259-1262 m/z (preferably about 1260.3 m/z), a peak having an m/z of from 1374-1377 m/z (preferably about 1375.7 m/z), a peak having an m/z of from 2497-2500 m/z (preferably about 2498.7 m/z), and a peak having an m/z of from 2835-2838 m/z (preferably about 2837 m/z);

xxii. a twenty-second peak set comprising at least two, three, or four (preferably at least two) defined peaks selected from: a peak having an m/z of from 1057-1060 m/z (preferably about 1058.6 m/z), a peak having an m/z of from 1498-1501 m/z (preferably about 1499.7 m/z), a peak having an m/z of from 1512-1515 m/z (preferably about 1513.7 m/z), and a peak having an m/z of from 1526-1529 m/z (preferably about 1527.7 m/z);

xxiii. a twenty-third peak set comprising at least two, three, or four (preferably at least two) defined peaks selected from: a peak having an m/z of from 1432-1435 m/z (preferably about 1433.7 m/z), a peak having an m/z of from 1446-1449 m/z (preferably about 1447.7 m/z), a peak having an m/z of from 1460-1463 m/z (preferably about 1461.7 m/z), and a peak having an m/z of from 1474-1477 m/z (preferably about 1475.7 m/z);

xxiv. a twenty-fourth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.7 m/z), a peak having an m/z of from 1270-1273 m/z (preferably about 1271.7 m/z), and a peak having an m/z of from 1284-1287 m/z (preferably about 1285.7 m/z); and xxv. a twenty-fifth peak set comprising at least two, three, or four (preferably at least two) defined peaks selected from: a peak having an m/z of from 1242-1245 m/z (preferably about 1243.6 m/z), a peak having an m/z of from 1256-1259 m/z (preferably about 1257.6 m/z), a peak having an m/z of from 1270-1273 m/z (preferably about 1271.7), and a peak having an m/z of from 1284-1287 m/z (preferably about 1285.7);

d. wherein the presence of said one or more peak set is indicative of the presence of a bacterial infection in the subject subsequent to receiving cardiothoracic surgery; and/or (preferably or)

e. wherein the absence of said one or more peak set is indicative of the absence of a bacterial infection in a subject subsequent to receiving cardiothoracic surgery.

In one embodiment, a method (e.g. any method described herein) of the invention may comprise detecting one or more further peak set selected from:

i. a twenty-sixth peak set comprising at least two defined peaks (for example, at least three, four, five or six defined peaks) selected from: a peak having a m/z of from 1545-1548 m/z (preferably about 1546 m/z), a peak having a m/z of from 1559-1562 m/z (preferably about 1560 m/z), a peak having a m/z of from 1561-1564 m/z (preferably about 1562 m/z), a peak having a m/z of from 1573-1576 (preferably about 1574 m/z), a peak having a m/z of from 1587-1590 m/z (preferably about 1588 m/z), and a peak having a m/z of from 1615-1618 m/z (preferably about 1616 m/z);

ii. a twenty-seventh peak set comprising at least two defined peaks (for example, at least three, four, or five defined peaks) selected from: a peak having a m/z of from 1270-1273 m/z (preferably about 1271.9 m/z), a peak having a m/z of from 1294-1297 m/z (preferably about 1296.9 m/z), a peak having a m/z of from 1296-1299 m/z (preferably about 1297.9 m/z), a peak having a m/z of from 1322-1325 m/z (preferably about 1323.9 m/z), and a peak having a m/z of from 2039-2042 m/z (preferably about 2040.4 m/z);

iii. a twenty-eighth peak set comprising at least two defined peaks (for example, at least three, or four defined peaks) selected from: a peak having a m/z of from 1390-1393 m/z (preferably about 1391 m/z), 1404-1407 m/z (preferably about 1405 m/z), 1420-1423 m/z (preferably about 1421 m/z), and 1446-1449 m/z (preferably about 1447 m/z);

iv. a twenty-ninth peak set comprising at least two defined peaks (for example, at least three, or four defined peaks) selected from: a peak having a m/z of from 1325-1328 m/z (preferably about 1326.7 m/z), a peak having a m/z of from 1353-1356 m/z (preferably about 1354.8 m/z), a peak having a m/z of from 1369-1372 m/z (preferably about 1370.7 m/z), and a peak having a m/z of from 1381-1384 m/z (preferably about 1382.8 m/z);

v. a thirtieth peak set comprising at least two defined peaks (for example, at least three, four, or five defined peaks) selected from: a peak having a m/z of from 1294-1297 m/z (preferably about 1295.7 m/z), a peak having a m/z of from 1296-1299 m/z (preferably about 1297.7 m/z), a peak having a m/z of from 1338-1341 m/z (preferably about 1339.7 m/z), a peak having a m/z of from 2036-2039 m/z (preferably about 2037 m/z), and a peak having a m/z of from 2038-2041 m/z (preferably about 2039 m/z);

vi. a thirty-first peak set comprising at least two defined peaks (for example, at least three or four defined peaks) selected from: a peak having a m/z of from 1242-1245 m/z (preferably about 1243.9 m/z), a peak having a m/z of from 1256-1259 m/z (preferably about 1257.9 m/z), a peak having a m/z of from 1270-1273 m/z (preferably about 1271.9 m/z), and a peak having a m/z of from 1298-1301 m/z (preferably about 1299.9 m/z);

vii. a thirty-second peak set comprising at least two defined peaks (for example, at least three, or four defined peaks) selected from: a peak having a m/z of from 1332-1335 m/z (preferably about 1333.9 m/z), a peak having a m/z of from 1358-1361 m/z (preferably about 1359.9 m/z), a peak having a m/z of from 1360-1363 m/z (preferably about 1361.9 m/z), and a peak having a m/z of from 1386-1389 m/z (preferably about 1387.9 m/z);

viii. a thirty-third peak set comprising at least two defined peaks (for example, at least three, or four defined peaks) selected from: a peak having a m/z of from 1318-1321 m/z (preferably about 1319.9 m/z), a peak having a m/z of from 1332-1335 m/z (preferably about 1333.9 m/z), a peak having a m/z of from 1346-1349 m/z (preferably about 1347.9 m/z), and a peak having a m/z of from 1360-1363 m/z (preferably about 1361.9 m/z);

ix. a thirty-fourth peak set comprising at least two defined peaks (for example, at least three, or four defined peaks) selected from: a peak having a m/z of from 1012-1015 m/z (preferably about 1013.4 m/z), a peak having a m/z of from 1294-1297 m/z (preferably about 1295.9 m/z), a peak having a m/z of from 1308-1311 m/z (preferably about 1309.9 m/z), and a peak having a m/z of from 1310-1313 m/z (preferably about 1311.9 m/z);

x. a thirty-fifth peak set comprising at least two defined peaks (for example, at least three, or four defined peaks) selected from: a peak having a m/z of from 1296-1299 m/z (preferably about 1297.8 m/z), a peak having a m/z of from 1310-1313 m/z (preferably about 1311.8 m/z), a peak having a m/z of from 1324-1327 m/z (preferably about 1325.8 m/z), and a peak having a m/z of from 1338-1341 m/z (preferably about 1339.8 m/z);

xi. a thirty-sixth peak set comprising at least two defined peaks (for example, at least three, or four defined peaks) selected from: a peak having a m/z of from 1252-1255 m/z (preferably about 1253.9 m/z), a peak having a m/z of from 1266-1269 m/z (preferably about 1267.9), a peak having a m/z of from 1268-1271 m/z (preferably about 1269.9 m/z), and a peak having a m/z of from 1280-1283 m/z (preferably about 1281.9 m/z); and xii. a thirty-seventh peak set comprising at least two defined peaks (for example, at least three, or four defined peaks) selected from: a peak having a m/z of from 1184-1187 m/z (preferably about 1185.6 m/z), a peak having a m/z of from 1202-1205 m/z (preferably about 1203.6 m/z), a peak having a m/z of from 1226-1229 m/z (preferably about 1227.6 m/z), and a peak having a m/z of from 1240-1243 m/z (preferably about 1241.6 m/z).

A key advantage of performing mass spectrometry analysis in the positive ion mode is the suitability of this mode for use in clinical laboratories. Mass spectrometry analysis in the negative ion mode also finds utility in clinical laboratories, and may be used to complement analysis performed in the positive ion mode. For example, a sample may be run in both the positive ion mode and negative ion mode to provide at least two mass spectra outputs for a given sample, to increase sensitivity/specificity of detection.

Alternatively or additionally (preferably additionally) a corresponding mass spectrometry analysis may be performed in the negative ion mode. For example, the presence or absence of a peak set in both the positive ion mode and negative ion mode may be detected. Advantageously, this may increase the confidence in identifying a patient suitable for receiving a lung transplant and/or detecting the presence or absence of a bacterial infection.

As an additional technical feature, or as an alternative technical feature, a method of the present invention may include: subjecting a sample to mass spectrometry analysis in the negative ion mode and generating a mass spectrum output; wherein said sample is an isolated sample obtained from a subject that is a candidate for receiving a lung transplant; or wherein said sample is obtained from operating theatre equipment; or wherein said sample is an isolated sample obtained from a subject that has received open heart surgery and/or a heart transplant; and detecting one or more peak set (e.g. one or more further peak set) in said mass spectrum output; wherein said one or more peak set is selected from:

i. a thirty-eighth peak set comprising at least two defined peaks (for example, at least three, four, or five defined peaks) selected from: a peak having a m/z of from 605-608 m/z (preferably about 607 m/z), a peak having a m/z of from 774-777 m/z (preferably about 776 m/z), a peak having a m/z of from 775-778 m/z (preferably about 777 m/z), a peak having a m/z of from 850-853 m/z (preferably about 851 m/z), and a peak having a m/z of from 1412-1415 m/z (preferably about 1413 m/z);

ii. a thirty-ninth peak set comprising at least two defined peaks (for example, at least three, four, or five defined peaks) selected from: a peak having a m/z of from 1232-1235 m/z (preferably about 1233 m/z), a peak having a m/z of from 1332-1325 m/z (preferably about 1323 m/z), a peak having a m/z of from 1324-1327 m/z (preferably about 1325 m/z), a peak having a m/z of from 1350-1353 m/z (preferably about 1351 m/z), and a peak having a m/z of from 1364-1367 m/z (preferably about 1365 m/z); and iii. a fortieth peak set comprising at least two defined peaks (for example, at least three, four, or five defined peaks) selected from: a peak having a m/z of from 1214-1217 m/z (preferably about 1215 m/z), a peak having a m/z of from 1256-1259 m/z (preferably about 1257 m/z), a peak having a m/z of from 1282-1285 m/z (preferably about 1283 m/z), a peak having a m/z of from 1283-1287 m/z (preferably about 1285 m/z), and a peak having a m/z of from 1309-1313 m/z (preferably about 1311 m/z).

iv. a forty-first peak set comprising at least two defined peaks (for example, at least three, four, or five defined peaks) selected from: a peak having a m/z of from 481-484 m/z (preferably about 482 m/z), a peak having a m/z of from 482-485 m/z (preferably about 483 m/z), a peak having a m/z of from 484-487 m/z (preferably about 485 m/z), a peak having a m/z of from 496-499 m/z (preferably about 497 m/z), a peak having a m/z of from 497-500 m/z (preferably about 499 m/z), a peak having a m/z of from 504-507 m/z (preferably about 505 m/z), a peak having a m/z of from 658-661 m/z (preferably about 659 m/z), a peak having a m/z of from 660-663 m/z (preferably about 661 m/z), a peak having a m/z of from 674-677 m/z (preferably about 675 m/z), a peak having a m/z of from 680-683 m/z (preferably about 681 m/z), a peak having a m/z of from 681-684 m/z (preferably about 682 m/z), and a peak having a m/z of from 696-699 m/z (preferably about 687 m/z);

v. a forty-second peak set comprising at least two defined peaks (for example, at least three, four, or five defined peaks) selected from: a peak having a m/z of from 480-483 m/z (preferably about 482 m/z), 482-485 m/z (preferably about 483 m/z), a peak having a m/z of from 484-487 m/z (preferably about 485 m/z), a peak having a m/z of from 496-499 m/z (preferably about 497 m/z), a peak having a m/z of from 497-500 m/z (preferably about 499 m/z), a peak having a m/z of from 503-506 m/z (preferably about 505 m/z), a peak having a m/z of from 519-522 m/z (preferably about 521 m/z), a peak having a m/z of from 534-537 m/z (preferably about 536 m/z), a peak having a m/z of from 535-538 m/z (preferably about 537 m/z), a peak having a m/z of from 658-661 m/z (preferably about 659 m/z), a peak having a m/z of from 660-663 m/z (preferably about 661 m/z), a peak having a m/z of from 673-676 m/z (preferably about 675 m/z), a peak having a m/z of from 680-683 m/z (preferably about 681 m/z), a peak having a m/z of from 1402-1405 m/z (preferably about 1404 m/z), a peak having a m/z of from 1565-1568 m/z (preferably about 1567 m/z), a peak having a m/z of from 1567-1570 m/z (preferably about 1569 m/z), a peak having a m/z of from 1577-1580 m/z (preferably about 1579 m/z), a peak having a m/z of from 1580-1583 m/z (preferably about 1582 m/z), a peak having a m/z of from 1621-1624 m/z (preferably about 1622 m/z), a peak having a m/z of from 1623-1626 m/z (preferably about 1624 m/z), a peak having a m/z of from 1637-1640 m/z (preferably about 1638 m/z), a peak having a m/z of from 1638-1641 m/z (preferably about 1639 m/z), a peak having a m/z of from 1647-1650 m/z (preferably about 1648 m/z), a peak having a m/z of from 1648-1651 m/z (preferably about 1649 m/z), a peak having a m/z of from 1649-1652 m/z (preferably about 1650 m/z), a peak having a m/z of from 1663-1666 m/z (preferably about 1664 m/z), a peak having a m/z of from 1664-1667 m/z (preferably about 1665 m/z), a peak having a m/z of from 2296-2299 m/z (preferably about 2297 m/z), and a peak having a m/z of from 2297-2300 m/z (preferably about 2298 m/z); and vi. a forty-third peak set comprising at least two defined peaks (for example, at least three, four, or five defined peaks) selected from: a peak having a m/z of from 407-410 m/z (409 m/z), a peak having a m/z of from 482-485 m/z (483 m/z), a peak having a m/z of from 484-487 m/z (485 m/z), a peak having a m/z of from 490-493 m/z (491 m/z), a peak having a m/z of from 496-499 m/z (498 m/z), a peak having a m/z of from 497-500 m/z (499 m/z), a peak having a m/z of from 504-507 m/z (505 m/z), and a peak having a m/z of from 512-515 m/z (513 m/z).

As an additional technical feature, or as an alternative technical feature, a method of the present invention may include: subjecting a sample to mass spectrometry analysis in the negative ion mode and generating a mass spectrum output; wherein said sample is an isolated sample obtained from a subject that is a candidate for receiving a lung transplant; or wherein said sample is obtained from operating theatre equipment; or wherein said sample is an isolated sample obtained from a subject that has received open heart surgery and/or a heart transplant; and detecting one or more peak set (e.g. one or more further peak set) in said mass spectrum output; wherein said one or more peak set is selected from:

i. a thirty-eighth peak set comprising at least two defined peaks (for example, at least three, four, or five defined peaks) selected from: a peak having a m/z of from 605-608 m/z (preferably about 607 m/z), a peak having a m/z of from 774-777 m/z (preferably about 776 m/z), a peak having a m/z of from 775-778 m/z (preferably about 777 m/z), a peak having a m/z of from 850-853 m/z (preferably about 851 m/z), and a peak having a m/z of from 1412-1415 m/z (preferably about 1413 m/z);

ii. a thirty-ninth peak set comprising at least two defined peaks (for example, at least three, four, or five defined peaks) selected from: a peak having a m/z of from 1232-1235 m/z (preferably about 1233 m/z), a peak having a m/z of from 1332-1325 m/z (preferably about 1323 m/z), a peak having a m/z of from 1324-1327 m/z (preferably about 1325 m/z), a peak having a m/z of from 1350-1353 m/z (preferably about 1351 m/z), and a peak having a m/z of from 1364-1367 m/z (preferably about 1365 m/z); and iii. a fortieth peak set comprising at least two defined peaks (for example, at least three, four, or five defined peaks) selected from: a peak having a m/z of from 1214-1217 m/z (preferably about 1215 m/z), a peak having a m/z of from 1256-1259 m/z (preferably about 1257 m/z), a peak having a m/z of from 1282-1285 m/z (preferably about 1283 m/z), a peak having a m/z of from 1283-1287 m/z (preferably about 1285 m/z), and a peak having a m/z of from 1309-1313 m/z (preferably about 1311 m/z).

In a preferable embodiment, said peak (e.g. defined peak) is indicative of the presence of a bacterial membrane lipid (e.g. the defined peak correlates with the detection of a bacterial membrane lipid). Preferably, said peak is absent from a corresponding mass spectrum output for a sample lacking said bacterial membrane lipid.

In one embodiment, a sample is admixed with a matrix solution prior to subjecting said sample to mass spectrometry analysis in the positive ion mode and/or negative ion mode (preferably positive ion mode). A matrix solution facilitates mass spectrometry analysis of a sample, preferably wherein the mass spectrometry is MALDI-TOF mass spectrometry.

Advantageously, a matrix solution of the invention may allow for the ionisation (e.g. selective ionisation) of a bacterial membrane lipid as an integral component (e.g. part of) of a bacterial membrane. Preferably, a matrix solution of the invention may allow for the extraction and/or ionisation of a bacterial membrane lipid as an integral part (e.g. component) of a bacterial membrane. A matrix solution of the invention may allow for the selective extraction, co-crystallization and/or ionisation of a bacterial membrane lipid as an integral part (e.g. component) of a bacterial membrane.

In one embodiment, a matrix solution of the invention allows for the identification of a peak corresponding to (e.g. assigned to) a bacterial membrane lipid as an integral part of a bacterial membrane (e.g. by allowing the extraction, co-crystallization and ionisation of the bacterial membrane lipid).

Said bacterial membrane lipid may be one or more selected from a sulfoglycolipid (SGL), a phosphatidyl-myo-inositol (PI), phosphatidyl-myo-inositol-dimannosides (PIM), a pentaacyltrehalose (PAT), a glycerol monomycolate (GroMM), a phenolic glycolipid (PGL), triacylglycerol (TAG), a glycopeptidolipid (GPL), a C-mycoside, or a combination thereof.

In one embodiment, a matrix solution comprises a matrix (e.g. which may be used interchangeably with the term "mass spectrometry matrix" herein) suspended in an organic solvent.

In one embodiment, a matrix solution comprises a matrix suspended in an organic solvent at a concentration of about 1 to 100 mg/ml (e.g. about 10-90 mg/ml, 20-80 mg/ml, 30-70 mg/ml, or 40-60 mg/ml) (the "concentration" referring to the concentration of the matrix). In one embodiment, a matrix solution comprises a matrix suspended in an organic solvent at a concentration of about 7 to 13 mg/ml. Preferably, the matrix may be suspended in an organic solvent (preferably EtOH) at a concentration of about 10 mg/ml.

The term "matrix" (e.g. which may be used interchangeably with the term "mass spectrometry matrix" herein) means a laser energy absorbing matrix suitable for creating ions from large molecules (e.g. with minimal fragmentation), such that the ions may be analysed by mass spectrometry.

In one embodiment, a matrix solution comprises one or more matrix selected from norharmane (NRM), 3-Hydroxymethyl-β-carboline, 3-Methyl-a-carboline, Ethyl 2,3, 4,9-tetrahydro-1H-β-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3, 4-tetrahydro-beta-carboline-1-carboxylic acid, 1,2,3,4-Tetrahydro-9H-pyrido[3,4-b]indole, harmane, harmine, harmaline or a combination thereof suspended in an organic solvent. In one embodiment, a matrix solution comprises one or more selected from norharmane (NRM), 3-Hydroxymethyl-β-carboline, 3-Methyl-a-carboline, Ethyl 2,3, 4,9-tetrahydro-1H-β-carboline-3-carboxylate, Ethyl β-carboline carboxylate, 1-Methylindole-2-carboxylic acid, norharman methiodide, β-Carboline carboxylic acid N-methylamide, harmaline hydrochloride dehydrate, 1,2,3, 4-tetrahydro-beta-carboline-1-carboxylic acid, 1,2,3,4-Tetrahydro-9H-pyrido[3,4-b]indole, harmane, harmine, harmaline or a combination thereof suspended in an organic solvent at a concentration of 1 to 100 mg/ml. In one embodiment, a matrix solution comprises one or more matrix selected from norharmane (NRM), 3-Hydroxymethyl-β-carboline, 3-Methyl-a-carboline, Ethyl 2,3,4,9-tetrahydro-1H-β-carboline-3-carboxylate, Ethyl β-carboline-3-carboxylate, 1-Methylindole carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido [3,4-b]indole, harmane, harmine, harmaline or a combination thereof suspended in an organic solvent at a concentration of 7 to 13 mg/ml. In a preferable embodiment, a matrix solution comprises one or more matrix selected from norharmane (NRM), 3-Hydroxymethyl-β-carboline, 3-Methyl-a-carboline, Ethyl 2,3,4,9-tetrahydro-1H-8-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido[3,4-b]indole, harmane, harmine, harmaline or a combination thereof, preferably suspended in an organic solvent at a concentration of 10 mg/ml.

In one embodiment, a matrix solution comprises norharmane (NRM) suspended in an organic solvent. In one embodiment, a matrix solution comprises norharmane suspended in an organic solvent at a concentration of 1 to 100 mg/ml. In one embodiment, a matrix solution comprises norharmane suspended in an organic solvent at a concentration of 7 to 13 mg/ml. In a preferable embodiment, a matrix solution comprises norharmane suspended in an organic solvent (preferably at a concentration of 10 mg/ml).

The matrix may comprise (or consist of) 2,5-dihydroxybenzoic acid. Preferably, the matrix may (or consist of) super 2,5-dihydroxybenzoic acid.

In one embodiment, the organic solvent comprises one or more selected from acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethanol, ethyl acetate, ethylene glycol, glycerine, heptane, Hexamethylphosphoramide (HMPA), Hexamethylphosphorous triamide (HMPT), hexane, methanol, methyl t-butyl ether (MTBE), methylene chloride, N-methyl-2-pyrrolidinone (NMP), pentane, Petroleum ether (ligroine), 1-propanol, 2-propanol, pyridine, tetrahydrofuran (THF), toluene, triethyl amine, water, water (heavy), o-xylene, m-xylene, and p-xylene.

In one embodiment, the organic solvent comprises one or more of chloroform, methanol, dichloromethane, ether, diethyl-ether, petroleum ether, isopropanol, butanol, hexane or a combination thereof.

In one embodiment, the organic solvent comprises chloroform and methanol at a ratio of about 6:1 to about 12:1, or about 8:1 to about 10:1. Suitably an organic solvent comprises chloroform and methanol at a ratio of about 9:1 v/v.

In a preferable embodiment, the organic solvent is ethanol (EtOH). The EtOH may be present a concentration of 5-35% v/v, 10-30% v/v, or 15-25% v/v (preferably about 25% v/v).

Throughout this disclosure, where the concentration of an organic solvent is described in terms of % (v/v), the organic solvent may be diluted in water (such as distilled water) to provide said concentration.

In one embodiment, the ratio of the sample to the matrix solution is between about 0.1:1 to about 2:1 v/v, or about 0.5:1 to about 0.7:1 v/v. Suitably, the ratio of the sample to the matrix solution is about 0.66:1 v/v.

In one embodiment, a matrix solution comprises 2,5-dihydroxybenzoic acid suspended in an organic solvent. In one embodiment, a matrix solution comprises 2,5-dihydroxybenzoic acid suspended in an organic solvent at a concentration of about 1 to 100 mg/ml (e.g. about 10-90 mg/ml, 20-80 mg/ml, 30-70 mg/ml, or 40-60 mg/ml) (the "concentration" referring to the concentration of 2,5-dihydroxybenzoic acid). In one embodiment, a matrix solution comprises 2,5-dihydroxybenzoic acid suspended in an organic solvent at a concentration of about 7 to 13 mg/ml. Preferably, 2,5-dihydroxybenzoic acid is suspended in an organic solvent (preferably EtOH) at a concentration of about 10 mg/ml.

In one embodiment, a matrix solution comprises super 2,5-dihydroxybenzoic acid suspended in an organic solvent. A "super 2,5-dihydroxybenzoic acid" may comprise (or consists of) a 9:1 (w/w) mixture of 2,5-dihydroxybenzoic acid and 2-hydroxy-5-methoxybenzoic acid, respectively.

In one embodiment, a matrix solution comprises super 2,5-dihydroxybenzoic acid suspended in an organic solvent (preferably EtOH) at a concentration of about 1 to 100 mg/ml. In one embodiment, a matrix solution comprises super 2,5-dihydroxybenzoic acid suspended in an organic solvent (preferably EtOH) at a concentration of about 7 to 13 mg/ml. Preferably, super 2,5-dihydroxybenzoic acid is suspended in an organic solvent (preferably EtOH) at a concentration of about 10 mg/ml.

Said super 2,5-dihydroxybenzoic acid may be comprised in said matrix solution either additionally to 2,5-dihydroxybenzoic acid, or alternatively to 2,5-dihydroxybenzoic acid.

In one embodiment, the sample is admixed with a matrix solution prior to subjecting the sample to mass spectrometry analysis, wherein said matrix solution comprises 2,5-dihydroxybenzoic acid and/or super 2,5-dihydroxybenzoic acid suspended in an organic solvent (preferably ethanol).

In a preferable embodiment, the matrix solution comprises <50% (v/v) organic solvent. For example, the matrix solution may comprise 5% to <50% (v/v), or 10% to 45% organic solvent. Preferably, the matrix solution may comprise 20% to 30 & (v/v) organic solvent.

The organic solvent may preferably be ethanol (EtOH). Thus, the matrix solution comprises <50% (v/v) EtOH. For example, the matrix solution may comprise 5% to <50% (v/v), or 10% to 45% EtOH.

In a preferable embodiment, said matrix solution comprises between 20% to 30% ethanol v/v (preferably about 25% ethanol v/v).

Advantageously, an organic solvent (e.g. EtOH) concentration of <50% (v/v) may provide mass spectra having peaks with higher signal-to-noise ratio (relative to the signal-to-noise ratio at concentrations of 50% and above, see Example 35).

The invention further embraces use of a matrix solution for use in a method of the invention described herein.

Thus, another aspect of the invention is predicated on the surprising finding that a matrix solution developed by the present inventors is particularly advantageous for allowing the mass spectrometry (MS) analysis of such lipids, which are traditionally considered to be extremely difficult biomolecules to detect by MS. Surprisingly, said matrix solution allows for the detection of lipids (e.g. lipid fingerprints) in samples comprising intact bacteria.

In one aspect there is provided use of a matrix solution for detecting a bacterial membrane lipid in a sample by mass spectrometry, wherein said matrix solution comprises a matrix suspended in an organic solvent, optionally wherein:

a. said sample is an isolated sample obtained from a subject that is a candidate for receiving a lung transplant;

b. said sample is obtained from operating theatre equipment (for example, a heater-cooler device); and/or c. said sample is an isolated sample obtained from a subject that has received cardiothoracic surgery (for example, open heart surgery and/or a heart transplant).

Preferably wherein said matrix solution comprises 2,5-dihydroxybenzoic acid or super 2,5-dihydroxybenzoic acid (more preferably super 2,5-dihydroxybenzoic acid) suspended in an organic solvent.

Preferably the organic solvent is present at a concentration of <50% (v/v). For example, the matrix solution may comprise 5% to <50% (v/v), or 10% to 45% organic solvent. Preferably, the matrix solution may comprise 20% to 30 & (v/v) organic solvent. Preferably, the organic solvent is EtOH.

A "bacterial membrane lipid" is a lipid comprised within the (typically double layered) outer surface (e.g. membrane) of a bacterial cell. Examples include (but are not limited to) phospholipids, glycolipids, and cholesterol. The term "bacterial membrane lipid" embraces both non-substituted (e.g. native) and substituted lipids. For example, a bacterial membrane lipid may be substituted by substituents such as 4-amino-L-arabinoase and/or phosphoethanolamine.

In one embodiment, methods and uses of the present invention comprise detecting a defined peak in a mass spectrum output, wherein said defined peak comprises a mass-to-charge ratio (m/z) of from 50-40,000 m/z (preferably 50-20,000 m/z; more preferably 800-3000 m/z, even more preferably 1,000-2,200 m/z). Suitably, said peak is indicative of the presence of a bacterial membrane lipid.

In a preferable embodiment, the presence of said peak set is indicative of the presence of a bacterial infection in the subject and the absence of said peak set is indicative of the absence of a bacterial infection in the subject.

Thus, a method of the invention may allow the diagnosis of the presence or absence of a bacterial infection.

Unlike previously available diagnostic techniques, the present invention allow for detection of an infection by utilising a sample comprising an intact bacterium, or bacterial membranes. The present invention can be completed using widely available equipment (e.g. standard mass spectrometry machinery), and does not require the use of toxic solvents, making the invention uniquely compatible with the clinic (e.g. clinical analysis).

Advantageously, the present invention may allow for detection in less than 15 minutes (e.g. upon collection of the sample).

In a preferable embodiment, the method of the invention is for identifying a subject suitable for receiving a lung transplant; wherein the presence of said one or more peak set indicates that the subject is not a suitable candidate for receiving a lung transplant; wherein the absence of said one or more peak set indicates that the subject is a suitable candidate for receiving a lung transplant.

The term "lung transplant" as used herein refers to a procedure to replace a diseased or failing lung with a healthy lung from a donor (e.g. deceased donor). The subject may have received alternative treatments or medications to treat said diseased or failing lung, without a substantial/sufficient improvement.

Colonisation with certain bacteria (in particular, certain NTM mycobacteria such as *Mycobacterium abscessus*) is considered a contraindication to lung transplantation by the International Society of Heart and Lung Transplantation. For example, where there is progressive NTM pulmonary disease (despite optimal antibiotic therapy targeting this organism), the disease/infection is considered to be a contraindication for lung transplantation.

The term "cardiothoracic surgery" (also known as "thoracic surgery") means the surgical treatment of organs inside the thorax (the chest), for example treatment of conditions of the heart (heart disease) and lungs (lung disease).

In a preferable embodiment, the cardiothoracic surgery is open heart surgery.

The term "open heart surgery" as used herein embraces any type of surgery performed on the muscles, valves, or arteries of the heart, preferably surgery in which an excision in the chest is required to access the heart. Open-heart surgery may be undertaken to: repair or replace heart valves, which allow blood to travel through the heart; repair damaged or abnormal areas of the heart implant medical devices that help the heart beat properly; and/or replace a damaged heart with a donated heart (heart transplantation).

The risk of acquiring an infection (e.g. mycobacterial infection) following cardiac surgery has been estimated to be ~1 case per 100,000 coronary artery bypass graft procedures. Typically, the highest risk group may be patients who have undergone valve replacement or repair, whose risk is currently estimated at ~1 case per 5,000 procedures. The consequences of infection are severe (e.g. may cause mortality), an appropriate detection of an infection is important. For example, a global outbreak of *Mycobacterium* chimaera infections (following cardiothoracic surgery) related to a point source contamination of a widely used heater-cooler unit is a major problem; more than 250,000 heart bypass procedures using heater-cooler devices are performed in the United States every year. Thus, *Mycobacterium* chimaera is a significant infection linked to an essential device used to heat and cool the blood during many types of heart surgery.

Heater-cooler devices are used during cardiothoracic surgeries, as well as other medical and surgical procedures to warm or cool a patient to optimize medical care and improve patient outcomes. Heater-cooler devices may include a water tank that provides temperature-controlled water to external heat exchangers or warming/cooling blankets through closed circuits. Although the water in the circuits may not come into direct contact with the patient, there is the potential for contaminated water to enter other parts of the device or transmit bacteria through the air (aerosolize) through the device's exhaust vent into the environment and to the patient.

It is estimated that 60% of these operations use the heater-cooler device associated with this outbreak. Many of the reported cases present with a delayed disseminated infection carrying a high mortality. Diagnosis is difficult as the patient often has an intermittent bacteraemia (difficult to detect) and normal echocardiography.

The term "peak set" as used herein refers to a plurality of peaks, more particularly at least two peaks, identifiable in a mass spectrum output. Preferably, a peak set may represent a bacterial membrane lipid fingerprint. The term "peak set" may be used synonymously with the term "lipid fingerprint".

The skilled person appreciates that a "peak" (e.g. a defined peak) in a mass spectrum output comprises a de minimus intensity value above the background. In one embodiment, a 'peak' may comprise any m/z value(s) having an intensity of at least twice (e.g. 2×) the intensity of the average intensity of background peaks. Suitably, a peak may comprise any m/z value(s) having an intensity of at least six times (e.g. 6×) or eight times (e.g. 8×) the intensity of the average intensity of background peaks. Suitably, a peak may comprise any m/z value(s) having an intensity of at least ten times (e.g. 10×) or twelve times (e.g. 12×) the intensity of the average intensity of background peaks.

For simplicity, the term "defined peak" is used interchangeably with the term "peak" herein. Thus, reference to a "peak" means a defined peak.

The intensity of said peak set(s) may be expressed as a relative intensity (an intensity ratio value), wherein the intensity value of the most intense peak of the peak set (corresponding to the most abundant analyte in the sample) is set at 100%, with the remaining peaks having a relative intensity (an intensity ratio value) which is relative to said most intense peak (e.g. wherein a peak having half the intensity of said most intense peak has an intensity ratio value of 50%). The relative intensity may be referred to as an "intensity 100%".

Preferably, the intensity of peaks of said peak set(s) may be expressed as a relative intensity (an intensity ratio value), wherein the intensity value of the most intense peak of the mass spectrum output (e.g. corresponding to the most abundant analyte in the sample) is set at 100%, with the remaining peaks having a relative intensity (an intensity ratio value) which is relative to said most intense peak (wherein a peak having half the intensity of said most intense peak has an intensity ratio value of 50%). The relative intensity may be referred to as an "intensity 100%".

The peaks may comprise a relative intensity (an intensity ratio value) of at least 10%, 20%, 30%, 40%, 50%, 60%, 70%, 80%, or 90% (for example, at least 10%). Preferably, the peaks may comprise a relative intensity (an intensity ratio value) or at least 50%, 60% or 70%.

In a preferable embodiment, the at least two peaks of a peak set described herein comprise a relative intensity (e.g. an intensity ratio value) of at least 75%. Focusing on the detection of peaks having such (minimum) intensity ratio value advantageously increases the sensitivity (e.g. confidence) in the detection of analyte(s) relevant for identifying a subject suitable for receiving a lung transplant and/or a bacterial infection.

The skilled person understands that a "peak" corresponds to an (detected) analyte in the sample, and comprises a mass-to-charge ratio (m/z) value indicative of (e.g. corresponding to) the mass of the analyte (typically in said analyte's most abundant form). The skilled person understands that the m/z value of a peak corresponding to any given analyte may vary (typically by plus or minus about 1-3 m/z) depending on e.g. the equipment used (mass spectrometry equipment may vary in precision). Furthermore, the m/z value may shift due to modifications (e.g. substitutions) to the analyte. Thus, the skilled person understands that an m/z value for a peak for an analyte may vary within a degree of tolerance. By way of example, an expected m/z peak value of a specific bacterial membrane lipid may be 1013.2 m/z, and the skilled person understands that (due to above described variability) said peak may be presented in a mass spectrum output with an m/z value in the range of from 1012-1015 m/z.

The "sample" may be a clinical sample. In one embodiment a sample is whole blood, serum, plasma, oral samples such as saliva, pus, vaginal sample, stool samples, vomitus, cerebrospinal fluid, tear fluid, synovial fluid, sputum, prepared or processed clinical samples (e.g. for the removal of salt). A sample may be prepared, for example, where appropriate, diluted or concentrated, or dialysed and stored by standard means. A sample typically comprises or is suspected of comprising a bacterium (preferably between $10^1$ to $10^{10}$ bacterial cells, for example, between $10^2$ to $10^8$ bacterial cells, between $10^3$ to $10^7$ bacterial cells, between $10^4$ to $10^6$ bacterial cells). The sample may be a tissue homogenate, tissue section and/or biopsy specimen from a live subject, or taken post-mortem.

In one embodiment, the sample is isolated from the circulatory system. For example, the sample may be obtained from an isolated heart sample. The sample may be whole blood, serum, or plasma.

In one embodiment, the sample is an isolated sample from the respiratory system. For example, the sample may be obtained from an isolated lung sample. Suitable samples include tracheal aspirate, sputum and/or Bronchoalveolar lavage. Such samples are preferable in methods for identifying a subject suitable for receiving a lung transplant. In a preferable embodiment, the sample is a bacterial culture derived from a sample (patient/subject sample) described herein (e.g. the sample is a clinical isolate of a bacterium). For example, the (isolate) sample may be a bacterial culture recovered from a sputum sample.

A sample obtained from operating theatre equipment may be water obtained from a heater-cooler device. The sample may be a bacterial culture derived from said water (for example, derived by contacting the water with bacterial culture medium and incubating the bacterial culture medium).

The sample may be a sample (e.g. clinical sample) that has been subjected to one or more processing steps. For example, the sample may be subjected to dialysis (e.g. to reduce the concentration of a salt in said sample).

In one embodiment, the sample comprises a bacterial membrane. Reference to a "bacterial membrane" embraces a fragment thereof.

In one embodiment, the sample comprises a bacterial membrane or a fragment thereof, preferably wherein said fragment comprises a non-bacterial membrane lipid component. In a preferable embodiment, the sample comprises a bacterial membrane lipid present as an integral part of the bacterial membrane or a fragment thereof in the sample.

In one embodiment, the sample may comprise (e.g. further comprise) at least one non-lipid and/or non-bacterial membrane component of a bacterial cell. For example, the sample may comprise a protein, a lipopolysaccharide and/or a nucleic acid of a bacterial cell.

In a preferable embodiment, the sample is an impure sample. The term "impure sample" may be used synonymously with the term "unpurified sample" or "crude" sample.

An impure sample has not been purified to extract a bacterial lipid (e.g. a bacterial membrane lipid) such that the lipid is provided in a pure form prior to subjecting the sample to mass spectrometry analysis.

Suitably, the sample is not a purified sample of a bacterial lipid (e.g. a bacterial membrane lipid). The sample may be a 'crude' sample comprising intact bacteria (e.g. non-lysed bacteria).

For example, the impure sample may be a bacterial suspension, preferably wherein the bacteria of said bacterial suspension are intact (e.g. are not lysed).

An isolated sample obtainable from a subject may be used as a culture source, for example the isolated sample may be contacted with a bacterial culture medium and incubated to provide a bacterial culture. Suitable culture media and incubation times are described in the accompanying Examples.

In a preferable embodiment, a sample may be a culture of bacteria (a bacterial culture). For example, the sample may be a bacterial colony or bacterial suspension recovered from a bacterial growth medium. Said bacterial colony or suspension may be isolated (e.g. derived from) a clinical sample (e.g. a prepared or processed clinical sample). The skilled person understands that a bacterial colony or suspension may be derived from a sample from a subject, by contacting the (subject) sample with a suitable culture medium (e.g. Middlebrook 7H9 medium and/or Middlebrook 7H11 medium, optionally supplemented with oleic acid-albumin-dextrose-catalase). Another example of a suitable culture medium is McFarland (e.g. −5, −10, −20, −30 or −40, preferably −20) medium.

Alternatively, said colony or suspension may be isolated from an environmental sample (e.g. water, soil, and/or air sample).

Cardio-thoracic centres now routinely monitor heater-cooler devices (regularly employed during surgeries, particularly cardiothoracic surgery, to warm or cool patients as part of their care employed during) to look for bacterial (particularly mycobacterial) contamination (as such devices have been found to be the source of the organism) and ensure that they are safe to use in accordance with PHE and manufacturers guidance.

In one embodiment, the colony or suspension is isolated from a surgical device (preferably a heater-cooler device).

Advantageously, the utilisation of a sample comprising a bacterial membrane or a fragment thereof (e.g. a crude sample) in a method or use of the present invention avoids the need to purify lipid(s) (e.g. from large volumes of bacterial culture) prior to the detection of said lipid molecules by mass spectrometry. Thus, embodiments of the present invention may be distinguished from methods which require purification (e.g. pre-purification) of lipid (e.g. membrane lipid). By way of example, for the purification of the actual lipids, large amounts of culture (e.g. from 500 ml up to several litres) are required, and the global procedure may take up to 2 to 3 weeks (not compatible with clinical analysis).

The term "fragment" as used in the context of a bacterial membrane refers to a fragment comprising a non-lipid (e.g. non-bacterial membrane lipid) component, optionally in combination with a lipid (e.g. bacterial membrane lipid).

In one embodiment, said bacterial membrane is part of an intact bacterium. An "intact bacterium" is a bacterium which has not been lysed (e.g. not subjected to chemical and/or mechanical lysis typically used prior to purifying a component such as a lipid or a protein from bacteria).

In a preferable embodiment, the sample comprises a bacterial membrane lipid present as an integral component of a bacterial membrane, or a fragment thereof, of an infectious bacterium.

In one embodiment, the sample is processed to remove salt. The reduced concentration of salt may allow the prevention of undesirable non-lipid species detection on a mass spectrum, thus improving the interpretability of the mass spectrum. Standard techniques for reducing the concentration of a salt (e.g. dialysis) are known in the art. In one embodiment, the sample is subjected to several rounds of washing (e.g. centrifuging and resuspension in a low salt buffer or in a no salt buffer). A sample may comprise a salt concentration of less than 200 mM or 100 mM. Suitably, a sample may comprise a salt concentration of less than 50 mM, 30 mM or 10 mM.

The term "mass spectrometry analysis" encompasses any mass spectrometry technique suitable for the determination of the mass-to-charge ratio of a biological molecule, and may embraces negative and/or positive ion modes of mass spectrometry. Such mass spectrometry techniques include Matrix-assisted laser desorption/ionization time-of-flight mass spectrometry (MALDI-TOF MS), Surface Enhanced Laser Desorption Ionization time-of-flight mass spectrometry (SELDI-TOF MS), Accelerator Mass Spectrometry, Gas chromatography MS, liquid chromatography MS, Inductively coupled plasma MS, Isotope ratio mass spectrometry (IRMS), Rapid Evaporative Ionization Mass Spectrometry (REIMS), and Ion Mobility Spectrometry-MS. Preferably, mass spectrometry analysis comprises (or consists of) MALDI-TOF mass spectrometry.

Thus, a sample may be subjected to MALDI-TOF mass spectrometry analysis to generate a mass spectrum output in a method of the invention.

MALDI is an ionization technique used in mass spectrometry that typically uses a laser energy-absorbing matrix to create ions from large molecules (e.g. with minimal fragmentation), allowing the analysis of biomolecules (biopolymers such as DNA, proteins, peptides and sugars) and large organic molecules (such as polymers, dendrimers and other macromolecules), which tend to be fragile and fragment when ionized by other ionization methods.

In one embodiment, the matrix solution acts as a proton source to encourage ionization of the bacterial membrane lipid (e.g. the analyte).

In one embodiment, mass spectrometry analysis comprises the ionisation of an analyte. In one embodiment, mass spectrometry analysis comprises the ionisation of a bacterial membrane lipid (preferably a bacterial membrane lipid as an integral component of a bacterial membrane or fragment thereof).

The term "mass spectrum output" encompasses any data providing the mass-to-charge ratio (m/z) of a molecule (e.g. analyte) in a sample together with an estimation of the quantity/abundance of said molecule in a sample (by means of an intensity value). For example, an analyte may have an m/z across the range of 50 m/z to 40,000 m/z, 400 m/z to 30,000 m/z, 1,600 m/z to 2,200 m/z, 1,000-2,200 m/z or 1,000 m/z to 3,000 m/z. The experimental procedure of the invention may be optimised to selectively provide the m/z of a bacterial membrane lipid molecule with minimal background (e.g. where "background" is m/z data on non-lipid species).

The mass spectrum output may be obtained either within (i.e. constituting a step of) or external to the (i.e. not constituting a step of) methods of the invention. In one embodiment, the methods of the invention may comprise a step of obtaining a mass spectrum output, preferably by subjecting the sample to mass spectrometry analysis (e.g. in the positive and/or negative ion mode). In one embodiment, the mass spectrum is obtained externally to the method of the invention and accessed during the detection step of the invention.

The terms "subject", "individual" and "patient" are used interchangeably herein to refer to a mammalian subject. In one embodiment the "subject" is a human, a companion animal (e.g. a pet such as dogs, cats, and rabbits), livestock (e.g. pigs, sheep, cattle, and goats), and horses. In a preferable embodiment, the subject is a human.

In one embodiment, the subject may have one or more disorder selected from Cystic Fibrosis, Chronic Obstructive Pulmonary Disease (COPD), Bronchiectasis, gastro-oesophageal reflux disease (GORD), an immunodeficiency disorder (e.g. HIV), heart disease, or a combination thereof. In a preferable embodiment, the subject may have (e.g. suffer from) Cystic Fibrosis. In another preferable embodiment, the subject may comprise (e.g. suffer from) heart disease.

The inventors have advantageously found that the presence a peak set described herein may correlate with the presence of a *Mycobacterium*. This is particularly advantageous, given the pathogenicity of mycobacteria and the need to identify mycobacterial infections, especially for lung transplant candidates, candidates that have received cardiothoracic surgery (e.g. open-heart surgery).

*Mycobacterium* is a genus of Actinobacteria bacterium, and is involved in a multitude of infectious diseases such as tuberculosis (TB), for which *Mycobacterium* tuberculosis (including the sub-species *M. tuberculosis, M bovis*) is the causative agent. However, the genus *Mycobacterium* encompasses almost 200 species, including the non-tuberculosis mycobacteria (NTM), many of which are opportunistic human or mammalian pathogens (e.g. they cause infection typically in patients who are compromised by underlying illness, or are immunologically deficient in some way). A number of these NTM species, such as *M. kansasii, M. avium, M. xenopi*, and *M. marinum* are associated with human illness/infection, particularly in immunocompromised subjects, or subjects undergoing (or having undergone) cardiothoracic surgery. The NTM *M. chimaera* is particularly problematic in the latter.

The term "*Mycobacterium*" as used herein refers to any species of the genus *Mycobacterium*. A *Mycobacterium* may be an intact bacterium or a fragmented bacterium. The bacterium may have been subjected to any chemical (e.g. treatment with alkaline agents) or physical treatment (e.g. heating, vortexing or pipetting).

In a preferable embodiment, said one or more peak set may be indicative of the presence of a *Mycobacterium*.

Thus, the invention further encompasses methods for detecting the presence or absence of a *Mycobacterium*.

All embodiments and definitions as described herein are applicable to each method, use and kit described herein. Thus, all embodiments and definitions described herein in the context of "a method for identifying a subject suitable for receiving a lung transplant" and "a method for identifying the presence or absence of a bacterial infection in a subject subsequent to receiving open heart surgery and/or a heart transplant" are equally applicable to "methods for detecting the presence or absence of a *Mycobacterium*" (and vice versa).

Advantageously, methods of the invention may allow detection of an infection with *M. abscessus* (which is considered to be a contradiction to lung transplantation by the International Society of Heart and Lung Transplantation). This is particularly important where there is progressive NTM pulmonary disease despite optimal antibiotic therapy (where the disease/infection is even more likely to be considered to be a contraindication for lung transplantation).

The detection of *M. chimaera* (part of the *M. avium-intracellulare* complex) is advantageous, as this bacterium is particularly harmful to subjects undergoing or have undergone heart surgery).

In one aspect, there is provided a method for detecting the presence or absence of a *Mycobacterium* (e.g. in a sample), the method comprising:

a. subjecting a sample to mass spectrometry analysis in the positive ion mode and generating a mass spectrum output; and b. detecting one or more peak set in said mass spectrum output (e.g. one or more peak set indicative of the presence of a *Mycobacterium*);

c. wherein said one or more peak set is selected from:

i. a fourth peak set comprising at least two defined peaks (for example, at least three, four, or five defined peaks) selected from: a peak having a m/z of from 1012-1015 m/z (preferably about 1013.2 m/z), a peak having a m/z of from 1121-1124 m/z (preferably about 1122.8 m/z), a peak having a m/z of from 1122-1125 m/z (preferably about 1123.8 m/z), a peak having an m/z of from 1123-1126 m/z (preferably about 1124.8 m/z), and a peak having a m/z of from 1149-1152 m/z (preferably about 1150.9 m/z);

ii. a fifth peak set comprising at least two defined peaks (for example, at least three, four, or five defined peaks) selected from: a peak having a m/z of from 1311-1314 m/z (preferably about 1312.8 m/z), a peak having a m/z of from 1339-1342 m/z (preferably about 1340.8 m/z), a peak having a m/z of from 1474-1477 m/z (preferably about 1475.8 m/z), a peak having a m/z of from 1488-1491 m/z (preferably about 1489.8 m/z), and a peak having a m/z of from 1823-1826 m/z (preferably about 1824 m/z);

iii. a seventh peak set comprising at least two defined peaks (for example, at least three, or four defined peaks) selected from: a peak having a m/z of from 1294-1297 m/z (preferably about 1295.9 m/z), a peak having a m/z of from 1296-1299 m/z (preferably about 1297.9 m/z), a peak having a m/z of from 1308-1311 m/z (preferably about 1309.9 m/z), and a peak having a m/z of from 1322-1325 m/z (preferably about 1323.9 m/z);

iv. an eighth peak set comprising at least two defined peaks selected from: a peak having a m/z of from 1370-1373 m/z (preferably about 1371 m/z), and a peak having a m/z of from 1412-1415 m/z (preferably about 1413 m/z);

v. a ninth peak set comprising at least two defined peaks (for example, at least three, or four defined peaks) selected from: a peak having a m/z of from 2129-2132 m/z (preferably about 2130.4 m/z), a peak having a m/z of from 2171-2174 m/z (preferably about 2172.4 m/z), a peak having a m/z of from 2247-2250 m/z (preferably about 2248.5 m/z), and a peak having a m/z of from 2261-2264 m/z (preferably about 2262.5 m/z);

vi. a tenth peak set comprising at least two defined peaks (for example, at least three, or four defined peaks) selected from: a peak having a m/z of from 2273-2276 m/z (preferably about 2274.1 m/z), a peak having a m/z of from 2275-2278 m/z (preferably about 2276.1 m/z), a peak having a m/z of from 2551-2554 m/z (preferably about 2552.2 m/z), and a peak having a m/z of from 2553-2556 m/z (preferably about 2554.2 m/z);

vii. an eleventh peak set comprising at least two defined peaks (for example, at least three, or four defined peaks) selected from: a peak having a m/z of from 1339-1342 m/z (preferably about 1340.8 m/z), a peak having a m/z of from 1353-1356 m/z (preferably about 1354.8 m/z), a peak having a m/z of from 1367-1370 m/z (preferably about 1368.8 m/z), and a peak having an m/z of from 1381-1384 m/z (preferably about 1382.8 m/z);

viii. a twelfth peak set comprising at least two defined peaks (for example, at least three, or four defined peaks) selected from: a peak having an m/z of from 1242-1245 m/z (preferably about 1243.7 m/z), a peak having an m/z of from 1256-1259 m/z (preferably about 1257.7 m/z), a peak having an m/z of from 1270-1273 m/z (preferably about 1271.7 m/z), and a peak having an m/z of from 1298-1301 m/z (preferably about 1299.7 m/z);

ix. a fifteenth peak set comprising at least two defined peaks (for example, at least three, or four defined peaks) selected from: a peak having an m/z of from 1202-1205 m/z (preferably about 1203.6 m/z), a peak having an m/z of from 1224-1227 m/z (preferably about 1225.6 m/z), a peak having an m/z of from 1226-1229 m/z (preferably about 1227.6 m/z), and a peak having an m/z of from 1240-1243 m/z (preferably about 1241.6 m/z);

x. a seventeenth peak set comprising at least two defined peaks (for example, at least three, or four defined peaks) selected from: a peak having an m/z of from 1308-1311 m/z (preferably about 1309.9 m/z), a peak having an m/z of from 1310-1313 m/z (preferably about 1311.9 m/z), a peak having an m/z of from 1324-1327 m/z (preferably about 1325.9 m/z), and a peak having an m/z of from 1338-1341 m/z (preferably about 1339.9 m/z);

xi. an eighteenth peak set comprising at least two defined peaks (for example, at least three, or four defined peaks) selected from: a peak having an m/z of from 1012-1015 m/z (preferably about 1013.3 m/z), a peak having an m/z of from 1028-1031 m/z (preferably about 1029.3 m/z), a peak having an m/z of from 1697-1700 m/z (preferably about 1698.2 m/z), and a peak having an m/z of from 1698-1701 m/z (preferably about 1699.2 m/z);

xii. a nineteenth peak set comprising at least two defined peaks selected from: a peak having an m/z of from 1226-1229 m/z (preferably about 1227.9 m/z), and a peak having an m/z of from 1240-1243 m/z (preferably about 1241.9 m/z);

xiii. a twenty-first peak set comprising at least two defined peaks (for example, at least three, four, or five defined peaks) selected from: a peak having an m/z of from 1036-1039 m/z (preferably about 1037.5 m/z), a peak having an m/z of from 1259-1262 m/z (preferably about 1260.3 m/z), a peak having an m/z of from 1374-1377 m/z (preferably about 1375.7 m/z), a peak having an m/z of from 2497-2500 m/z (preferably about 2498.7 m/z), and a peak having an m/z of from 2835-2838 m/z (preferably about 2837 m/z);

xiv. a twenty-second peak set comprising at least two defined peaks (for example, at least three, four, or five defined peaks) selected from: a peak having an m/z of from 1057-1060 m/z (preferably about 1058.6 m/z), a peak having an m/z of from 1498-1501 m/z (preferably about 1499.7 m/z), a peak having an m/z of from 1512-1515 m/z (preferably about 1513.7 m/z), and a peak having an m/z of from 1526-1529 m/z (preferably about 1527.7 m/z);

xv. a twenty-fourth peak set comprising at least two defined peaks (for example, at least three, or four defined peaks) selected from: a peak having an m/z of from 1242-1245 m/z (preferably about 1243.6 m/z), a peak having an m/z of from 1256-1259 m/z (preferably about 1257.7 m/z), a peak having an m/z of from 1270-1273 m/z (preferably about 1271.7 m/z), and a peak having an m/z of from 1284-1287 m/z (preferably about 1285.7 m/z); and xvi. a twenty-fifth peak set comprising at least two defined peaks (for example, at least three, or four defined peaks) selected from: a peak having an m/z of from 1242-1245 m/z (preferably about 1243.6 m/z), a peak having an m/z of from 1256-1259 m/z (preferably about 1257.6 m/z), a peak having an m/z of from 1270-1273 m/z (preferably about 1271.7), and a peak having an m/z of from 1284-1287 m/z (preferably about 1285.7);

d. wherein the presence of said one or more peak set indicates the presence of a *Mycobacterium*, and/or indicates the presence of a mycobacterial infection; and e. wherein the absence of said one or more peak set indicates the absence of a *Mycobacterium*, and/or indicates the absence of a mycobacterial infection.

In one embodiment, the methods of the invention may further comprise administering to a subject a therapy (preferably a therapy for a mycobacterial infection, such as an appropriate antibiotic) wherein the presence of said one or more peak set is detected.

The methods may further comprise, subsequent to administering said therapy, a subsequent detecting step for detecting the presence or absence of said one or more peak set in a mass spectrum output obtainable by means of subjecting an isolated sample from said subject to mass spectrometry analysis. In one embodiment, the absence of said one or more peak set following said therapy indicates that the subject is (e.g. has been rendered by therapy) a suitable candidate for receiving a lung transplant (and/or does not comprise a bacterial infection, such as a mycobacterial infection). In one embodiment, the presence of said one or more peak set following said therapy indicates that the subject is not (e.g. has not been rendered by therapy) a suitable candidate for receiving a lung transplant (and/or does comprise a bacterial infection, such as a mycobacterial infection).

In one embodiment of a method described herein (e.g. a method for identifying a subject suitable for receiving a lung transplant, a method for identifying the presence or absence of a bacterial infection in a subject subsequent to receiving open heart surgery and/or a heart transplant, and/or a method for detecting the presence or absence of a *Mycobacterium*):

a. the presence of the first peak set is indicative of the presence of *M. abscessus;* b. the presence of the second peak set is indicative of the presence of *M. tuberculosis* (preferably *M. tuberculosis* H37Rv);

c. the presence of the third peak set is indicative of the presence of *M. avium;* d. the presence of the fourth peak set is indicative of the presence of *M. bohemicum;* e. the presence of the fifth peak set is indicative of the presence of *M. celatum;* f. the presence of the sixth peak set is indicative of the presence of *M. chelonae;* g. the presence of the seventh peak set is indicative of the presence of *M. chimaera;* h. the presence of the eighth peak set is indicative of the presence of *M. fortuitum;* i. the presence of the ninth peak set is indicative of the presence of *M. gordonae;* j. the presence of the tenth peak set is indicative of the presence of *M. interjectum;* k. the presence of the eleventh peak set is indicative of the presence of *M. intermedium;* l. the presence of the twelfth peak set is indicative of the presence of *M. intracellulare;* m. the presence of the thirteenth peak set is indicative of the presence of *M. kansasii;* n. the presence of the fourteenth peak set is indicative of the presence of *M. marinum;* o. the presence of the fifteenth peak set is indicative of the presence of *M. nonchromogenicum;* p. the presence of the sixteenth peak set is indicative of the presence of *M. peregrinum;* q. the presence of the seventeenth peak set is indicative of the presence of *M. scrofulaceum;* r. the presence of the eighteenth peak set is indicative of the presence of *M. shimoidei;* s. the presence of the nineteenth peak set is indicative of the presence of *M. simiae;* t. the presence of the twentieth peak set is indicative of the presence of *M. smegmatis;* u. the presence of the twenty-first peak set is indicative of the presence of *M. szulgai;* v. the presence of the twenty-second peak set is indicative of the presence of *M. ulcerans;* w. the presence of the twenty-third peak set is indicative of the presence of *M. xenopi;* x. the presence of the twenty-fourth peak set is indicative of the presence of *M. bollettii;* y. the presence of the twenty-fifth peak set is indicative of the presence of *M. massiliense;* z. the presence of the twenty-sixth peak set is indicative of the presence of *M. chimaera*; (preferably *M. chimaera* 13044, obtainable from the Belgian Co-ordinated Collections of Microorganisms (BCCM));

aa. the presence of the twenty-seventh peak set is indicative of the presence of *M. chimaera* (preferably *M. chimaera* 2015-01546, obtainable from the BCCM);

bb. the presence of the twenty-eighth peak set is indicative of the presence of *M. fortuitum* (preferably *M. fortuitum* 52847, obtainable from the BCCM);

cc. the presence of the twenty-ninth peak set is indicative of the presence of *M. fortuitum* (preferably *M. fortuitum*, obtainable from the European Centres for Disease Control (ECDC));

dd. the presence of the thirtieth peak set is indicative of the presence of *M. intracellulare* (preferably *M. intracellulare* 52847, obtainable from the ECDC);

ee. the presence of the thirty-first peak set is indicative of the presence of *M. intracellulare* (preferably *M. intracellulare* 120584, obtainable from the BCCM);

ff. the presence of the thirty-second peak set is indicative of the presence of *M. peregrinum* (preferably *M. peregrinum* 970462, obtainable from the BCCM);

gg. the presence of the thirty-third peak set is indicative of the presence of *M. peregrinum* (preferably *M. peregrinum*, obtainable from the ECDC);

hh. the presence of the thirty-fourth peak set is indicative of the presence of *M. scrofulaceum* (preferably *M. scrofulaceum* C01934, obtainable from the BCCM);

ii. the presence of the thirty-fifth peak set is indicative of the presence of *M. scrofulaceum* (preferably *M. scrofulaceum*, obtainable from the ECDC);

jj. the presence of the thirty-sixth peak set is indicative of the presence of *M. simiae* (preferably *M. simiae* C02428, obtainable from the BCCM);

kk. the presence of the thirty-seventh peak set is indicative of the presence of *M. simiae* (preferably *M. simiae*, obtainable from the ECDC);

ll. the presence of said thirty-eighth peak set is indicative of the presence of *M. tuberculosis* (preferably *M. tuberculosis* H37Rv);

mm. the presence of said thirty-ninth peak set is indicative of the presence of *M. avium* (preferably *M. avium* serovar 4);

nn. the presence of said fortieth peak set is indicative of the presence of *M. peregrinum;* oo. the presence of said fortieth peak set is indicative of the presence of *M. abscessus* (preferably *M. abscessus* subsp. *abscessus*);

pp. the presence of said forty-second peak set is indicative of the presence of *M. bolletii* (e.g. *M. abscessus* subsp. *bolletii*); and/or qq. the presence of said forty-third peak set is indicative of the presence of *M. massiliense* (e.g. *M. abscessus* subsp. *massiliense*).

A number of the peaks described herein have been found to exhibit particularly good intensity (e.g. abundance) in a mass spectrum output, and are thus particularly advantageous peaks of said peak set. Preferably, the at least two peaks of a peak set of the invention comprise a relative intensity (an intensity ratio value) of at least 50%, more preferably at least 75% (e.g. wherein the relative intensity means the intensity of the peak relative to the most intense peak in the mass spectrum output).

Further embodiments in relation to any peak set described herein are provided below.

In one embodiment, said first peak set comprises at least two (preferably at least three) defined peaks selected from: a peak having a m/z of from 1284-1287 m/z (preferably about 1285.9 m/z), a peak having a m/z of from 1402-1405 m/z (preferably about 1403.9 m/z), and a peak having a m/z of from 1430-1433 m/z (preferably about 1431.9 m/z); preferably a peak having a m/z of from 1402-1405 m/z (preferably about 1403.9 m/z) and a peak having a m/z of from 1430-1433 m/z (preferably about 1431.9 m/z).

In one embodiment, said second peak set comprises at least two (preferably at least three) defined peaks selected from: a peak having a m/z of from 1220-1223 m/z (preferably about 1221.9 m/z), a peak having a m/z of from 1459-1462 m/z (preferably about 1460.2 m/z), and a peak having a m/z of from 1739-1742 m/z (preferably about 1740.5 m/z); preferably a peak having a m/z of from 1220-1223 m/z (preferably about 1221.9 m/z), and a peak having a m/z of from 1459-1462 m/z (preferably about 1460.2 m/z).

In one embodiment, said third peak set comprises at least two (preferably at least three; more preferably at least four) defined peaks selected from: a peak having a m/z of from 1242-1245 m/z, a peak having a m/z of from 1280-1283 m/z, and a peak having a m/z of from 1294-1297 m/z (preferably a peak having a m/z of from 1242-1245 m/z and a peak having a m/z of from 1294-1297 m/z).

In one embodiment, said fourth peak set comprises at least two (preferably at least three; more preferably at least four) defined peaks selected from: a peak having a m/z of from 1012-1015 m/z, a peak having a m/z of from 1121-1124 m/z, a peak having a m/z of from 1122-1125 m/z, and a peak having an m/z of from 1123-1126 m/z (preferably a peak having a m/z of from 1012-1015 m/z, and a peak having a m/z of from 1121-1124 m/z).

In one embodiment, said fifth peak set comprises at least two (preferably at least three; more preferably at least four) defined peaks selected from: a peak having a m/z of from 1339-1342 m/z, a peak having a m/z of from 1488-1491 m/z, and a peak having a m/z of from 1823-1826 m/z (preferably a peak having a m/z of from 1339-1342 m/z, and a peak having a m/z of from 1488-1491 m/z, and a peak having a m/z of from 1823-1826 m/z).

In one embodiment, said sixth peak pet comprises at least two (preferably at least three; more preferably at least four) defined peaks selected from: a peak having a m/z of from 1242-1245 m/z, a peak having a m/z of from 1256-1259 m/z, and a peak having a m/z of from 1318-1321 m/z (preferably a peak having a m/z of from 1242-1245 m/z, a peak having a m/z of from 1256-1259 m/z).

In one embodiment, said seventh peak set comprises at least two (preferably at least three; more preferably at least four) defined peaks selected from: a peak having a m/z of from 1294-1297 m/z, a peak having a m/z of from 1296-1299 m/z, and a peak having a m/z of from 1322-1325 m/z (preferably a peak having a m/z of from 1294-1297 m/z, and a peak having a m/z of from 1322-1325 m/z).

In one embodiment, said ninth peak set comprises at least two (preferably at least three; more preferably at least four) defined peaks selected from: a peak having a m/z of from 2129-2132 m/z, a peak having a m/z of from 2171-2174 m/z, and a peak having a m/z of from 2261-2264 m/z (preferably a peak having a m/z of from 2171-2174 m/z, and a peak having a m/z of from 2261-2264 m/z).

In one embodiment, said tenth peak set comprises at least two (preferably at least three; more preferably at least four) defined peaks selected from: a peak having a m/z of from 2273-2276 m/z, a peak having a m/z of from 2275-2278 m/z, and a peak having a m/z of from 2553-2556 m/z (preferably a peak having a m/z of from 2273-2276 m/z, a peak having a m/z of from 2275-2278 m/z).

In one embodiment, said eleventh peak set comprises at least two (preferably at least three; more preferably at least four) defined peaks selected from: a peak having a m/z of from 1353-1356 m/z, a peak having a m/z of from 1367-1370 m/z, and a peak having an m/z of from 1381-1384 m/z (preferably a peak having a m/z of from 1353-1356 m/z, and a peak having an m/z of from 1381-1384 m/z).

In one embodiment, said twelfth peak set comprises at least two (preferably at least three; more preferably at least four) defined peaks selected from: a peak having an m/z of from 1242-1245 m/z, a peak having an m/z of from 1256-1259 m/z, and a peak having an m/z of from 1270-1273 m/z (preferably a peak having an m/z of from 1242-1245 m/z and a peak having an m/z of from 1270-1273 m/z).

In one embodiment, said thirteenth peak set comprises at least two (preferably at least three; more preferably at least four) defined peaks selected from: a peak having an m/z of from 1458-1461 m/z, a peak having an m/z of from 2718-2721 m/z, and a peak having an m/z of from 2760-2763 m/z (preferably a peak having an m/z of from 1458-1461 m/z, a peak having an m/z of from 2718-2721 m/z).

In one embodiment, said fourteenth peak set comprises at least two (preferably at least three; more preferably at least four) defined peaks selected from: a peak having an m/z of from 1172-1175 m/z, a peak having an m/z of from 1174-1177 m/z, and a peak having an m/z of from 1909-1912 m/z (preferably a peak having an m/z of from 1172-1175 m/z, and a peak having an m/z of from 1174-1177 m/z).

In one embodiment, said fifteenth peak set comprises at least two (preferably at least three; more preferably at least four) defined peaks selected from: a peak having an m/z of from 1224-1227 m/z, a peak having an m/z of from 1226-1229 m/z, and a peak having an m/z of from 1240-1243 m/z (preferably a peak having an m/z of from 1226-1229 m/z, and a peak having an m/z of from 1240-1243 m/z).

In one embodiment, said sixteenth peak set comprises at least two (preferably at least three; more preferably at least four) defined peaks selected from: a peak having an m/z of from 1318-1321 m/z, a peak having an m/z of from 1332-1335 m/z, and a peak having an m/z of from 1346-1349 m/z (preferably a peak having an m/z of from 1318-1321 m/z and a peak having an m/z of from 1346-1349 m/z).

In one embodiment, said seventeenth peak set comprises at least two (preferably at least three; more preferably at least four) defined peaks selected from: a peak having an m/z of from 1310-1313 m/z, a peak having an m/z of from 1324-1327 m/z, and a peak having an m/z of from 1338-1341 m/z (preferably a peak having an m/z of from 1310-1313 m/z, and a peak having an m/z of from 1324-1327 m/z).

In one embodiment, said eighteenth peak set comprises at least two (preferably at least three; more preferably at least four) defined peaks selected from: a peak having an m/z of from 1012-1015 m/z, a peak having an m/z of from 1028-1031 m/z, and a peak having an m/z of from 1698-1701 m/z (preferably a peak having an m/z of from 1012-1015 m/z, and a peak having an m/z of from 1028-1031 m/z).

In one embodiment, said twentieth peak set comprises at least two (preferably at least three; more preferably at least four) defined peaks selected from: a peak having an m/z of from 1414-1417 m/z, a peak having an m/z of from 1443-1446 m/z, and a peak having an m/z of from 1543-1546 m/z (preferably a peak having an m/z of from 1443-1446 m/z, and a peak having an m/z of from 1543-1546 m/z).

In one embodiment, said twenty-first peak set comprises at least two (preferably at least three; more preferably at least four) defined peaks selected from: a peak having an m/z of from 1259-1262 m/z, a peak having an m/z of from 2497-2500 m/z, and a peak having an m/z of from 2835-2838 m/z (preferably a peak having an m/z of from 2497-2500 m/z, and a peak having an m/z of from 2835-2838 m/z).

In one embodiment, said twenty-second peak set comprises at least two (preferably at least three; more preferably at least four) defined peaks selected from: a peak having an m/z of from 1057-1060 m/z, a peak having an m/z of from 1498-1501 m/z, and a peak having an m/z of from 1526-1529 m/z (preferably a peak having an m/z of from 1057-1060 m/z, and a peak having an m/z of from 1526-1529 m/z).

In one embodiment, said twenty-third peak set comprises at least two (preferably at least three; more preferably at least four) defined peaks selected from: a peak having an m/z of from 1432-1435 m/z, a peak having an m/z of from 1446-1449 m/z, and a peak having an m/z of from 1474-1477 m/z (preferably a peak having an m/z of from 1432-1435 m/z, and a peak having an m/z of from 1474-1477 m/z).

In one embodiment, said twenty-fourth peak set comprises at least two (preferably at least three; more preferably at least four) defined peaks selected from: a peak having an m/z of from 1242-1245 m/z, a peak having an m/z of from 1256-1259 m/z, and a peak having an m/z of from 1284-1287 m/z (preferably a peak having an m/z of from 1242-1245 m/z, and a peak having an m/z of from 1256-1259 m/z).

In one embodiment, said twenty-fifth peak set comprises at least two (preferably at least three; more preferably at least four) defined peaks selected from: a peak having an m/z of from 1242-1245 m/z, a peak having an m/z of from 1256-1259 m/z, and a peak having an m/z of from 1284-1287 m/z (preferably a peak having an m/z of from 1242-1245 m/z, and a peak having an m/z of from 1256-1259 m/z).

In one embodiment, the term "at least two" when used in the context of peak comprised in a peak set described herein means at least 2, 3, 4, 5, 6, 7, 8, 9, 10, or 11, of the peaks. In one embodiment, the term "at least two" when used in the context of peak comprised in a peak set described herein means at least 2, 3, 4, 5 of the peaks.

In a preferred embodiment, the term "at least two" when used in the context of peak comprised in a peak set described herein means at least three of the peaks.

In one embodiment, the term "at least two" when used in the context of peak comprised in a peak set described herein means all (e.g. a combination of each) of the peaks (e.g. all of the peaks subsequently recited).

The peak sets described herein may include one or more further defined peaks. The inclusion of additional peaks in the peak sets may lead to improved resolution in the detection of a suitable candidate for a lung transplant and/or detection of a bacterial infection and/or detection of a *Mycobacterium*, and greater confidence in the resulting decision of whether or not to conduct the procedure. Likewise, the detection of the presence or absence of a *Mycobacterium* may be improved.

Furthermore, the inventors have demonstrated that, within the *M. abscessus* complex (comprising three subspecies: *M. abscessus* subsp. *abscessus, M. abscessus* subsp. *massiliense*, and *M. abscessus* subsp. *bolletii*), the subspecies may be differentiated based on a unique lipid fingerprint (e.g. peak set). These species have different erm (41) gene patterns. This gene provides intrinsic resistance to macrolides, so the different patterns can lead to different treatment outcomes. Clarithromycin, amikacin, and cefoxitin are the current antimicrobial drugs of choice for treatment.

*M. abscessus* subsp. *bolletii* is recognized as a rare pathogen with a functional inducible erythromycin ribosome methyltransferase (erm) (41) gene. *M. abscessus* subsp. *massiliense* has been proposed to have a nonfunctional erm (41) gene, leading to macrolide susceptibility and a favorable treatment outcome for infections. The advancement of subspecies differentiation allows for more effective management of disease/infection caused by *M. abscessus* complex. For example, unlike *M. abscessus* subsp. *abscessus, M. abscessus* subsp. *massiliense* is understood not to have inducible resistance to clarithromycin. Therefore, knowing that a patient's infection is due to *M. abscessus* subsp. *massiliense* rather than one of the other two subspecies may enables confident administration of clarithromycin to treat the infection.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1210-1213 m/z (preferably about 1211.8 m/z), 1326-1329 m/z (preferably about 1327.8 m/z), 1356-1359 m/z (preferably about 1357.9 m/z), 1370-1373 m/z (preferably about 1371.9 m/z), 1384-1387 m/z (preferably about 1385.9 m/z), 1398-1401 m/z (preferably about 1399.9 m/z), 1400-1403 m/z (preferably about 1401.9 m/z), 1412-1415 m/z (preferably about 1413.9 m/z), 1414-1417 m/z (preferably about 1415.9 m/z), 1426-1429 m/z (preferably about 1427.9 m/z), 1428-1431 m/z (preferably about 1429.9 m/z), 1442-1445 m/z (preferably about 1443.9 m/z), 1444-1447 m/z (preferably about 1445.9 m/z), 1456-1459 m/z (preferably about 1457.9 m/z), 1458-1461 m/z (preferably about 1459.9 m/z), and/or 1472-1475 m/z (preferably about 1474 m/z);

a. wherein the presence of said one or more peak preferably confirms the presence of *M. abscessus* subsp. *abscessus*; and/or b. wherein the presence of said one or more peak indicates that the subject is not a suitable candidate for receiving a lung transplant; and/or c. wherein the presence of said one or more peak indicates that the operating theatre equipment is not suitable to be used during cardiothoracic surgery of a subject; and/or d. wherein the presence of said one or more peak is indicative of the presence of a bacterial infection in the subject subsequent to receiving cardiothoracic surgery.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1326-1329 m/z (preferably about 1327.8 m/z), 1400-1403 m/z (preferably about 1401.9 m/z), 1412-1415 m/z (preferably about 1413.9 m/z), 1414-1417 m/z (preferably about 1415.9 m/z), 1426-1429 m/z (preferably about 1427.9 m/z), 1428-1431 m/z (preferably about 1429.9 m/z), 1442-1445 m/z (preferably about 1443.9 m/z), 1444-1447 m/z (preferably about 1445.9 m/z), 1456-1459 m/z (preferably about 1457.9 m/z), 1458-1461 m/z (preferably about 1459.9 m/z), and/or 1472-1475 m/z (preferably about 1474 m/z);

a. wherein the presence of said one or more peak preferably confirms the presence of *M. abscessus* subsp. *abscessus*; and/or b. wherein the presence of said one or more peak indicates that the subject is not a suitable candidate for receiving a lung transplant; and/or c. wherein the presence of said one or more peak indicates that the operating theatre equipment is not suitable to be used during cardiothoracic surgery of a subject; and/or d. wherein the presence of said one or more peak is indicative of the presence of a bacterial infection in the subject subsequent to receiving cardiothoracic surgery.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1260-1263 m/z (preferably about 1261.9 m/z), 1262-1265 m/z (preferably about 1263.9 m/z), 1274-1277 m/z (preferably about 1275.9 m/z), 1276-1279 m/z (preferably about 1277.9 m/z), 1288-1291 m/z (preferably about 1289.9 m/z), 1290-1293 m/z (preferably about 1291.9 m/z), 1294-1297 m/z (preferably about 1295.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), 1338-1341 m/z (preferably about 1339.9 m/z), 1719-1722 m/z (preferably about 1720.1 m/z), 1735-1738 m/z (preferably about 1736.1 m/z), 1747-1750 m/z (preferably about 1748.1 m/z), 1761-1764 m/z (preferably about 1762.1 m/z), 1764-1767 m/z (preferably about 1765.1 m/z), and/or 1789-1792 m/z (preferably about 1790.1 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1260-1263 m/z (preferably about 1261.9 m/z), 1262-1265 m/z (preferably about 1263.9 m/z), 1274-1277 m/z (preferably about 1275.9 m/z), 1276-1279 m/z (preferably about 1277.9 m/z), 1288-1291 m/z (preferably about 1289.9 m/z), 1290-1293 m/z (preferably about 1291.9 m/z), 1294-1297 m/z (preferably about 1295.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), and/or 1338-1341 m/z (preferably about 1339.9 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1262-1265 m/z (preferably about 1263.9 m/z), 1308-1311 m/z (preferably about 1309.9 m/z), 1320-1323 m/z (preferably about 1321.9 m/z), 1719-1722 m/z (preferably about 1720.1 m/z), 1735-1738 m/z (preferably about 1736.1 m/z), 1747-1750 m/z (preferably about 1748.1 m/z), 1761-1764 m/z (preferably about 1762.1 m/z), 1764-1767 m/z (preferably about 1765.1 m/z), and/or 1789-1792 m/z (preferably about 1790.1 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the presence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1262-1265 m/z (preferably about 1263.9 m/z), 1308-1311 m/z (preferably about 1309.9 m/z), and/or 1320-1323 m/z (preferably about 1321.9 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the presence of one or more (preferably two or more) of the following (e.g. further) defined peak(s) in the mass spectrum output: a peak having a m/z of from 1072-1075 m/z (preferably about 1073.6 m/z) and/or 1262-1265 m/z (preferably about 1263.9 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the absence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1260-1263 m/z (preferably about 1261.9 m/z), 1262-1265 m/z (preferably about 1263.9 m/z), 1274-1277 m/z (preferably about 1275.9 m/z), 1276-1279 m/z (preferably about 1277.9 m/z), 1288-1291 m/z (preferably about 1289.9 m/z), 1290-1293 m/z (preferably about 1291.9 m/z), 1294-1297 m/z (preferably about 1295.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), 1338-1341 m/z (preferably about 1339.9 m/z), 1719-1722 m/z (preferably about 1720.1 m/z), 1735-1738 m/z (preferably about 1736.1 m/z), 1747-1750 m/z (preferably about 1748.1 m/z), 1761-1764 m/z (preferably about 1762.1 m/z), 1764-1767 m/z (preferably about 1765.1 m/z), and/or 1789-1792 m/z (preferably about 1790.1 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant; and/or c. wherein the absence of said one or more peak indicates that the operating theatre equipment is not suitable to be used during cardiothoracic surgery of a subject; and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the absence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1260-1263 m/z (preferably about 1261.9 m/z), 1262-1265 m/z (preferably about 1263.9 m/z), 1274-1277 m/z (preferably about 1275.9 m/z), 1276-1279 m/z (preferably about 1277.9 m/z), 1288-1291 m/z (preferably about 1289.9 m/z), 1290-1293 m/z (preferably about 1291.9 m/z), 1294-1297 m/z (preferably about 1295.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), and/or 1338-1341 m/z (preferably about 1339.9 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant; and/or c. wherein the absence of said one or more peak indicates that the operating theatre equipment is not suitable to be used during cardiothoracic surgery of a subject; and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the absence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1262-1265 m/z (preferably about 1263.9 m/z), 1308-1311 m/z (preferably about 1309.9 m/z), 1320-1323 m/z (preferably about 1321.9 m/z), 1719-1722 m/z (preferably about 1720.1 m/z), 1735-1738 m/z (preferably about 1736.1 m/z), 1747-1750 m/z (preferably about 1748.1 m/z), 1761-1764 m/z (preferably about 1762.1 m/z), 1764-1767 m/z (preferably about 1765.1 m/z), and/or 1789-1792 m/z (preferably about 1790.1 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant; and/or c. wherein the absence of said one or more peak indicates that the operating theatre equipment is not suitable to be used during cardiothoracic surgery of a subject; and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the absence of one or more (preferably two or more; more preferably three or more) of the following (e.g. further) defined peak(s) in the mass spectrum output: a peak having a m/z of from 1072-1075 m/z (preferably about 1073.6 m/z), 1248-1251 m/z (preferably about 1249.9 m/z), 1262-1265 m/z (preferably about 1263.9 m/z), 1308-1311 m/z (preferably about 1309.9 m/z), and/or 1320-1323 m/z (preferably about 1321.9 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant; and/or c. wherein the absence of said one or more peak indicates that the operating theatre equipment is not suitable to be used during cardiothoracic surgery of a subject; and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the positive ion mode, and a method of the invention may further comprise confirming the absence of one or more (preferably two or more) of the following (e.g. further) defined peak(s) in the mass spectrum output: a peak having a m/z of from 1072-1075 m/z (preferably about 1073.6 m/z) and/or 1262-1265 m/z (preferably about 1263.9 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant; and/or c. wherein the absence of said one or more peak indicates that the operating theatre equipment is not suitable to be used during cardiothoracic surgery of a subject; and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and a method of the invention may further comprise confirming the presence of one or more (preferably two or more) of the following (e.g. further) defined peak(s) in the mass spectrum output: a peak having a m/z of from 681-684 m/z (preferably about 682 m/z) and/or 696-699 m/z (preferably about 697 m/z);

a. wherein the presence of said one or more peak preferably confirms the presence of *M. abscessus* subsp. *abscessus*; and/or b. wherein the presence of said one or more peak indicates that the subject is not a suitable candidate for receiving a lung transplant; and/or c. wherein the presence of said one or more peak indicates that the operating theatre equipment is not suitable to be used during cardiothoracic surgery of a subject; and/or d. wherein the presence of said one or more peak is indicative of the presence of a bacterial infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the presence of one or more (preferably two or more; more preferably three or more) of the following (e.g. further) defined peak(s) in the mass spectrum output: a peak having a m/z of from 408-411 m/z (preferably about 409 m/z), 490-493 m/z (preferably about 491 m/z), and/or 512-515 m/z (preferably about 513 m/z);

a. wherein the presence of said one or more peak preferably confirms the presence of *M. abscessus* subsp. *massiliense*; and/or b. optionally wherein the presence of said one or more peak indicates that the subject is a suitable candidate for receiving a lung transplant if treated for an *M. abscessus* subsp. *massiliense* infection; and/or c. optionally wherein the presence of said one or more peak indicates that the operating theatre equipment is suitable to be used during cardiothoracic surgery (of a subject) if treated to remove *M. abscessus* subsp. *massiliense*; and/or d. wherein the presence of said one or more peak is indicative of the presence of a *M. abscessus* subsp. *massiliense* infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the presence of the following (e.g. further) defined peak(s) in the mass spectrum output: a peak having a m/z of from 408-411 m/z (preferably about 409 m/z);

a. wherein the presence of said peak preferably confirms the presence of *M. abscessus* subsp. *massiliense*; and/or b. optionally wherein the presence of said peak indicates that the subject is a suitable candidate for receiving a lung transplant if treated for an *M. abscessus* subsp. *massiliense* infection; and/or c. optionally wherein the presence of said peak indicates that the operating theatre equipment is suitable to be used during cardiothoracic surgery (of a subject) if treated to remove *M. abscessus* subsp. *massiliense*; and/or d. wherein the presence of said peak is indicative of the presence of a *M. abscessus* subsp. *massiliense* infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the absence of one or more (preferably two or more; more preferably three or more) of the following (e.g. further) defined peak(s) in the mass spectrum output: a peak having a m/z of from 408-411 m/z (preferably about 409 m/z), 490-493 m/z (preferably about 491 m/z), and/or 512-515 m/z (preferably about 513 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant (e.g. if treated for an *M. abscessus* subsp. *massiliense* infection); and/or c. wherein the absence of said one or more peak indicates that the operating theatre equipment is not suitable to be used during cardiothoracic surgery (of a subject) (e.g. if treated to remove *M. abscessus* subsp. *massiliense*); and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the presence of the following (e.g. further) defined peak(s) in the mass spectrum output: a peak having a m/z of from 408-411 m/z (preferably about 409 m/z);

a. wherein the absence of said one or more peak preferably confirms the absence of *M. abscessus* subsp. *massiliense*; and/or b. wherein the absence of said one or more peak indicates that the subject is not a suitable candidate for receiving a lung transplant (e.g. if treated for an *M. abscessus* subsp. *massiliense* infection); and/or c. wherein the absence of said one or more peak indicates that the operating theatre equipment is not suitable to be used during cardiothoracic surgery (of a subject) (e.g. if treated to remove *M. abscessus* subsp. *massiliense*); and/or d. wherein the absence of said one or more peak is indicative of the absence of a *M. abscessus* subsp. *massiliense* infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the presence of one or more (preferably two or more; more preferably three or more) of the following (e.g. further) defined peak(s) in the mass spectrum output: a peak having a m/z of from 520-523 m/z (preferably about 521 m/z), 534-537 m/z (preferably about 535.9 m/z), 535-538 m/z (preferably about 536.9 m/z), 1403-1406 m/z (preferably about 1404 m/z), 1565-1568 m/z (preferably about 1566.9 m/z), 1568-1571 m/z (preferably about 1569 m/z), 1578-1581 m/z (preferably about 1579 m/z), 1581-1584 m/z (preferably about 1582 m/z), 1621-1624 m/z (preferably about 1622.1 m/z), 1623-1626 m/z (preferably about 1624.1 m/z), 1637-1640 m/z (preferably about 1638.1 m/z), 1638-1641 m/z (preferably about 1639.1 m/z), 1647-1650 m/z (preferably about 1648.1 m/z), 1648-1651 m/z (preferably about 1649.1 m/z), 1649-1652 m/z (preferably about 1650.1 m/z), 1663-1666 m/z (preferably about 1664.1 m/z), 1664-1667 m/z (preferably about 1665.1 m/z), 2296-2299 m/z (preferably about 2297.3 m/z), and/or 2297-2300 m/z (preferably about 2298.3 m/z);

a. wherein the presence of said one or more peak preferably confirms the presence of *M. abscessus* subsp. *bolletii*; and/or b. wherein the presence of said one or more peak indicates that the subject is not a suitable candidate for receiving a lung transplant; and/or c. wherein the presence of said one or more peak indicates that the operating theatre equipment is not suitable to be used during cardiothoracic surgery of a subject; and/or d. wherein the presence of said one or more peak is indicative of the presence of a bacterial infection in the subject subsequent to receiving cardiothoracic surgery.

In one embodiment, the sample is subjected to mass spectrometry in the negative ion mode (for example, additionally or alternatively to subjecting the sample to mass spectrometry in the positive ion mode), and method of the invention may further comprise confirming the presence of the following (e.g. further) defined peak(s) in the mass spectrum output: a peak having a m/z of from 1565-1568 m/z (preferably about 1566.9 m/z);

a. wherein the presence of said peak preferably confirms the presence of *M. abscessus* subsp. *bolletii*; and/or b. wherein the presence of said peak indicates that the subject is not a suitable candidate for receiving a lung transplant; and/or c. wherein the presence of said peak indicates that the operating theatre equipment is not suitable to be used during cardiothoracic surgery of a subject; and/or d. wherein the presence of said peak is indicative of the presence of a bacterial infection in the subject subsequent to receiving cardiothoracic surgery.

In one embodiment, said first peak set comprises one or more (preferably two or more; more preferably three or more) further peak having a m/z of from 1198-1201 m/z (preferably about 1199.8 m/z), 1200-1203 m/z (preferably about 1201.9 m/z), 1210-1213 m/z (preferably about 1211.9 m/z), 1212-1215 m/z (preferably about 1213.9 m/z), 1214-1217 m/z (preferably about 1215.9 m/z), 1224-1227 m/z (preferably about 1225.9 m/z), 1226-1229 m/z (preferably about 1227.9 m/z), 1228-1231 m/z (preferably about 1229.9 m/z), 1238-1241 m/z (preferably about 1239.9 m/z), 1240-1243 m/z (preferably about 1241.9 m/z), 1242-1245 m/z (preferably about 1243.9 m/z), 1252-1255 m/z (preferably about 1253.9 m/z), 1254-1257 m/z (preferably about 1255.9 m/z), 1266-1269 m/z (preferably about 1267.9 m/z), 1268-1271 m/z (preferably about 1269.9 m/z), 1270-1273 m/z (preferably about 1271.9 m/z), 1273-1276 m/z (preferably about 1274.9 m/z), 1280-1283 m/z (preferably about 1281.9 m/z), 1282-1285 m/z (preferably about 1283.9 m/z), 1296-1299 m/z (preferably about 1297.9 m/z), 1298-1301 m/z (preferably about 1299.9 m/z), 1300-1303 m/z (preferably about 1301.9 m/z), 1312-1315 m/z (preferably about 1313.9 m/z), 1326-1329 m/z (preferably about 1327.9 m/z), 1342-1345 m/z (preferably about 1343.9 m/z), 1344-1347 m/z (preferably about 1345.9 m/z), 1346-1349 m/z (preferably about 1347.9 m/z), 1356-1359 m/z (preferably about 1357.9 m/z), 1360-1363 m/z (preferably about 1361.9 m/z), 1370-1373 m/z (preferably about 1371.9 m/z), 1372-1375 m/z (preferably about 1373.9 m/z), 1374-1377 m/z (preferably about 1375.9 m/z), 1384-1387 m/z (preferably about 1385.9 m/z), 1386-1389 m/z (preferably about 1387.9 m/z), 1388-1391 m/z (preferably about 1389.9 m/z), 1398-1401 m/z (preferably about 1400 m/z), 1400-1403 m/z (preferably about 1401.9 m/z), 1412-1415 m/z (preferably about 1413.9 m/z), 1414-1417 m/z (preferably about 1415.9 m/z), 1415-1418 m/z (preferably about 1416.9 m/z), 1416-1419 m/z (preferably about 1417.9 m/z), 1427-1430 m/z (preferably about 1428 m/z), 1428-1431 m/z (preferably about 1430 m/z), 1429-1432 m/z (preferably about 1431 m/z), 1443-1446 m/z (preferably about 1444 m/z), 1444-1447 m/z (preferably about 1446 m/z), 1446-1449 m/z (preferably about 1448 m/z), 1457-1460 m/z (preferably about 1458 m/z), 1458-1461 m/z (preferably about 1460 m/z), 1473-1476 m/z (preferably about 1474 m/z), 1474-1477 m/z (preferably about 1475 m/z), or a combination thereof.

In one embodiment, said first peak set comprises one or more (preferably two or more; more preferably three or more) further peak having a m/z of from 1198-1201 m/z (preferably about 1199.8 m/z), 1200-1203 m/z (preferably about 1201.9 m/z), 1214-1217 m/z (preferably about 1215.9 m/z), 1224-1227 m/z (preferably about 1225.9 m/z), 1226-1229 m/z (preferably about 1227.9 m/z), 1228-1231 m/z (preferably about 1229.9 m/z), 1240-1243 m/z (preferably about 1241.9 m/z), 1252-1255 m/z (preferably about 1253.9 m/z), 1254-1257 m/z (preferably about 1255.9 m/z), 1268-1271 m/z (preferably about 1269.9 m/z), 1270-1273 m/z (preferably about 1271.9 m/z), 1273-1276 m/z (preferably about 1274.9 m/z), 1282-1285 m/z (preferably about 1283.9 m/z), 1298-1301 m/z (preferably about 1299.9 m/z), 1342-1345 m/z (preferably about 1343.9 m/z), 1344-1347 m/z (preferably about 1345.9 m/z), 1356-1359 m/z (preferably about 1357.9 m/z), 1372-1375 m/z (preferably about 1373.9 m/z), 1374-1377 m/z (preferably about 1375.9 m/z), 1386-1389 m/z (preferably about 1387.9 m/z), 1388-1391 m/z (preferably about 1389.9 m/z), 1415-1418 m/z (preferably about 1416.9 m/z), 1416-1419 m/z (preferably about 1417.9 m/z), 1429-1432 m/z (preferably about 1431 m/z), 1446-1449 m/z (preferably about 1448 m/z), 1474-1477 m/z (preferably about 1475 m/z), or a combination thereof.

In one embodiment, said first peak set comprises one or more (preferably two or more; more preferably three or more) further peak having a m/z of from 1198-1201 m/z (preferably about 1199.8 m/z), 1200-1203 m/z (preferably about 1201.9 m/z), 1214-1217 m/z (preferably about 1215.9 m/z), 1224-1227 m/z (preferably about 1225.9 m/z), 1226-1229 m/z (preferably about 1227.9 m/z), 1228-1231 m/z (preferably about 1229.9 m/z), 1240-1243 m/z (preferably about 1241.9 m/z), 1252-1255 m/z (preferably about 1253.9 m/z), 1254-1257 m/z (preferably about 1255.9 m/z), 1268-1271 m/z (preferably about 1269.9 m/z), 1270-1273 m/z (preferably about 1271.9 m/z), 1282-1285 m/z (preferably about 1283.9 m/z), 1298-1301 m/z (preferably about 1299.9 m/z), 1342-1345 m/z (preferably about 1343.9 m/z), 1356-1359 m/z (preferably about 1357.9 m/z), 1372-1375 m/z (preferably about 1373.9 m/z), 1374-1377 m/z (preferably about 1375.9 m/z), 1386-1389 m/z (preferably about 1387.9 m/z), 1388-1391 m/z (preferably about 1389.9 m/z), 1415-1418 m/z (preferably about 1416.9 m/z), 1429-1432 m/z (preferably about 1431 m/z), or a combination thereof.

In one embodiment, said second peak set comprises one or more (preferably two or more; more preferably three or more) further defined peak having a m/z of from 1025-1028 m/z (preferably about 1026.1 m/z), 1053-1056 m/z (preferably about 1054.2 m/z), 1081-1084 m/z (preferably about 1082.2 m/z), 1109-1112 m/z (preferably about 1110.3 m/z), 1178-1181 m/z (preferably about 1179.9 m/z), 1187-1190 m/z (preferably about 1188.4 m/z), 1206-1209 m/z (preferably about 1207.9 m/z), 1234-1237 m/z (preferably about 1235.9 m/z), 1236-1239 m/z (preferably about 1237.9 m/z), 1248-1251 m/z (preferably about 1249.9 m/z), 1259-1262 m/z (preferably about 1260.5 m/z), 1275-1278 m/z (preferably about 1276.5 m/z), 1287-1290 m/z (preferably about 1288.5 m/z), 1288-1291 m/z (preferably about 1289.6 m/z), 1301-1304 m/z (preferably about 1302.6 m/z), 1302-1305 m/z (preferably about 1303.6 m/z), 1303-1306 m/z (preferably about m/z), 1304-1307 m/z (preferably about 1305.6 m/z), 1445-1448 m/z (preferably about 1446.2 m/z), 1473-1476 m/z (preferably about 1474.2 m/z), 1475-1478 m/z (preferably about 1476.2 m/z), 1480-1483 m/z (preferably about 1481.8 m/z), 1487-1490 m/z (preferably about 1488.2 m/z), 1501-1504 m/z (preferably about 1502.3 m/z), 1517-1520 m/z (preferably about m/z), 1697-1700 m/z (preferably about 1698.5 m/z), 1699-1702 m/z (preferably about 1700.5 m/z), 1711-1714 m/z (preferably about 1712.5 m/z), 1713-1716 m/z (preferably about 1714.5 m/z), 1725-1728 m/z (preferably about 1726.5 m/z), 1753-1756 m/z (preferably about 1754.6 m/z), 1754-1757 m/z (preferably about 1755.6 m/z), 1755-1758 m/z (preferably about 1756.6 m/z), 1756-1759 m/z (preferably about 1757.6 m/z), 1767-1770 m/z (preferably about 1768.6 m/z), 2107-2110 m/z (preferably about 2108.6 m/z), or a combination thereof.

In one embodiment, said third peak set comprises one or more (preferably two or more; more preferably three or more) further peak having a m/z of from 1030-1033 m/z (preferably about 1031.6 m/z), 1210-1213 m/z (preferably about 1211.9 m/z), 1214-1217 m/z (preferably about 1215.9 m/z), 1218-1221 m/z (preferably about 1219.9 m/z), 1224-1227 m/z (preferably about 1225.9 m/z), 1225-1228 m/z (preferably about 1226.9 m/z), 1226-1229 m/z (preferably about 1227.9 m/z), 1228-1231 m/z (preferably about 1229.9 m/z), 1232-1235 m/z (preferably about 1233.9 m/z), 1234-1237 m/z (preferably about 1235.9 m/z), 1236-1239 m/z (preferably about 1237.9 m/z), 1238-1241 m/z (preferably about 1239.9 m/z), 1240-1243 m/z (preferably about 1241.9 m/z), 1245-1248 m/z (preferably about 1246.9 m/z), 1246-1249 m/z (preferably about 1274.9 m/z), 1248-1251 m/z (preferably about 1249.9 m/z), 1250-1253 m/z (preferably about 1251.9 m/z), 1252-1255 m/z (preferably about 1253.9 m/z), 1254-1257 m/z (preferably about 1255.9 m/z), 1256-1259 m/z (preferably about 1257.9 m/z), 1258-1261 m/z (preferably about 1259.9 m/z), 1260-1263 m/z (preferably about 1261.9 m/z), 1262-1265 m/z (preferably about 1263.9 m/z), 1263-1266 m/z (preferably about 1264.9 m/z), 1264-1267 m/z (preferably about 1265.9 m/z), 1266-1269 m/z (preferably about 1267.9 m/z), 1268-1271 m/z (preferably about 1269.9 m/z), 1270-1273 m/z (preferably about 1271.9 m/z), 1272-1275 m/z (preferably about 1273.9 m/z), 1273-1276 m/z (preferably about 1274.9 m/z), 1274-1277 m/z (preferably about 1275.9 m/z), 1282-1285 m/z (preferably about 1283.9 m/z), 1284-1287 m/z (preferably about 1285.9 m/z), 1285-1288 m/z (preferably about 1286.9 m/z), 1286-1289 m/z (preferably about 1287.9 m/z), 1296-1299 m/z (preferably about 1297.9 m/z), 1298-1301 m/z (preferably about 1299.9 m/z), 1308-1311 m/z (preferably about 1309.9 m/z), 1310-1313 m/z (preferably about 1311.9 m/z), 1312-1315 m/z (preferably about 1313.9 m/z), 1322-1325 m/z (preferably about 1323.9 m/z), 1324-1327 m/z (preferably about 1325.9 m/z), 1338-1341 m/z (preferably about 1339.9 m/z), 1368-1371 m/z (preferably about 1369.9 m/z), 1370-1373 m/z (preferably about 1371.9 m/z), 1384-1387 m/z (preferably about 1385.9 m/z), 1897-1900 m/z (preferably about 1898.2 m/z), 1909-1912 m/z (preferably about 1910.2 m/z), 1937-1940 m/z (preferably about 1938.3 m/z), 1939-1942 m/z (preferably about 1940.3 m/z), 1951-1954 m/z (preferably about 1952.3 m/z), 1954-1957 m/z (preferably about 1955.3 m/z), 1965-1968 m/z (preferably about 1966.3 m/z), 1967-1970 m/z (preferably about 1968.3 m/z), or a combination thereof.

In one embodiment, said fourth peak set comprises one or more (preferably two or more; more preferably three or more) further peak having a m/z of from 1021-1024 m/z (preferably about 1022.7 m/z), 1131-1134 m/z (preferably about 1132.9 m/z), 1134-1137 m/z (preferably about 1135.9 m/z), 1147-1150 m/z (preferably about 1148.9 m/z), 1150-1153 m/z (preferably about 1151.9 m/z), 1198-1201 m/z (preferably about 1199.7 m/z), 1878-1881 m/z (preferably about 1879.5 m/z), 1880-1883 m/z (preferably about 1881.5 m/z), 2131-2134 m/z (preferably about 2132 m/z), 2275-2278 m/z (preferably about 2276.3 m/z), 2553-2556 m/z (preferably about 2554.4 m/z), or a combination thereof.

In one embodiment, said fifth peak set comprises one or more (preferably two or more; more preferably three or more) further peak having a m/z of from 1253-1256 m/z (preferably about 1254.8 m/z), 1267-1270 m/z (preferably about 1268.8 m/z), 1269-1272 m/z (preferably about 1270.8 m/z), 1279-1282 m/z (preferably about 1280.8 m/z), 1281-

1284 m/z (preferably about 1282.8 m/z), 1283-1286 m/z (preferably about 1284.8 m/z), 1295-1298 m/z (preferably about 1296.8 m/z), 1297-1300 m/z (preferably about 1298.8 m/z), 1299-1302 m/z (preferably about 1300.8 m/z), 1300-1303 m/z (preferably about 1301.8 m/z), 1307-1310 m/z (preferably about 1308.8 m/z), 1309-1312 m/z (preferably about 1310.8 m/z), 1313-1316 m/z (preferably about 1314.8 m/z), 1323-1326 m/z (preferably about 1324.8 m/z), 1325-1328 m/z (preferably about 1326.8 m/z), 1327-1330 m/z (preferably about 1328.8 m/z), 1329-1332 m/z (preferably about 1330.8 m/z), 1341-1344 m/z (preferably about 1342.8 m/z), 1355-1358 m/z (preferably about 1356.8 m/z), 1357-1360 m/z (preferably about 1358.8 m/z), 1429-1432 m/z (preferably about 1430.8 m/z), 1432-1435 m/z (preferably about 1433.8 m/z), 1442-1445 m/z (preferably about 1443.9 m/z), 1443-1446 m/z (preferably about 1444.9 m/z), 1445-1448 m/z (preferably about 1446.8 m/z), 1446-1449 m/z (preferably about 1447.8 m/z), 1456-1459 m/z (preferably about 1457.9 m/z), 1457-1460 m/z (preferably about 1458.9 m/z), 1458-1461 m/z (preferably about 1459.9 m/z), 1460-1463 m/z (preferably about 1461.8 m/z), 1469-1472 m/z (preferably about 1470.9 m/z), 1471-1474 m/z (preferably about 1472.9 m/z), 1472-1475 m/z (preferably about 1473.8 m/z), 1477-1480 m/z (preferably about 1478.8 m/z), 1484-1487 m/z (preferably about 1485.8 m/z), 1485-1488 m/z (preferably about 1486.9 m/z), 1486-1489 m/z (preferably about 1487.8 m/z), 1497-1500 m/z (preferably about 1498.9 m/z), 1499-1502 m/z (preferably about 1500.9 m/z), 1500-1503 m/z (preferably about 1501.9 m/z), 1502-1505 m/z (preferably about 1503.9 m/z), 1513-1516 m/z (preferably about 1514.9 m/z), 1514-1517 m/z (preferably about 1515.9 m/z), 1516-1519 m/z (preferably about 1517.9 m/z), 1518-1521 m/z (preferably about 1519.8 m/z), 1528-1531 m/z (preferably about 1529.9 m/z), 1529-1532 m/z (preferably about 1530.9 m/z), 1530-1533 m/z (preferably about 1531.9 m/z), 1766-1769 m/z (preferably about 1768 m/z), 1781-1784 m/z (preferably about 1782 m/z), 1795-1798 m/z (preferably about 1796 m/z), 1809-1812 m/z (preferably about 1810 m/z), 1811-1814 m/z (preferably about 1812 m/z), 1815-1818 m/z (preferably about 1816.1 m/z), 1821-1824 m/z (preferably about 1822 m/z), 1829-1832 m/z (preferably about 1830.1 m/z), 1837-1840 m/z (preferably about 1838 m/z), 1839-1842 m/z (preferably about 1840 m/z), 1849-1852 m/z (preferably about 1850 m/z), 1851-1854 m/z (preferably about 1852 m/z), or a combination thereof.

In one embodiment, said sixth peak set comprises one or more (preferably two or more; more preferably three or more) further peak having a m/z of from 1127-1130 m/z (preferably about 1128.5 m/z), 1140-1143 m/z (preferably about 1141.7 m/z), 1144-1147 m/z (preferably about 1145.7 m/z), 1158-1161 m/z (preferably about 1159.7 m/z), 1168-1171 m/z (preferably about 1169.8 m/z), 1169-1172 m/z (preferably about 1169.8 m/z), 1172-1175 m/z (preferably about 1173.7 m/z), 1184-1187 m/z (preferably about 1185.8 m/z), 1186-1189 m/z (preferably about 1187.8 m/z), 1198-1201 m/z (preferably about 1199.8 m/z), 1199-1202 m/z (preferably about 1200.8 m/z), 1200-1203 m/z (preferably about 1201.8 m/z), 1212-1215 m/z (preferably about 1213.8 m/z), 1214-1217 m/z (preferably about 1215.7 m/z), 1224-1227 m/z (preferably about 1225.7 m/z), 1226-1229 m/z (preferably about 1227.8 m/z), 1227-1230 m/z (preferably about 1228.8 m/z), 1228-1231 m/z (preferably about 1229.8 m/z), 1230-1233 m/z (preferably about 1231.7 m/z), 1240-1243 m/z (preferably about 1241.8 m/z), 1252-1255 m/z (preferably about 1253.8 m/z), 1254-1257 m/z (preferably about 1255.8 m/z), 1259-1262 m/z (preferably about 1260.8 m/z), 1268-1271 m/z (preferably about 1269.8 m/z), 1272-1275 m/z (preferably about 1273.8 m/z), 1282-1285 m/z (preferably about 1283.8 m/z), 1284-1287 m/z (preferably about 1285.8 m/z), 1286-1289 m/z (preferably about 1287.8 m/z), 1290-1293 m/z (preferably about 1291.8 m/z), 1296-1299 m/z (preferably about 1297.8 m/z), 1298-1301 m/z (preferably about 1299.8 m/z), 1300-1303 m/z (preferably about 1301.8 m/z), 1304-1307 m/z (preferably about 1305.8 m/z), 1310-1313 m/z (preferably about 1311.8 m/z), 1314-1317 m/z (preferably about 1315.8 m/z), 1316-1319 m/z (preferably about 1317.8 m/z), 1328-1331 m/z (preferably about 1329.8 m/z), 1330-1333 m/z (preferably about 1331.8 m/z), 1331-1334 m/z (preferably about 1332.8 m/z), 1332-1335 m/z (preferably about 1333.8 m/z), 1342-1345 m/z (preferably about 1343.8 m/z), 1344-1347 m/z (preferably about 1345.8 m/z), 1345-1348 m/z (preferably about 1346.8 m/z), 1356-1359 m/z (preferably about 1357.8 m/z), 1358-1361 m/z (preferably about 1359.8 m/z), 1360-1363 m/z (preferably about 1361.8 m/z), 1368-1371 m/z (preferably about 1369.8 m/z), 1370-1373 m/z (preferably about 1371.8 m/z), 1372-1375 m/z (preferably about 1373.8 m/z), 1374-1377 m/z (preferably about 1375.8 m/z), 1386-1389 m/z (preferably about 1387.8 m/z), 1388-1391 m/z (preferably about 1389.8 m/z), 1402-1405 m/z (preferably about 1403.8 m/z), 1414-1417 m/z (preferably about 1415.8 m/z), 1416-1419 m/z (preferably about 1417.8 m/z), 1428-1431 m/z (preferably about 1429.9 m/z), 1430-1433 m/z (preferably about 1431.9 m/z), 1519-1522 m/z (preferably about 1520.1 m/z), 1545-1548 m/z (preferably about 1546.1 m/z), 1547-1550 m/z (preferably about 1548.1 m/z), or a combination thereof.

In one embodiment, said seventh peak set comprises one or more (preferably two or more; more preferably three or more) further peak having a m/z of from 1266-1269 m/z (preferably about 1267.9 m/z), 1268-1271 m/z (preferably about 1269.9 m/z), 1310-1313 m/z (preferably about 1311.9 m/z), 1324-1327 m/z (preferably about 1325.9 m/z), 1338-1341 m/z (preferably about 1339.9 m/z), or a combination thereof.

In one embodiment, said ninth peak set comprises one or more (preferably two or more; more preferably three or more) further peak having a m/z of from 2115-2118 m/z (preferably about 2116.4 m/z), 2145-2148 m/z (preferably about 2146.4 m/z), 2157-2160 m/z (preferably about 2158.4 m/z), 2187-2190 m/z (preferably about 2188.4 m/z), 2188-2191 m/z (preferably about 2189.4 m/z), 2205-2208 m/z (preferably about 2206.4 m/z), 2219-2222 m/z (preferably about 2220.4 m/z), 2233-2236 m/z (preferably about 2234.4 m/z), 2245-2248 m/z (preferably about 2246.5 m/z), 2259-2262 m/z (preferably about 2260.5 m/z), 2277-2280 m/z (preferably about 2278.5 m/z), or a combination thereof.

In one embodiment, said tenth peak set comprises one or more (preferably two or more; more preferably three or more) further peak having a m/z of from 1848-1851 m/z (preferably about 1850 m/z), 2215-2218 m/z (preferably about 2216 m/z), 2231-2234 m/z (preferably about 2232 m/z), 2233-2236 m/z (preferably about 2234.1 m/z), 2235-2238 m/z (preferably about 2236.1 m/z), 2243-2246 m/z (preferably about 2244.1 m/z), 2244-2247 m/z (preferably about 2245.1 m/z), 2245-2248 m/z (preferably about 2246.1 m/z), 2247-2250 m/z (preferably about 2248.1 m/z), 2257-2260 m/z (preferably about 2258.1 m/z), 2260-2263 m/z (preferably about 2261.1 m/z), 2261-2264 m/z (preferably about 2261.1 m/z), 2262-2265 m/z (preferably about 2263.1 m/z), 2271-2274 m/z (preferably about 2272.1 m/z), 2285-2288 m/z (preferably about 2286.1 m/z), 2287-2290 m/z (preferably about 2288.1 m/z), 2289-2292 m/z (preferably about 2290.1 m/z), 2291-2294 m/z (preferably about 2292.1 m/z), 2389-2392 m/z (preferably about 2390.1 m/z), 2511-2514 m/z (preferably about 2512.1 m/z), 2549-2552 m/z (preferably about 2550.2 m/z), 2569-2572 m/z (preferably about 2570.2 m/z), or a combination thereof.

In one embodiment, said eleventh peak set comprises one or more (preferably two or more; more preferably three or more) further peak having a m/z of from 1311-1314 m/z (preferably about 1312.8 m/z), 1325-1328 m/z (preferably about 1326.8 m/z), 1369-1372 m/z (preferably about 1370.8 m/z), 1397-1400 m/z (preferably about 1398.8 m/z), or a combination thereof.

In one embodiment, said twelfth peak set comprises one or more (preferably two or more; more preferably three or more) further peak having a m/z of from 1228-1231 m/z (preferably about 1229.7 m/z), 1252-1255 m/z (preferably about 1253.7 m/z), 1254-1257 m/z (preferably about 1255.7 m/z), 1258-1261 m/z (preferably about 1259.7 m/z), 1268-1271 m/z (preferably about 1269.7 m/z), 1280-1283 m/z (preferably about 1281.7 m/z), 1282-1285 m/z (preferably about 1283.7 m/z), 1284-1287 m/z (preferably about 1285.7 m/z), 1286-1289 m/z (preferably about 1287.7 m/z), 1288-1291 m/z (preferably about 1289.7 m/z), 1294-1297 m/z (preferably about 1295.7 m/z), 1296-1299 m/z (preferably about 1297.7 m/z), 1308-1311 m/z (preferably about 1309.7 m/z), 1310-1313 m/z (preferably about 1311.7 m/z), 1314-1317 m/z (preferably about 1315.7 m/z), 1322-1325 m/z (preferably about 1323.7 m/z), 1324-1327 m/z (preferably about 1325.7 m/z), 1336-1339 m/z (preferably about 1337.7 m/z), or a combination thereof.

In one embodiment, said thirteenth peak set comprises one or more (preferably two or more; more preferably three or more) further peak having a m/z of from 1220-1223 m/z (preferably about 1221.7 m/z), 1303-1306 m/z (preferably about 1304.4 m/z), 1317-1320 m/z (preferably about 1318.4 m/z), 1345-1348 m/z (preferably about 1346.4 m/z), 1442-1445 m/z (preferably about 1444 m/z), 1456-1459 m/z (preferably about 1458 m/z), 1474-1477 m/z (preferably about 1476 m/z), 1485-1488 m/z (preferably about 1486 m/z), 1487-1490 m/z (preferably about 1488 m/z), 1695-1698 m/z (preferably about 1696.2 m/z), 1697-1700 m/z (preferably about 1698.2 m/z), 1723-1726 m/z (preferably about 1724.3 m/z), 1725-1728 m/z (preferably about 1726.3 m/z), 1739-1742 m/z (preferably about 1740.3 m/z), 2107-2110 m/z (preferably about 2108.3 m/z), 2132-2135 m/z (preferably about 2133.9 m/z), 2133-2136 m/z (preferably about 2134.9 m/z), 2147-2150 m/z (preferably about 2148.9 m/z), 2161-2164 m/z (preferably about 2162.9 m/z), 2175-2178 m/z (preferably about 2177 m/z), 2300-2303 m/z (preferably about 2301.3 m/z), 2316-2319 m/z (preferably about 2317.3 m/z), 2454-2457 m/z (preferably about 2455.5 m/z), 2496-2499 m/z (preferably about 2497.5 m/z), 2524-2527 m/z (preferably about 2525.6 m/z), 2586-2589 m/z (preferably about 2587.5 m/z), 2628-2631 m/z (preferably about 2629.6 m/z), 2656-2659 m/z (preferably about 2657.6 m/z), 2732-2735 m/z (preferably about 2733.6 m/z), 2736-2739 m/z (preferably about 2737.6 m/z), 2746-2749 m/z (preferably about 2747.6 m/z), 2774-2777 m/z (preferably about 2775.6 m/z), 2777-2780 m/z (preferably about 2778.6 m/z), 2786-2789 m/z (preferably about 2787.7 m/z), 2802-2805 m/z (preferably about 2803.7 m/z), 2804-2807 m/z (preferably about 2805.7 m/z), 2850-2853 m/z (preferably about 2851.7 m/z), 2892-2895 m/z (preferably about 2893.7 m/z), 2920-2923 m/z (preferably about 2921.8 m/z), or a combination thereof.

In one embodiment, said fourteenth peak set comprises one or more (preferably two or more; more preferably three or more) further peak having a m/z of from 1146-1149 m/z (preferably about 1147.9 m/z), 1160-1163 m/z (preferably about 1161.9 m/z), 1190-1193 m/z (preferably about 1191.9 m/z), 1196-1199 m/z (preferably about 1197.9 m/z), 1561-1564 m/z (preferably about 1562 m/z), 1881-1884 m/z (preferably about 1882.2 m/z), 1885-1888 m/z (preferably about 1886.2 m/z), 1897-1900 m/z (preferably about 1898.2 m/z), 1923-1926 m/z (preferably about 1924.2 m/z), 1925-1928 m/z (preferably about 1926.2 m/z), 1935-1938 m/z (preferably about 1936.2 m/z), 1937-1940 m/z (preferably about 1938.2 m/z), 1939-1942 m/z (preferably about 1940.2 m/z), 1951-1954 m/z (preferably about 1952.2 m/z), or a combination thereof.

In one embodiment, said fifteenth peak set comprises one or more (preferably two or more; more preferably three or more) further peak having a m/z of from 1184-1187 m/z (preferably about 1185.6 m/z), 1243-1246 m/z (preferably about 1244.6 m/z), or a combination thereof.

In one embodiment, said sixteenth peak set comprises one or more (preferably two or more; more preferably three or more) further peak having a m/z of from 1330-1333 m/z (preferably about 1331.9 m/z), 1344-1347 m/z (preferably about 1345.9 m/z), 1358-1361 m/z (preferably about 1360 m/z), 1372-1375 m/z (preferably about 1374 m/z), 1386-1389 m/z (preferably about 1387.9 m/z), 1388-1391 m/z (preferably about 1389.9 m/z), 1400-1403 m/z (preferably about 1401.9 m/z), 1402-1405 m/z (preferably about 1403.9 m/z), 1414-1417 m/z (preferably about 1415.9 m/z), or a combination thereof.

In one embodiment, said seventeenth peak set comprises one or more (preferably two or more; more preferably three or more) further peak having a m/z of from 1294-1297 m/z (preferably about 1295.9 m/z), 1296-1299 m/z (preferably about 1297.9 m/z), or a combination thereof.

In one embodiment, said eighteenth peak set comprises one or more (preferably two or more; more preferably three or more) further peak having a m/z of from 1723-1726 m/z (preferably about 1724.2 m/z), 1814-1817 m/z (preferably about 1815.8 m/z), or a combination thereof.

In one embodiment, said nineteenth peak set further comprises a peak having a m/z of from 1238-1241 m/z (preferably about 1239.9 m/z).

In one embodiment, said twentieth peak set comprises one or more (preferably two or more; more preferably three or more) further peak having a m/z of from 1039-1042 m/z (preferably about m/z), 1074-1077 m/z (preferably about m/z), 1124-1127 m/z (preferably about m/z), 1150-1153 m/z (preferably about m/z), 1184-1187 m/z (preferably about m/z), 1198-1201 m/z (preferably about m/z), 1212-1215 m/z (preferably about m/z), 1214-1217 m/z (preferably about m/z), 1220-1223 m/z (preferably about m/z), 1226-1229 m/z (preferably about m/z), 1228-1231 m/z (preferably about m/z), 1240-1243 m/z (preferably about m/z), 1242-1245 m/z (preferably about m/z), 1254-1257 m/z (preferably about m/z), 1256-1259 m/z (preferably about m/z), 1268-1271 m/z (preferably about m/z), 1270-1273 m/z (preferably about m/z), 1282-1285 m/z (preferably about m/z), 1284-1287 m/z (preferably about m/z), 1294-1297 m/z (preferably about m/z), 1296-1299 m/z (preferably about m/z), 1299-1302 m/z (preferably about m/z), 1310-1313 m/z (preferably about m/z), 1312-1315 m/z (preferably about m/z), 1313-1316 m/z (preferably about m/z), 1324-1327 m/z (preferably about m/z), 1330-1333 m/z (preferably about m/z), 1340-1343 m/z (preferably about m/z), 1354-1357 m/z (preferably about m/z), 1356-1359 m/z (preferably about m/z), 1357-1360 m/z (preferably about m/z), 1358-1361 m/z (preferably about m/z), 1368-1371 m/z (preferably about m/z), 1370-1373 m/z (preferably about m/z), 1372-1375 m/z (preferably about m/z), 1374-1377 m/z (preferably about m/z), 1382-1385 m/z (preferably about m/z), 1384-1387 m/z (preferably about m/z), 1386-1389 m/z (preferably about m/z), 1388-1391 m/z (preferably about m/z), 1398-1401 m/z (preferably about m/z), 1400-1403 m/z (preferably about m/z), 1417-1420 m/z (preferably about m/z), 1426-1429 m/z (preferably about m/z), 1429-1432 m/z (preferably about m/z), 1430-1433 m/z (preferably about m/z), 1440-1443 m/z (preferably about m/z), 1457-1460 m/z (preferably about m/z), 1459-1462 m/z (preferably about m/z), 1471-1474 m/z (preferably about m/z), 1473-1476 m/z (preferably about m/z), 1474-1477 m/z (preferably about m/z), 1487-1490 m/z (preferably about m/z), 1501-1504 m/z (preferably about m/z), 1529-1532 m/z (preferably about m/z), 1531-1534 m/z (preferably about m/z), 1541-1544 m/z (preferably about m/z), 1559-1562 m/z (preferably about m/z), 1571-1574 m/z (preferably about m/z), or a combination thereof.

In one embodiment, said twenty-first peak set comprises one or more (preferably two or more; more preferably three or more) further peak having a m/z of from 1042-1045 m/z (preferably about 1043.6 m/z), 1052-1055 m/z (preferably about 1053.5 m/z), 1124-1127 m/z (preferably about 1125 m/z), 1150-1153 m/z (preferably about 1151 m/z), 1204-1207 m/z (preferably about 1205.7 m/z), 1220-1223 m/z (preferably about 1221.7 m/z), 1244-1247 m/z (preferably about 1245.6 m/z), 1273-1276 m/z (preferably about 1274.3 m/z), 1287-1290 m/z (preferably about 1288.3 m/z), 1296-1299 m/z (preferably about 1297.9 m/z), 1390-1393 m/z (preferably about 1391.7 m/z), 1392-1395 m/z (preferably about 1393.7 m/z), 1427-1430 m/z (preferably about 1428 m/z), 1430-1433 m/z (preferably about 1431.9 m/z), 1442-1445 m/z (preferably about 1443.9 m/z), 1444-1447 m/z (preferably about 1446 m/z), 1458-1461 m/z (preferably about 1459.9 m/z), 1474-1477 m/z (preferably about 1475.9 m/z), 1475-1478 m/z (preferably about 1476.9 m/z), 1488-1491 m/z (preferably about 1489 m/z), 1534-1537 m/z (preferably about 1535.8 m/z), 1680-1683 m/z (preferably about 1681.9 m/z), 1697-1700 m/z (preferably about 1698.2 m/z), 1698-1701 m/z (preferably about 1699.2 m/z), 1707-1710 m/z (preferably about 1708.2 m/z), 1722-1725 m/z (preferably about 1723.2 m/z), 1723-1726 m/z (preferably about 1724.2 m/z), 1779-1782 m/z (preferably about 1780.2 m/z), 1819-1822 m/z (preferably about 1820.3 m/z), 1821-1824 m/z (preferably about 1822.3 m/z), 1838-1841 m/z (preferably about 1839.3 m/z), 2091-2094 m/z (preferably about 2092.2 m/z), 2103-2106 m/z (preferably about 2104.5 m/z), 2107-2110 m/z (preferably about 2108.3 m/z), 2117-2120 m/z (preferably about 2118.5 m/z), 2118-2121 m/z (preferably about 2119.5 m/z), 2119-2122 m/z (preferably about 2120.5 m/z), 2145-2148 m/z (preferably about 2146.5 m/z), 2159-2162 m/z (preferably about 2160.5 m/z), 2175-2178 m/z (preferably about 2176.5 m/z), 2356-2359 m/z (preferably about 2357.6 m/z), 2373-2376 m/z (preferably about 2374.6 m/z), 2397-2400 m/z (preferably about 2398.6 m/z), 2439-2442 m/z (preferably about 2440.7 m/z), 2455-2458 m/z (preferably about 2456.7 m/z), 2483-2486 m/z (preferably about 2484.7 m/z), 2495-2498 m/z (preferably about 2496.7 m/z), 2512-2515 m/z (preferably about 2513.7 m/z), 2513-2516 m/z (preferably about 2514.7 m/z), 2777-2780 m/z (preferably about 2778.9 m/z), 2780-2783 m/z (preferably about 2781.9 m/z), 2793-2796 m/z (preferably about 2794.9 m/z), 2807-2810 m/z (preferably about 2808.9 m/z), 2809-2812 m/z (preferably about 2810.9 m/z), 2821-2824 m/z (preferably about 2822.9 m/z), 2822-2825 m/z (preferably about 2823.9 m/z), 2834-2837 m/z (preferably about 2835.9 m/z), 2849-2852 m/z (preferably about 2850.9 m/z), 2851-2854 m/z (preferably about 2852.9 m/z), or a combination thereof.

In one embodiment, said twenty-second peak set comprises one or more (preferably two or more; more preferably three or more) further peak having a m/z of from 1043-1046 m/z (preferably about 1044.6 m/z), 1071-1074 m/z (preferably about 1072.6 m/z), 1073-1076 m/z (preferably about 1074.6 m/z), 1079-1082 m/z (preferably about 1080.6 m/z), 1468-1471 m/z (preferably about 1469.7 m/z), 1474-1477 m/z (preferably about 1475.8 m/z), 1476-1479 m/z (preferably about 1477.8 m/z), 1482-1485 m/z (preferably about 1483.7 m/z), 1484-1487 m/z (preferably about 1485.7 m/z), 1490-1493 m/z (preferably about 1491.8 m/z), 1496-1499 m/z (preferably about 1497.8 m/z), 1504-1507 m/z (preferably about 1505.8 m/z), 1510-1513 m/z (preferably about 1511.8 m/z), or a combination thereof.

In one embodiment, said twenty-third peak set comprises one or more (preferably two or more; more preferably three or more) further peak having a m/z of from 1306-1309 m/z (preferably about 1307.6 m/z), 1404-1407 m/z (preferably about 1405.7 m/z), 1418-1421 m/z (preferably about 1419.7 m/z), 1420-1423 m/z (preferably about 1421.7 m/z), 1430-1433 m/z (preferably about 1431.7 m/z), 1444-1447 m/z (preferably about 1445.7 m/z), 1448-1451 m/z (preferably about 1449.7 m/z), 1458-1461 m/z (preferably about 1459.7 m/z), 1462-1465 m/z (preferably about 1463.7 m/z), 1472-1475 m/z (preferably about 1473.7 m/z), 1488-1491 m/z (preferably about 1489.7 m/z), 1490-1493 m/z (preferably about 1491.7 m/z), 1502-1505 m/z (preferably about 1503.7 m/z), 1511-1514 m/z (preferably about 1512.8 m/z), or a combination thereof.

In one embodiment, said twenty-fourth peak set comprises one or more (preferably two or more; more preferably three or more) further peak having a m/z of from 1198-1201 m/z (preferably about 1199.7 m/z), 1200-1203 m/z (preferably about 1201.8), 1212-1215 m/z (preferably about 1213.8 m/z), 1214-1217 m/z (1215.8 m/z), 1224-1227 m/z (preferably about 1225.8 m/z), 1226-1229 m/z (preferably about 1227.8 m/z), 1228-1231 m/z (preferably about 1229.8 m/z), 1238-1241 m/z (preferably about 1239.8 m/z), 1240-1243 m/z (preferably about 1241.8 m/z), 1252-1255 m/z (preferably about 1253.9 m/z), 1254-1257 m/z (preferably about 1255.9 m/z), 1266-1269 m/z (preferably about 1267.9 m/z), 1268-1271 m/z (preferably about 1269.9 m/z), 1280-1283 m/z (preferably about 1281.9 m/z), 1282-1285 m/z (preferably about 1283.9 m/z), 1298-1301 m/z (preferably about 1299.9 m/z), 1300-1303 m/z (preferably about 1301.9 m/z), 1342-1345 m/z (preferably about 1343.9 m/z), 1312-1315 m/z (preferably about 1313.7 m/z), 1388-1391 m/z (preferably about 1389.7 m/z), 1402-1405 m/z (preferably about 1403.8 m/z), 1430-1433 m/z (preferably about 1431.8 m/z), 1458-1461 m/z (preferably about 1459.8 m/z), or a combination thereof.

In one embodiment, said twenty-fourth peak set comprises one or more (preferably two or more; more preferably three or more) further peak having a m/z of from 1198-1201 m/z (preferably about 1199.7 m/z), 1312-1315 m/z (preferably about 1313.7 m/z), 1388-1391 m/z (preferably about 1389.7 m/z), 1402-1405 m/z (preferably about 1403.8 m/z), 1430-1433 m/z (preferably about 1431.8 m/z), 1458-1461 m/z (preferably about 1459.8 m/z), or a combination thereof.

In one embodiment, said twenty-fifth peak set comprises one or more (preferably two or more; more preferably three or more) further peak having an m/z of from 1072-1075 m/z (preferably about 1073.6 m/z), 1198-1201 m/z (preferably about 1199.7 m/z), 1224-1227 m/z (preferably about 1225.6 m/z), 1228-1231 m/z (preferably about 1229.6 m/z), 1248-1251 m/z (preferably about 1249.9 m/z), 1252-1255 m/z (preferably about 1253.7 m/z), 1254-1257 m/z (preferably about 1255.8 m/z), 1260-1263 m/z (preferably about 1261.9 m/z), 1262-1265 m/z (preferably about 1263.9 m/z), 1266-1269 m/z (preferably about 1267.8 m/z), 1268-1271 m/z (preferably about 1269.7 m/z), 1274-1277 m/z (preferably about 1275.9 m/z), 1276-1279 m/z (preferably about 1277.9 m/z), 1280-1283 m/z (preferably about 1281.8 m/z), 1282-1285 m/z (preferably about 1283.9 m/z), 1288-1291 m/z (preferably about 1289.9 m/z), 1290-1293 m/z (preferably about 1291.9 m/z), 1294-1297 m/z (preferably about 1295.9 m/z), 1296-1299 m/z (preferably about 1297.9 m/z), 1298-1301 m/z (preferably about 1299.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), 1338-1341 m/z (preferably about 1339.9 m/z), 1346-1349 m/z (preferably about 1347.9 m/z), 1360-1363 m/z (preferably about 1361.9 m/z), 1374-1377-m/z (preferably about 1375.7 m/z), 1388-1391 m/z (preferably about 1389.7 m/z), 1402-1405 m/z (preferably about 1403.7 m/z), 1416-1419 m/z (preferably about 1417.7 m/z), 1430-1433 m/z (preferably about 1431.7 m/z), 1719-1722 m/z (preferably about 1720 m/z), 1735-1738 m/z (preferably about 1736 m/z), 1747-1750 m/z (preferably about 1748.1 m/z), 1761-1764 m/z (preferably about 1762.1 m/z), 1764-1767 m/z (preferably about 1765.1 m/z), 1789-1792 m/z (preferably about 1790.1 m/z) or a combination thereof.

In one embodiment, said twenty-fifth peak set comprises one or more (preferably two or more; more preferably three or more) further peak having an m/z of from 1072-1075 m/z (preferably about 1073.6 m/z), 1248-1251 m/z (preferably about 1249.9 m/z), 1252-1255 m/z (preferably about 1253.7 m/z), 1254-1257 m/z (preferably about 1255.8 m/z), 1260-1263 m/z (preferably about 1261.9 m/z), 1262-1265 m/z (preferably about 1263.9 m/z), 1266-1269 m/z (preferably about 1267.8 m/z), 1268-1271 m/z (preferably about 1269.7 m/z), 1274-1277 m/z (preferably about 1275.9 m/z), 1276-1279 m/z (preferably about 1277.9 m/z), 1280-1283 m/z (preferably about 1281.8 m/z), 1282-1285 m/z (preferably about 1283.9 m/z), 1288-1291 m/z (preferably about 1289.9 m/z), 1290-1293 m/z (preferably about 1291.9 m/z), 1294-1297 m/z (preferably about 1295.9 m/z), 1296-1299 m/z (preferably about 1297.9 m/z), 1298-1301 m/z (preferably about 1299.9 m/z), 1304-1307 m/z (preferably about 1305.9 m/z), 1308-1311 m/z (preferably about 1309.9 m/z), 1310-1313 m/z (preferably about 1311.9 m/z), 1314-1317 m/z (preferably about 1315.9 m/z), 1318-1321 m/z (preferably about 1319.9 m/z), 1320-1323 m/z (preferably about 1321.9 m/z), 1322-1325 m/z (preferably about 1323.9 m/z), 1324-1327 m/z (preferably about 1325.9 m/z), 1332-1335 m/z (preferably about 1333.9 m/z), 1336-1339 m/z (preferably about 1337.9 m/z), 1338-1341 m/z (preferably about 1339.9 m/z), 1346-1349 m/z (preferably about 1347.9 m/z), 1360-1363 m/z (preferably about 1361.9 m/z), 1430-1433 m/z (preferably about 1431.7 m/z), 1719-1722 m/z (preferably about 1720 m/z), 1735-1738 m/z (preferably about 1736 m/z), 1747-1750 m/z (preferably about 1748.1 m/z), 1761-1764 m/z (preferably about 1762.1 m/z), 1764-1767 m/z (preferably about 1765.1 m/z), 1789-1792 m/z (preferably about 1790.1 m/z) or a combination thereof.

In one embodiment, said twenty-fifth peak set comprises one or more (preferably two or more; more preferably three or more) further peak having an m/z of from 1198-1201 m/z (preferably about 1199.7 m/z), 1224-1227 m/z (preferably about 1225.6 m/z), 1228-1231 m/z (preferably about 1229.6 m/z), 1252-1255 m/z (preferably about 1253.7 m/z), 1268-1271 m/z (preferably about 1269.7 m/z), 1374-1377-m/z (preferably about 1375.7 m/z), 1388-1391 m/z (preferably about 1389.7 m/z), 1402-1405 m/z (preferably about 1403.7 m/z), 1416-1419 m/z (preferably about 1417.7 m/z), 1430-1433 m/z (preferably about 1431.7 m/z), or a combination thereof.

In one embodiment, said twenty-fifth peak set comprises one or more (preferably two or more; more preferably three or more) further peak having an m/z of from 1252-1255 m/z (preferably about 1253.7 m/z), 1268-1271 m/z (preferably about 1269.7 m/z), 1430-1433 m/z (preferably about 1431.7 m/z), or a combination thereof.

Said thirty-eight peak set may comprise one or more (preferably two or more; more preferably three or more) further defined peak selected from: a peak having a m/z of from 604-607 m/z (preferably about 606 m/z), a peak having a m/z of from 673-676 m/z (preferably about 675 m/z), a peak having a m/z of from 689-692 m/z (preferably about 691 m/z), a peak having a m/z of from 711-714 m/z (preferably about 713 m/z), a peak having a m/z of from 726-729 m/z (preferably about 728 m/z), a peak having a m/z of from 727-730 m/z (preferably about 729 m/z), a peak having a m/z of from 773-776 m/z (preferably about 775 m/z), a peak having a m/z of from 796-799 m/z (preferably about 798 m/z), a peak having a m/z of from 797-800 m/z (preferably about 799 m/z), a peak having a m/z of from 1174-1177 m/z (preferably about 1175 m/z), a peak having a m/z of from 1248-1251 m/z (preferably about 1249 m/z), a peak having a m/z of from 1249-1252 m/z (preferably about 1250 m/z), a peak having a m/z of from 1276-1279 m/z (preferably about 1277 m/z), a peak having a m/z of from 1278-1281 m/z (preferably about 1279 m/z), a peak having a m/z of from 1290-1293 m/z (preferably about 1291 m/z), a peak having a m/z of from 1304-1307 m/z (preferably about 1305 m/z), a peak having a m/z of from 1305-1308 m/z (preferably about 1306 m/z), a peak having a m/z of from 1318-1321 m/z (preferably about 1319 m/z), a peak having a m/z of from 1332-1335 m/z (preferably about 1333 m/z), a peak having a m/z of from 1333-1336 m/z (preferably about 1335 m/z), a peak having a m/z of from 1334-1337 m/z (preferably about 1336 m/z), a peak having a m/z of from 1346-1349 m/z (preferably about 1348 m/z), a peak having a m/z of from 1360-1363 m/z (preferably about 1362 m/z), a peak having a m/z of from 1361-1364 m/z (preferably about 1363 m/z), a peak having a m/z of from 1374-1377 m/z (preferably about 1376 m/z), a peak having a m/z of from 1384-1387 m/z (preferably about 1385 m/z), a peak having a m/z of from 1385-1388 m/z (preferably about 1386 m/z), a peak having a m/z of from 1388-1391 m/z (preferably about 1390 m/z), a peak having a m/z of from 1396-1399 m/z (preferably about 1397 m/z), a peak having a m/z of from 1398-1401 m/z (preferably about 1399 m/z), a peak having a m/z of from 1440-1443 m/z (preferably about 1441 m/z), a peak having a m/z of from 1442-1445 m/z (preferably about 1443 m/z), a peak having a m/z of from 1456-1459 m/z (preferably about 1457 m/z), a peak having a m/z of from 1650-1653 m/z (preferably about 1652 m/z), a peak having a m/z of from 1651-1654 m/z (preferably about 1653 m/z), a peak having a m/z of from 1676-1679 m/z (preferably about 1678 m/z), a peak having a m/z of from 1677-1680 m/z (preferably about 1679 m/z), a peak having a m/z of from 1678-1681 m/z (preferably about 1680 m/z), a peak having a m/z of from 1692-1695 m/z (preferably about 1694 m/z), a peak having a m/z of from 1693-1696 m/z (preferably about 1695 m/z), a peak having a m/z of from 2060-2063 m/z (preferably about 2061 m/z), a peak having a m/z of from 2341-2344 m/z (preferably about 2342 m/z), a peak having a m/z of from 2458-2461 m/z (preferably about 2459 m/z), a peak having a m/z of from 2500-2503 m/z (preferably about 2501 m/z), a peak having a m/z of from 2514-2517 m/z (preferably about 2515 m/z), and a peak having a m/z of from 2542-2545 m/z (preferably about 2543 m/z).

For example, said one or more further defined peak may be selected from: a peak having a m/z of from 1248-1251 m/z (preferably about 1249 m/z), a peak having a m/z of from 1249-1252 m/z (preferably about 1250 m/z), a peak having a m/z of from 1276-1279 m/z (preferably about 1277 m/z), a peak having a m/z of from 1278-1281 m/z (preferably about 1279 m/z), a peak having a m/z of from 1290-1293 m/z (preferably about 1291 m/z), a peak having a m/z of from 1304-1307 m/z (preferably about 1305 m/z), a peak having a m/z of from 1305-1308 m/z (preferably about 1306 m/z), a peak having a m/z of from 1318-1321 m/z (preferably about 1319 m/z), a peak having a m/z of from 1332-1335 m/z (preferably about 1333 m/z), a peak having a m/z of from 1333-1336 m/z (preferably about 1335 m/z), a peak having a m/z of from 1334-1337 m/z (preferably about 1336 m/z), a peak having a m/z of from 1346-1349 m/z (preferably about 1348 m/z), a peak having a m/z of from 1360-1363 m/z (preferably about 1362 m/z), a peak having a m/z of from 1361-1364 m/z (preferably about 1363 m/z), a peak having a m/z of from 1374-1377 m/z (preferably about 1376 m/z), a peak having a m/z of from 1384-1387 m/z (preferably about 1385 m/z), a peak having a m/z of from 1385-1388 m/z (preferably about 1386 m/z), a peak having a m/z of from 1388-1391 m/z (preferably about 1390 m/z), a peak having a m/z of from 1396-1399 m/z (preferably about 1397 m/z), and a peak having a m/z of from 1398-1401 m/z (preferably about 1399 m/z). Advantageously, said defined peaks may be indicative of the presence of a sulfoglycolipid (which, amongst Mycobacteria, are type-specific for *M. tuberculosis*).

Said thirty-ninth peak set may comprise one or more (preferably two or more; more preferably three or more) further defined peak selected from: a peak having a m/z of from 1004-1007 m/z (preferably about 1005 m/z), a peak having a m/z of from 1005-1008 m/z (preferably about 1006 m/z), a peak having a m/z of from 1019-1022 m/z (preferably about 1021 m/z), a peak having a m/z of from 1026-1029 m/z (preferably about 1027 m/z), a peak having a m/z of from 1027-1030 m/z (preferably about 1028 m/z), a peak having a m/z of from 1033-1036 m/z (preferably about 1034 m/z), a peak having a m/z of from 1047-1050 m/z (preferably about 1048 m/z), a peak having a m/z of from 1049-1052 m/z (preferably about 1050 m/z), a peak having a m/z of from 1057-1060 m/z (preferably about 1059 m/z), a peak having a m/z of from 1069-1072 m/z (preferably about 1070 m/z), a peak having a m/z of from 1085-1088 m/z (preferably about 1087 m/z), a peak having a m/z of from 1134-1137 m/z (preferably about 1135 m/z), a peak having a m/z of from 1157-1160 m/z (preferably about 1158 m/z), a peak having a m/z of from 1174-1177 m/z (preferably about 1175 m/z), a peak having a m/z of from 1176-1179 m/z (preferably about 1177 m/z), a peak having a m/z of from 1177-1180 m/z (preferably about 1178 m/z), a peak having a m/z of from 1180-1183 m/z (preferably about 1181 m/z), a peak having a m/z of from 1190-1193 m/z (preferably about 1191 m/z), a peak having a m/z of from 1192-1195 m/z (preferably about 1193 m/z), a peak having a m/z of from 1204-1207 m/z (preferably about 1205 m/z), a peak having a m/z of from 1205-1208 m/z (preferably about 1206 m/z), a peak having a m/z of from 1218-1221 m/z (preferably about 1219 m/z), a peak having a m/z of from 1246-1249 m/z (preferably about 1247 m/z), a peak having a m/z of from 1248-1251 m/z (preferably about 1249 m/z), a peak having a m/z of from 1260-1263 m/z (preferably about 1261 m/z), a peak having a m/z of from 1262-1265 m/z (preferably about 1263 m/z), a peak having a m/z of from 1266-1269 m/z (preferably about 1267 m/z), a peak having a m/z of from 1268-1271 m/z (preferably about 1269 m/z), a peak having a m/z of from 1270-1273 m/z (preferably about 1271 m/z), a peak having a m/z of from 1274-1277 m/z (preferably about 1275 m/z), a peak having a m/z of from 1276-1279 m/z (preferably about 1277 m/z), a peak having a m/z of from 1277-1280 m/z (preferably about 1278 m/z), a peak having a m/z of from 1280-1283 m/z (preferably about 1281 m/z), a peak having a m/z of from 1282-1285 m/z (preferably about 1283 m/z), a peak having a m/z of from 1283-1286 m/z (preferably about 1284 m/z), a peak having a m/z of from 1288-1291 m/z (preferably about 1289 m/z), a peak having a m/z of from 1294-1297 m/z (preferably about 1295 m/z), a peak having a m/z of from 1296-1299 m/z (preferably about 1297 m/z), a peak having a m/z of from 1302-1305 m/z (preferably about 1303 m/z), a peak having a m/z of from 1304-1307 m/z (preferably about 1305 m/z), a peak having a m/z of from 1308-1311 m/z (preferably about 1309 m/z), a peak having a m/z of from 1310-1313 m/z (preferably about 1311 m/z), a peak having a m/z of from 1311-1314 m/z (preferably about 1312 m/z), a peak having a m/z of from 1316-1319 m/z (preferably about 1317 m/z), a peak having a m/z of from 1318-1321 m/z (preferably about 1319 m/z), a peak having a m/z of from 1325-1328 m/z (preferably about 1326 m/z), a peak having a m/z of from 1327-1330 m/z (preferably about 1328 m/z), a peak having a m/z of from 1330-1333 m/z (preferably about 1331 m/z), a peak having a m/z of from 1336-1339 m/z (preferably about 1337 m/z), a peak having a m/z of from 1338-1341 m/z (preferably about 1339 m/z), a peak having a m/z of from 1340-1343 m/z (preferably about 1341 m/z), a peak having a m/z of from 1344-1347 m/z (preferably about 1345 m/z), a peak having a m/z of from 1346-1349 m/z (preferably about 1347 m/z), a peak having a m/z of from 1352-1355 m/z (preferably about 1353 m/z), a peak having a m/z of from 1353-1356 m/z (preferably about 1354 m/z), a peak having a m/z of from 1355-1358 m/z (preferably about 1353 m/z), a peak having a m/z of from 1358-1361 m/z (preferably about 1359 m/z), a peak having a m/z of from 1366-1369 m/z (preferably about 1367 m/z), a peak having a m/z of from 1368-1371 m/z (preferably about 1369 m/z), a peak having a m/z of from 1378-1381 m/z (preferably about 1379 m/z), a peak having a m/z of from 1380-1383 m/z (preferably about 1381 m/z), a peak having a m/z of from 1384-1387 m/z (preferably about 1385 m/z), a peak having a m/z of from 1392-1395 m/z (preferably about 1393 m/z), a peak having a m/z of from 1394-1397 m/z (preferably about 1395 m/z), a peak having a m/z of from 1396-1399 m/z (preferably about 1397 m/z), a peak having a m/z of from 1406-1409 m/z (preferably about 1407 m/z), a peak having a m/z of from 1408-1411 m/z (preferably about 1409 m/z), a peak having a m/z of from 1412-1415 m/z (preferably about 1413 m/z), a peak having a m/z of from 1692-1695 m/z (preferably about 1693 m/z), and a peak having a m/z of from 1693-1696 m/z (preferably about 1694 m/z).

Said fortieth peak set may comprise one or more (preferably two or more; more preferably three or more) further defined peak selected from: a peak having a m/z of from 1240-1243 m/z (preferably about 1241 m/z), a peak having a m/z of from 1242-1245 m/z (preferably about 1243 m/z), and a peak having a m/z of from 1384-1387 m/z (preferably about 1385 m/z).

In one embodiment, methods of the invention may comprise measuring the concentration of a bacterial membrane lipid in a sample. For example, the concentration of a bacterial membrane lipid may be measured by measuring the intensity (e.g. largest y-axis value) of a peak in a mass spectrum output.

In one embodiment, when the presence of one or more of said peaks set(s) is detected, the subject may be administered a medicament to treat a Mycobacterial infection, preferably an antibiotic. Suitable antibiotics include clarithromycin, amikacin, and cefoxitin. Clarithromycin may be a preferred antibiotic.

In one embodiment, the sample (obtained from a subject) comprises less than about $10^{10}$ bacterial cells. Suitably, a sample may comprise less than about $10^9$, $10^8$, $10^7$, $10^6$, $10^5$, $10^4$, $10^3$, $10^2$ or $10^1$ bacterial cells.

In one embodiment the sample (obtained from a subject) comprises between about $10^1$ to about $10^{10}$ bacterial cells. Suitably, a test sample comprises between about $10^2$ to about $10^8$, about $10^3$ to about $10^6$, or about $10^4$ to about $10^5$ bacterial cells.

In one embodiment, the method further comprises the step of recording on a suitable data carrier the data obtained in a step of subjecting the sample to mass spectrometry analysis to provide a mass spectrum output. In one aspect there is provided a data carrier comprising the data obtained in a step of subjecting the sample to mass spectrometry analysis to provide a mass spectrum output.

This matrix solution described herein may be provided as a kit, as the component parts synergise with one another to provide a matrix solution uniquely capable of allowing mass spectrometry analysis of lipids (particularly lipids present as an integral component of intact bacterium).

Thus, in one aspect there is provided a kit comprising:

a. 2,5-dihydroxybenzoic acid and/or super 2,5-dihydroxybenzoic acid (e.g. at any concentration described above);

b. an organic solvent (e.g. at any concentration described above), preferably ethanol;

c. preferably instructions to perform a method described herein.

The kit may be for use in a method for identifying a subject suitable for receiving a lung transplant; and/or for use in a method for screening operating theatre equipment for use in cardiothoracic surgery of a subject; and/or for use in method for identifying the presence or absence of a bacterial infection in a subject subsequent to receiving open heart surgery and/or a heart transplant; and/or for use in a method for detecting the presence or absence of a *Mycobacterium*. The invention further embraces corresponding use of said kit in a method described herein.

In one embodiment, the kit comprises instructions to use said kit for subjecting a sample described herein (such as a sample isolated from a subject described herein) to mass spectrometry analysis to provide a mass spectrum output.

In one embodiment, the kit comprises instructions to use said kit in a method described herein.

The invention embraces use of a kit described herein for detecting a bacterial membrane lipid in a sample by mass spectrometry.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a spectrum" includes a plurality of such spectra and reference to "the lipid" includes reference to one or more lipids and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples

FIGURES

Embodiments of the invention will now be described, by way of example only, with reference to the following Figures. FIGS. 1-31 show positive ion MALDI-ToF MS spectra (typically across the spectrum of m/z 1000-2600) displaying a peak set (e.g. lipid fingerprint) identifiable in a sample of a subject which is not suitable for receiving a lung transplant and/or open heart surgery. The matrix solution used was DHB (10 mg) suspended in 25% EtOH. FIGS. 32-34 show negative ion MALDI-ToF MS spectra (same matrix solution, DHB in EtOH).

Figure 35:
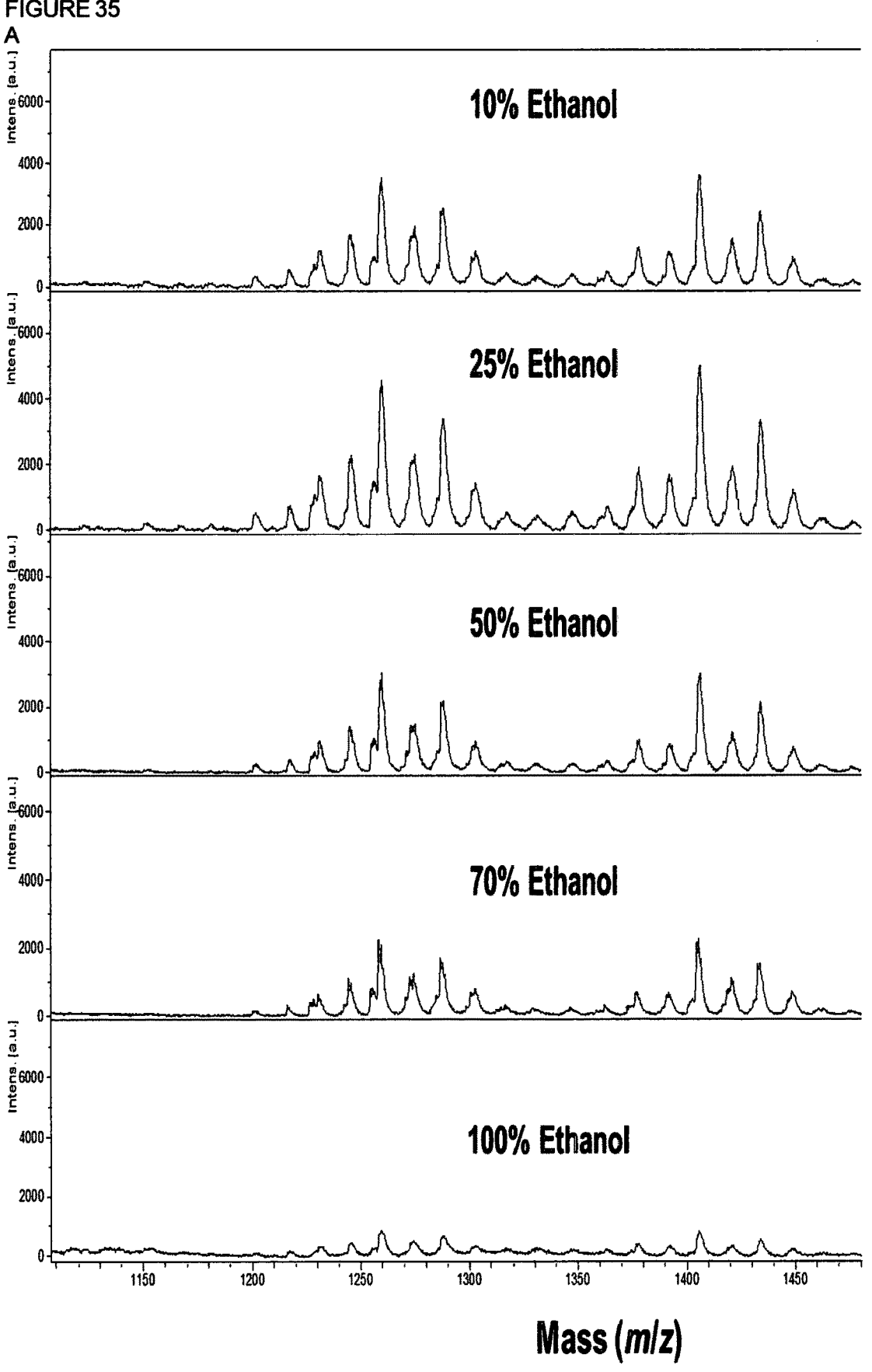
Figure 35:
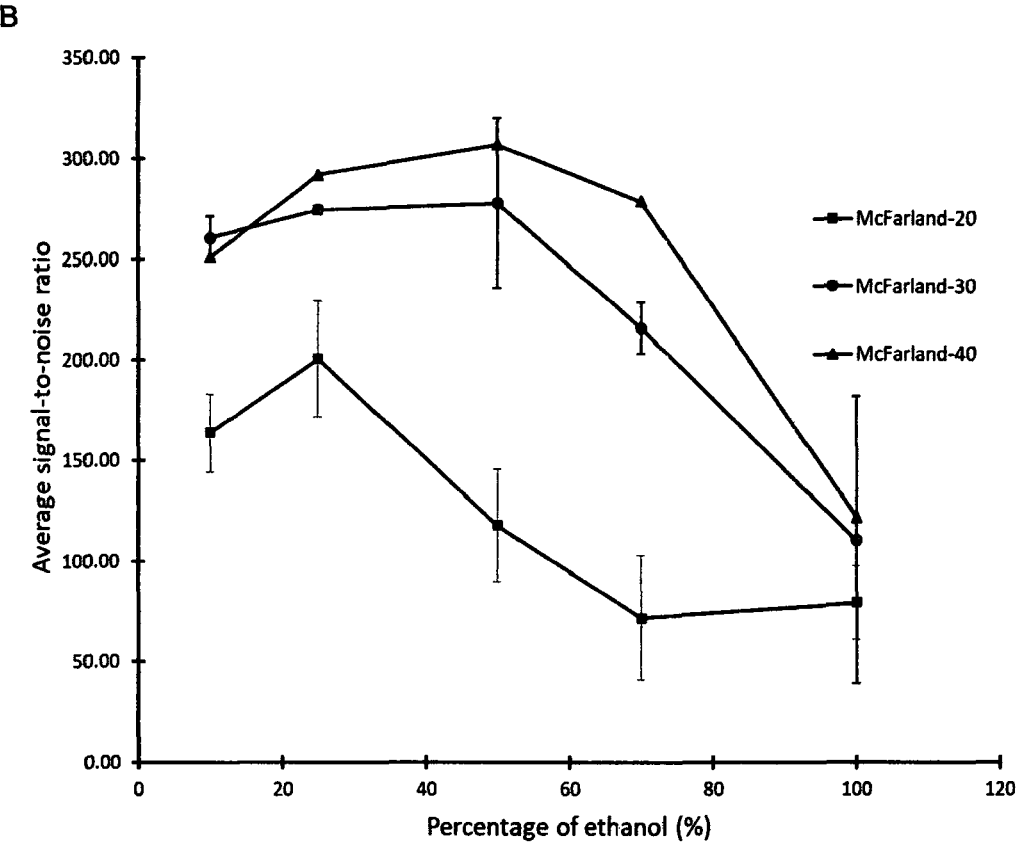
Figure 35:
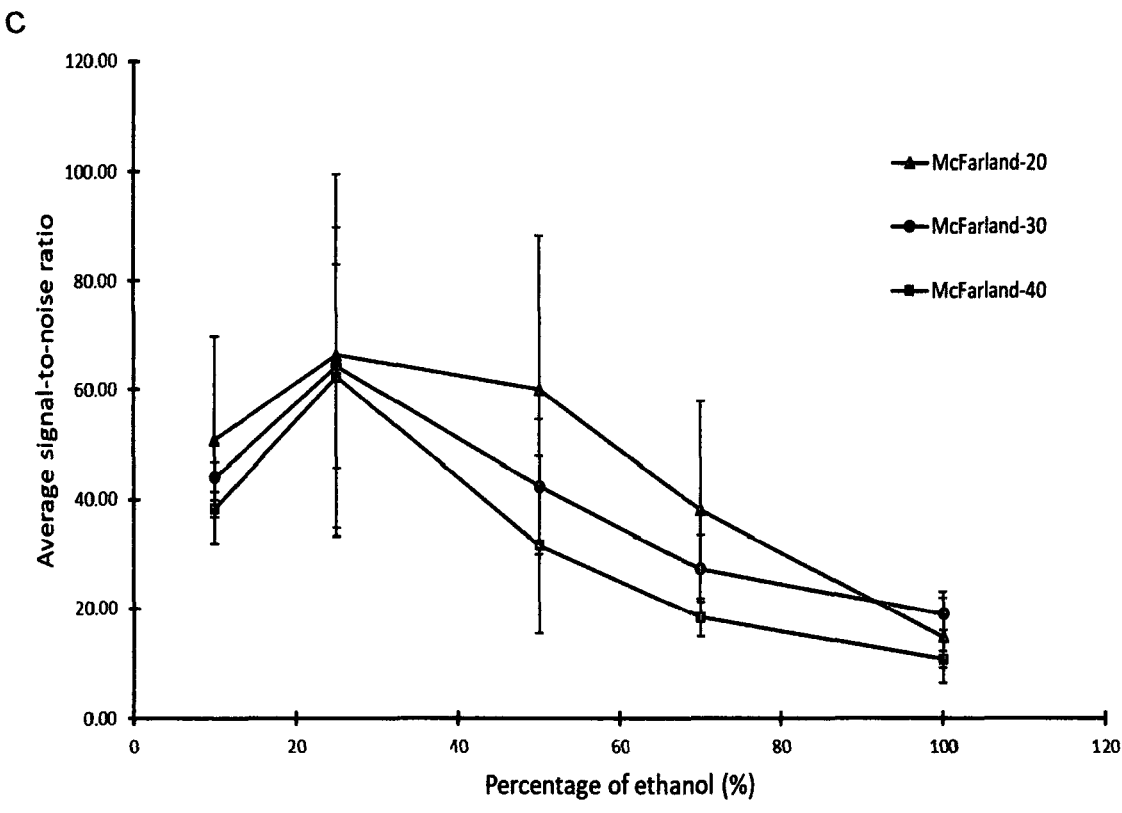

FIG. 35 (A) shows a mass spectrum output for *M. abscessus* when using a matrix solution with different concentrations of organic solvent. (B) Graph showing average signal-to-noise ratio with reference to the percentage of organic solvent (EtOH) for *M. abscessus* cultured on agar (solid medium). (C) Graph showing average signal-to-noise ratio with reference to the percentage of organic solvent (EtOH) *M. abscessus* cultured in liquid medium.

EXAMPLES

Materials and Methods

Bacterial Strains

Reference bacterial strains were obtained from the Belgian Co-ordinated Collections of Microorganisms (BOOM, Antwerp, Belgium) and from the European Centres for Disease Control (ECDC) (Table 1).

TABLE 1

| Mycobacterium reference strains | | | | |
|---|---|---|---|---|
| Strains (n = 29) | Complex | | Source | RGM/SGM |
| *M. abscessus* | *M. abscessus* complex | BCCM | C04975 | RGM |
| *M. avium* | *M. avium* complex | BCCM | C01788 | RGM |
| *M. bohemicum* | | ECDC | | SGM |
| *M. celatum* | | ECDC | | SGM |
| *M. chelonae* | | Unknown | 17T9705 | RGM |
| *M. chimaera* | *M. avium* complex | BCCM | 130444 | RGM |
| *M. chimaera* | *M. avium* complex | BCCM | 2015-01546 | RGM |
| *M. fortuitum* | *M. fortuitum* complex | BCCM | 52847 | RGM |
| *M. fortuitum* | *M. fortuitum* complex | ECDC | | RGM |
| *M. gordonae* | | BCCM | C02565 | SGM |
| *M. interjectum* | | ECDC | | SGM |
| *M. intermedium* | | ECDC | | RGM |
| *M. intracellulare* | *M. avium* complex | ECDC | | SGM |
| *M. intracellulare* | *M. avium* complex | BCCM | 120584 | SGM |
| *M. kansasii* | | BCCM | 960032 | SGM |
| *M. marinum* | | ECDC | | SGM |
| *M. nonchromogenicum* | | ECDC | | SGM |
| *M. peregrinum* | *M. fortuitum* complex | BCCM | 970462 | RGM |
| *M. peregrinum* | *M. fortuitum* complex | ECDC | | RGM |
| *M. scrofulaceum* | | BCCM | C01934 | SGM |
| *M. scrofulaceum* | | ECDC | | SGM |
| *M. shimoidei* | | ECDC | | SGM |
| *M. simiae* | | BCCM | C02428 | SGM |
| *M. simiae* | | ECDC | | SGM |
| *M. smegmatis* | | BCCM | M010336 | SGM |
| *M. szulgai* | | BCCM | M003303 | SGM |
| *M. ulcerans* | | BCCM | C05150 | SGM |
| *M. xenopi* | | ECDC | | SGM |
| *M. xenopi* | | BCCM | C05984 | SGM |

RGM = rapidly growing mycobacteria; SGM = slowly growing mycobacteria.

Figure 1:
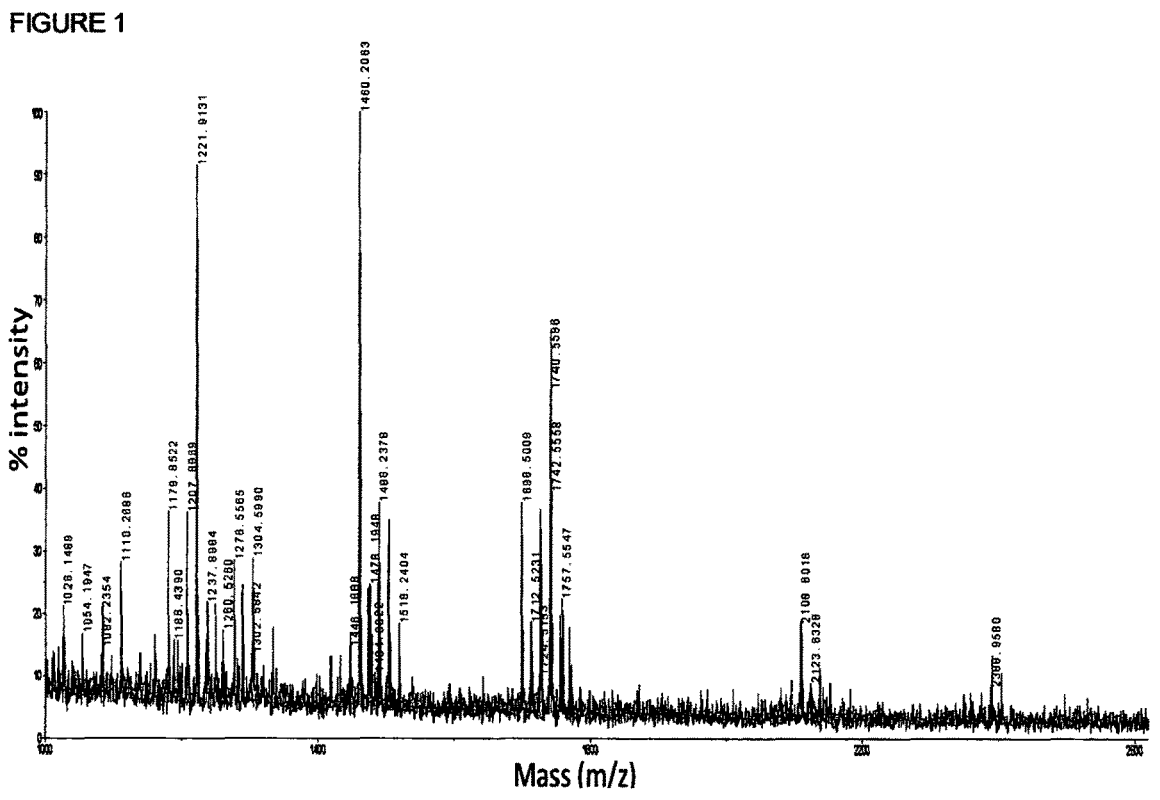
FIG. 1 shows a mass spectrum output having peaks of a second peak set (e.g. indicative for *M. tuberculosis* (ATCC, H37Rv))
Figure 2:
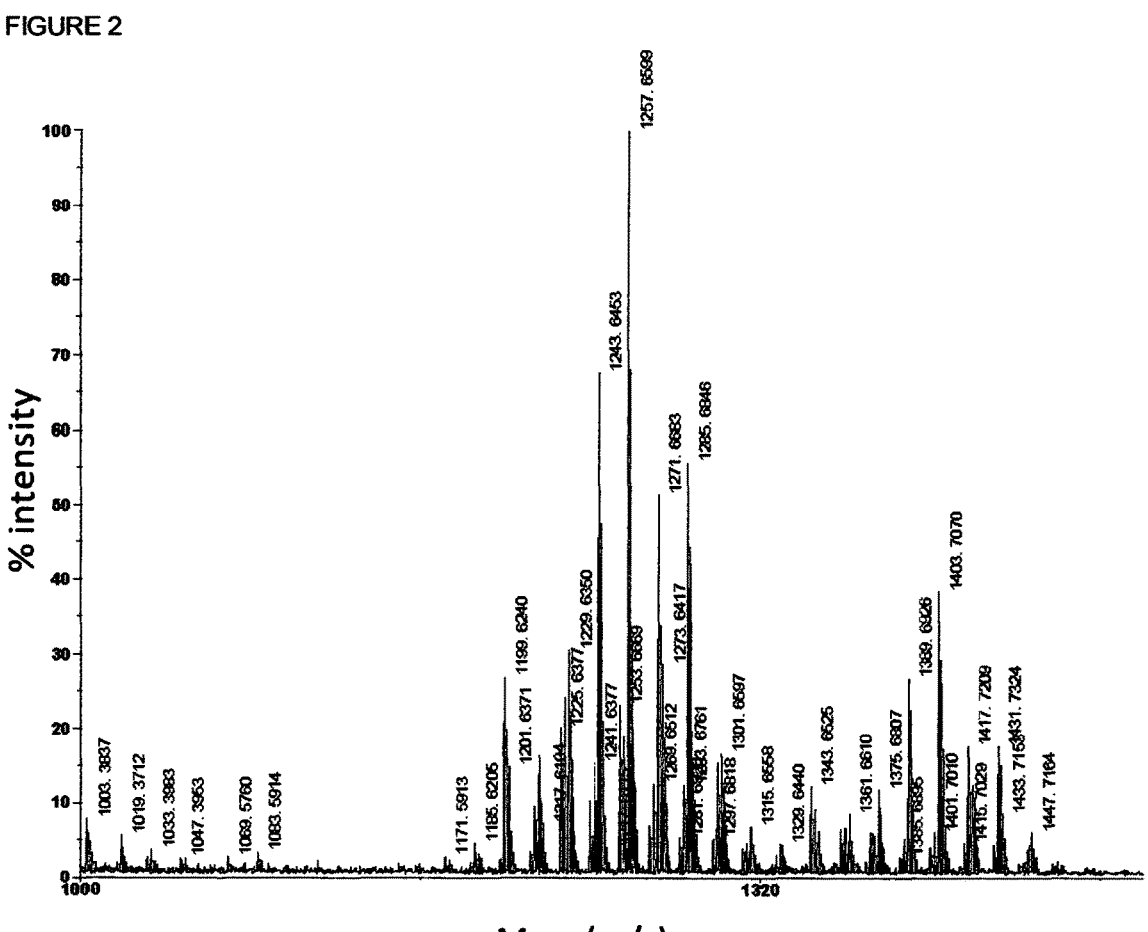
FIG. 2 shows a mass spectrum output having peaks of a twenty-fifth peak set (e.g. indicative for *M. massiliense*)
Figure 3:
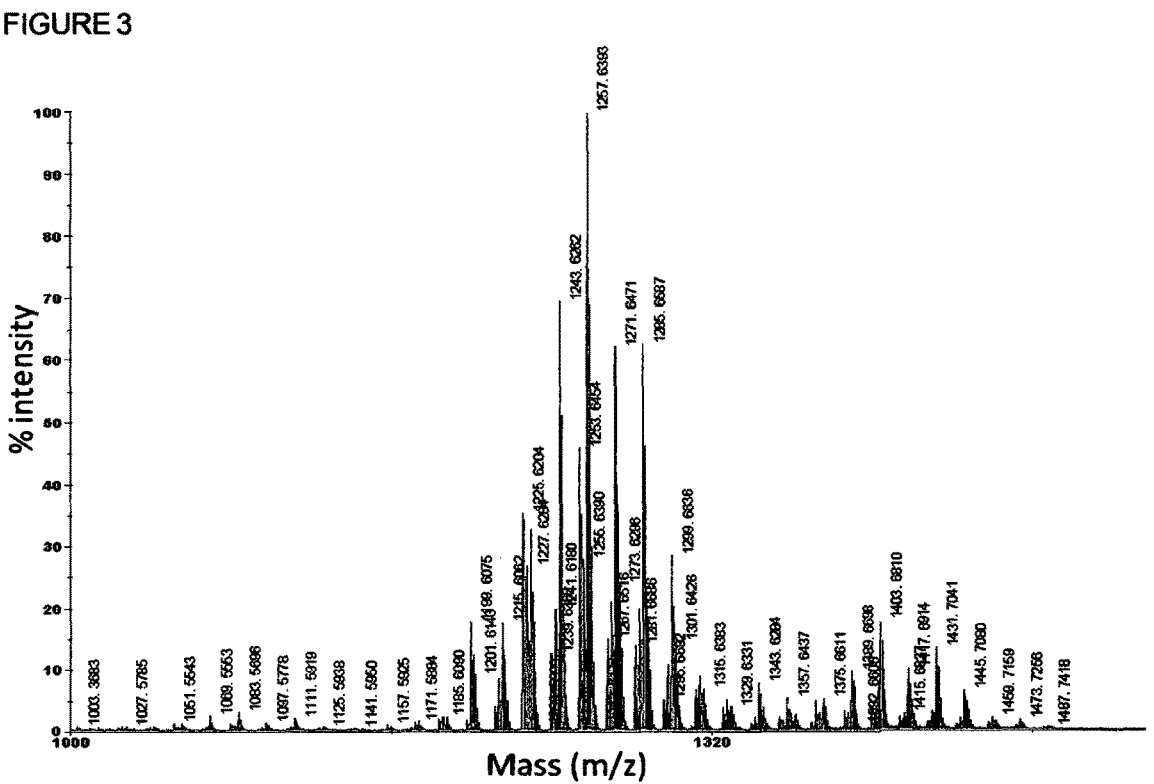
FIG. 3 shows a mass spectrum output having peaks of a twenty-fourth peak set (e.g. indicative for *M. bolletii*)
Figure 4:
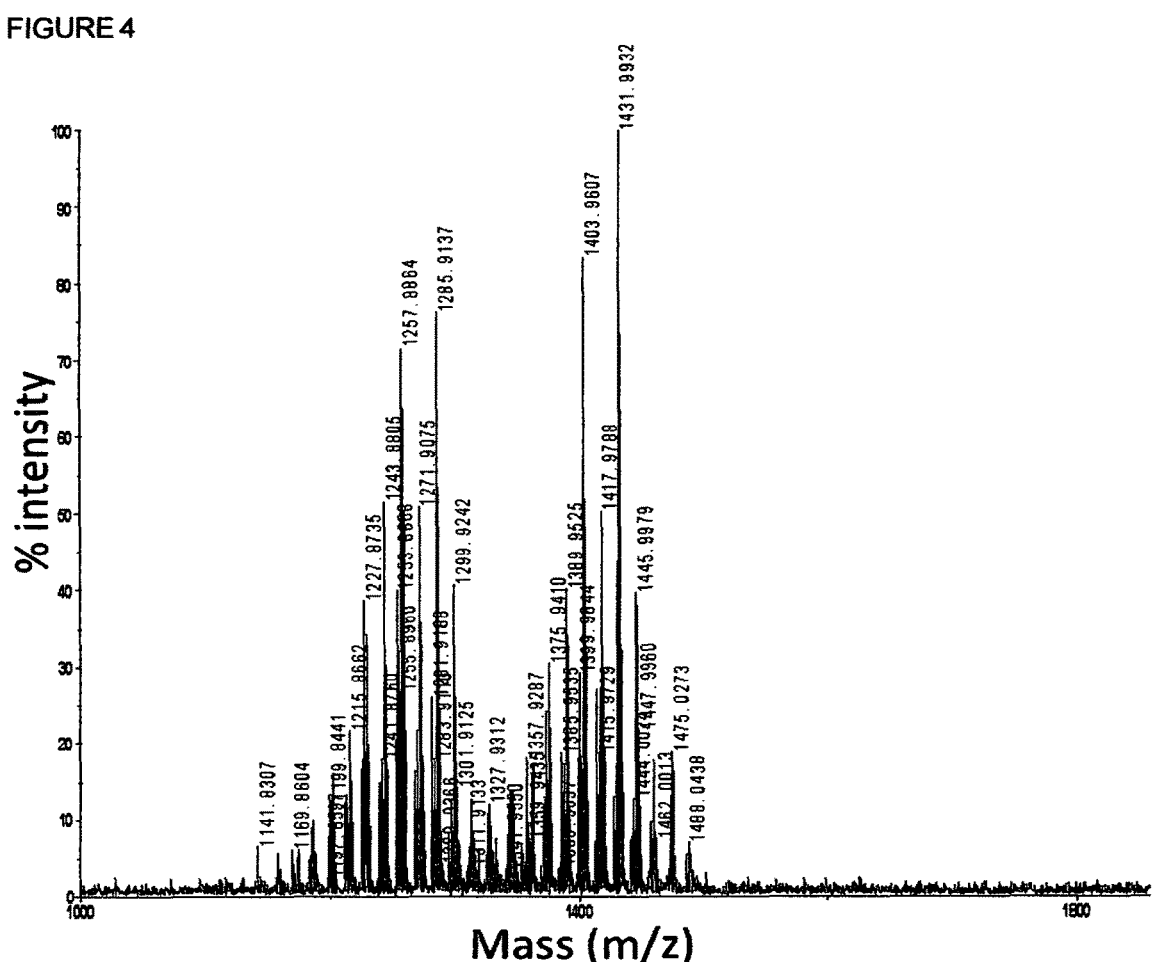
FIG. 4 shows a mass spectrum output having peaks of a first peak set (e.g. indicative for *M. abscessus*)
Figure 5:
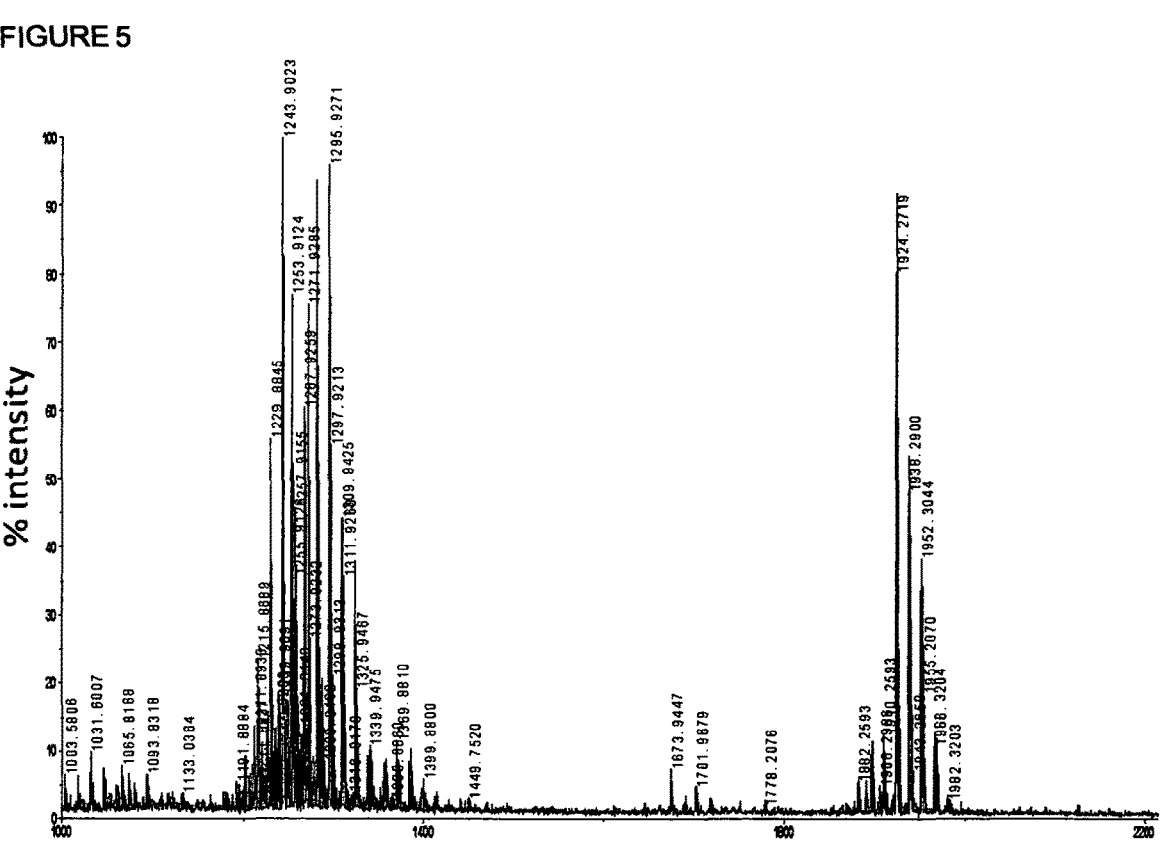
FIG. 5 shows a mass spectrum output having peaks of a third peak set (e.g. indicative for *M. avium*)
Figure 6:
FIG. 6 shows a mass spectrum output having peaks of a fourth peak set (e.g. indicative for *M. bohemicum*)
Figure 6:
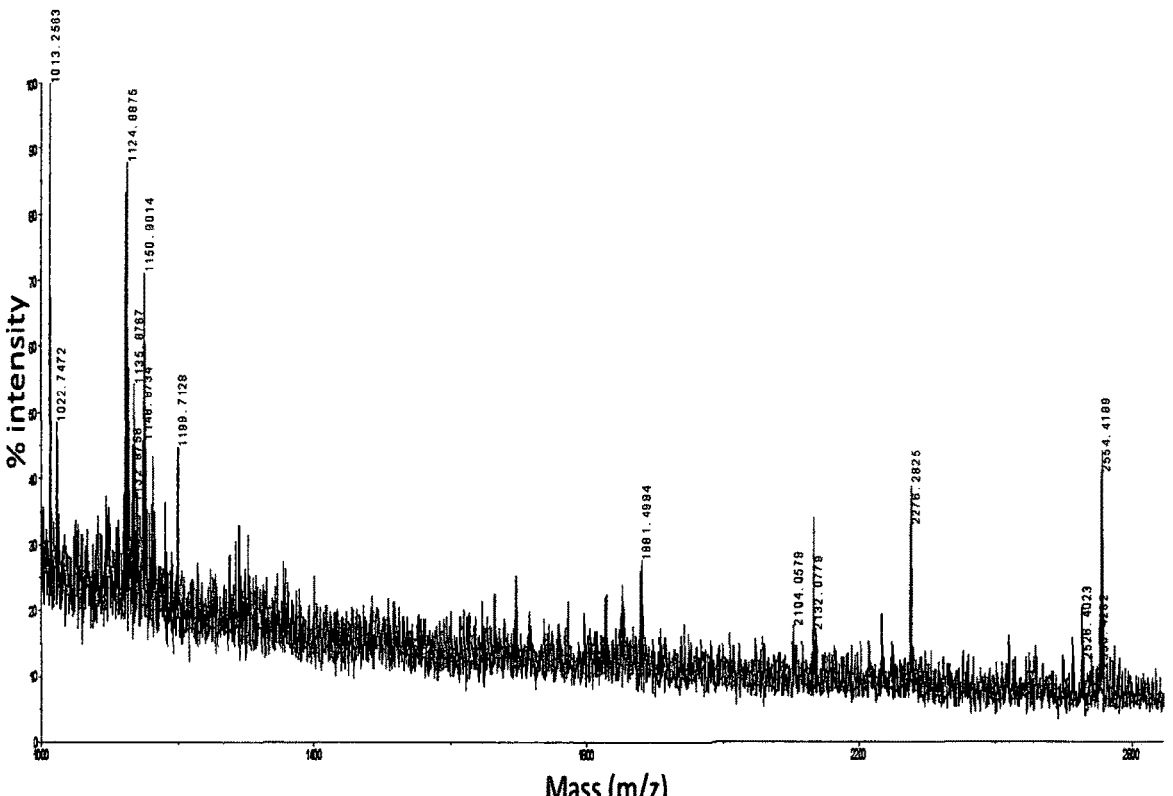
Figure 7:
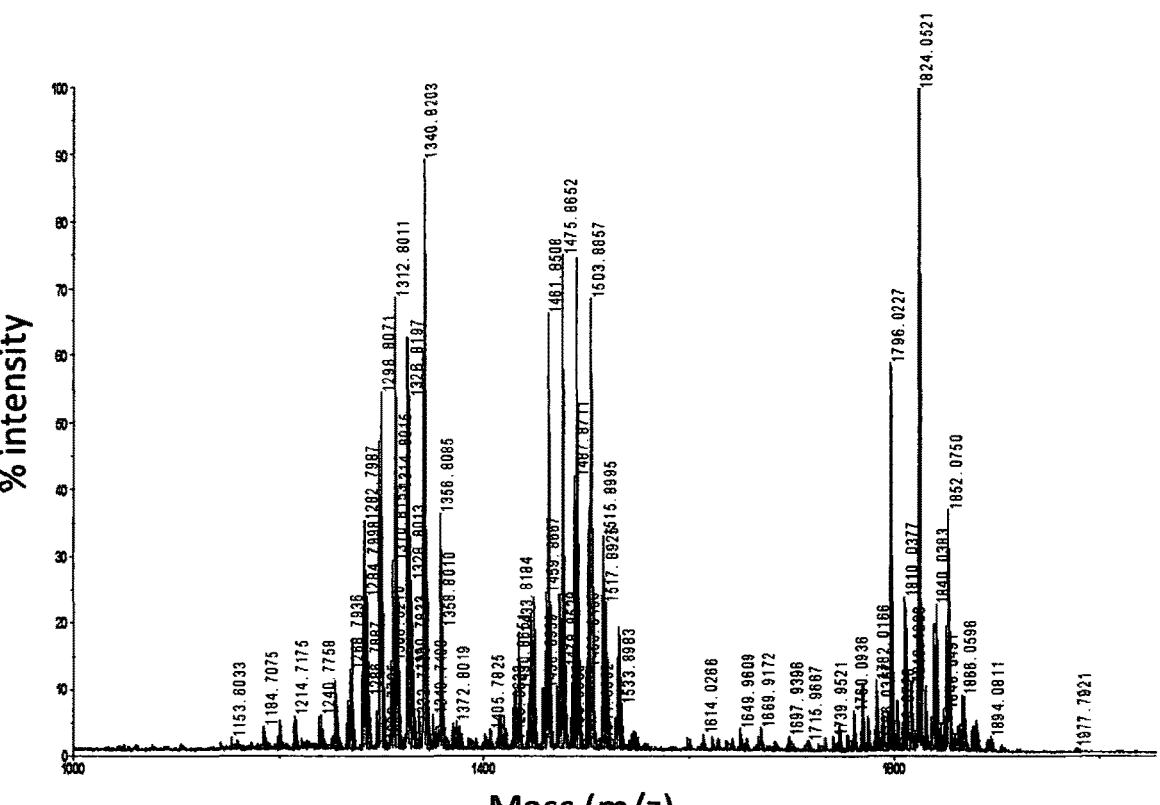
FIG. 7 shows a mass spectrum output having peaks of a fifth peak set (e.g. indicative for *M. celatum*)
Figure 8:
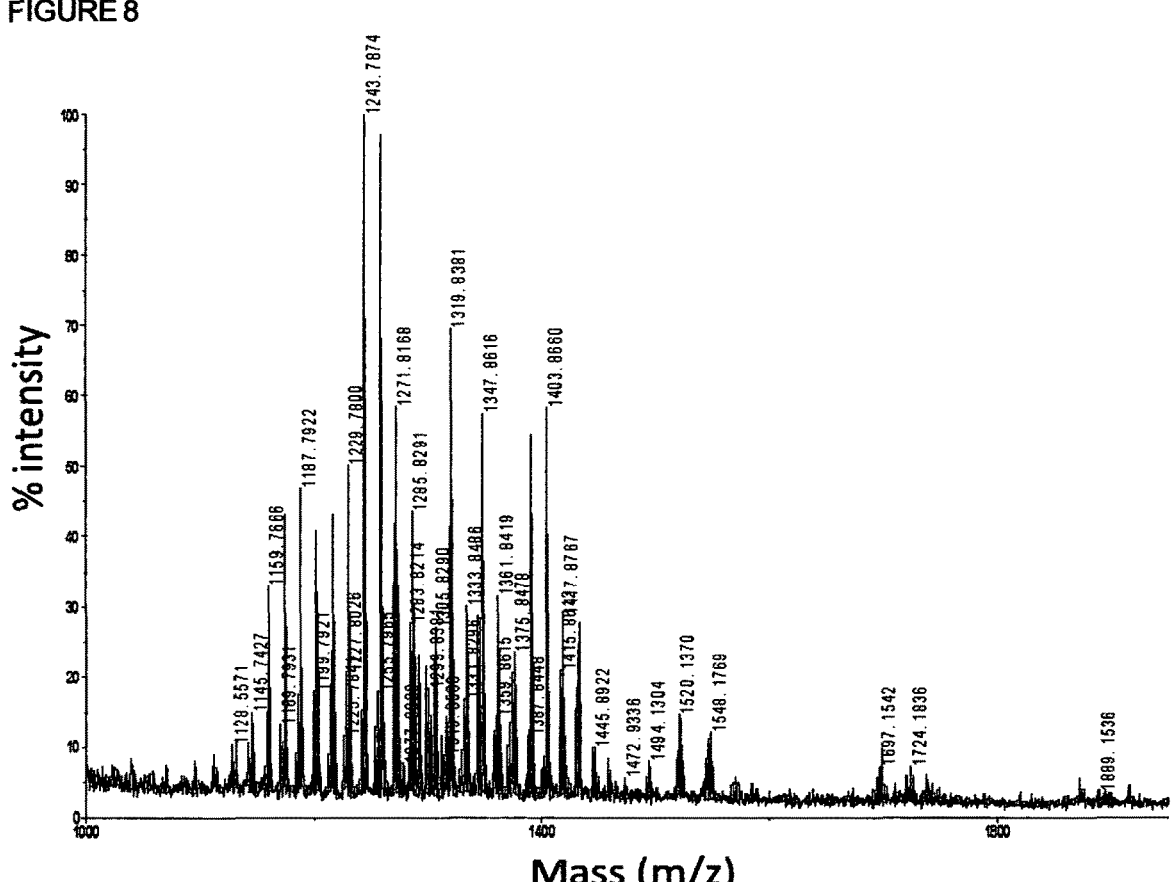
FIG. 8 shows a mass spectrum output having peaks of a sixth peak set (e.g. indicative for *M. chelonae*)
Figure 9:
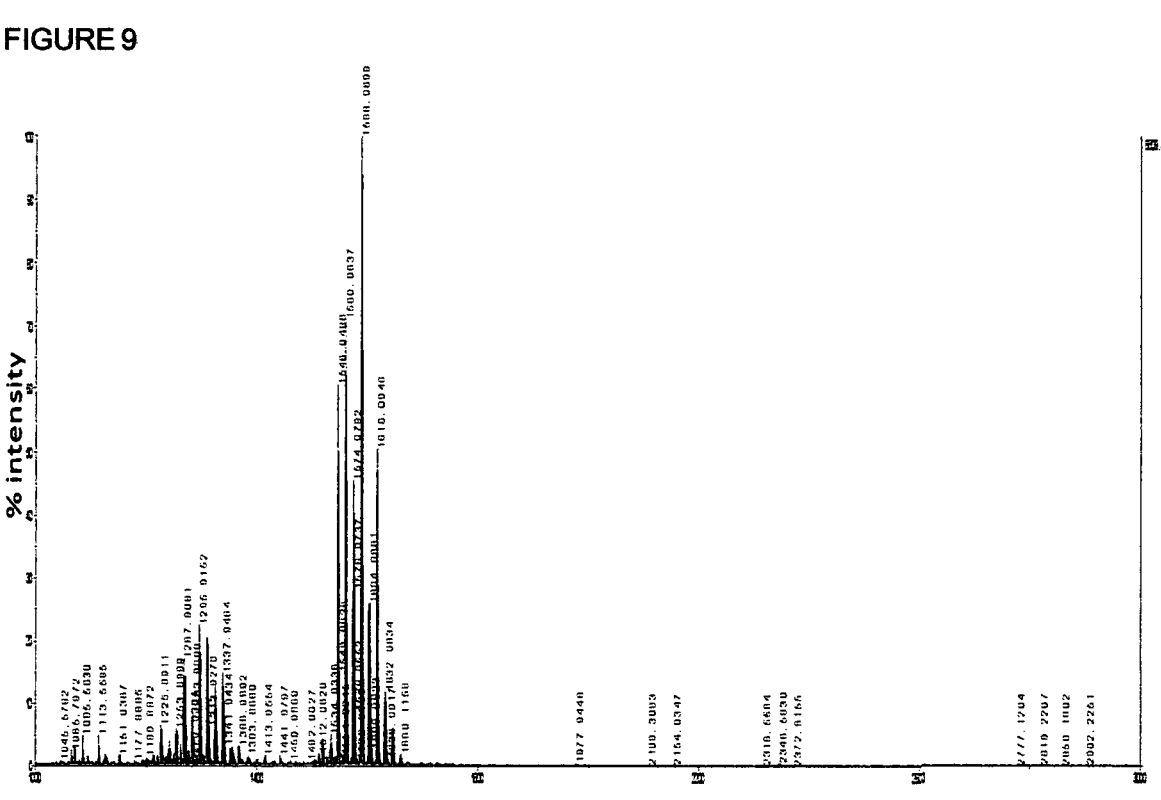
FIG. 9 shows a mass spectrum output having peaks of a seventh peak set (e.g. indicative for *M. chimaera* (BCCM, 130444))
Figure 10:
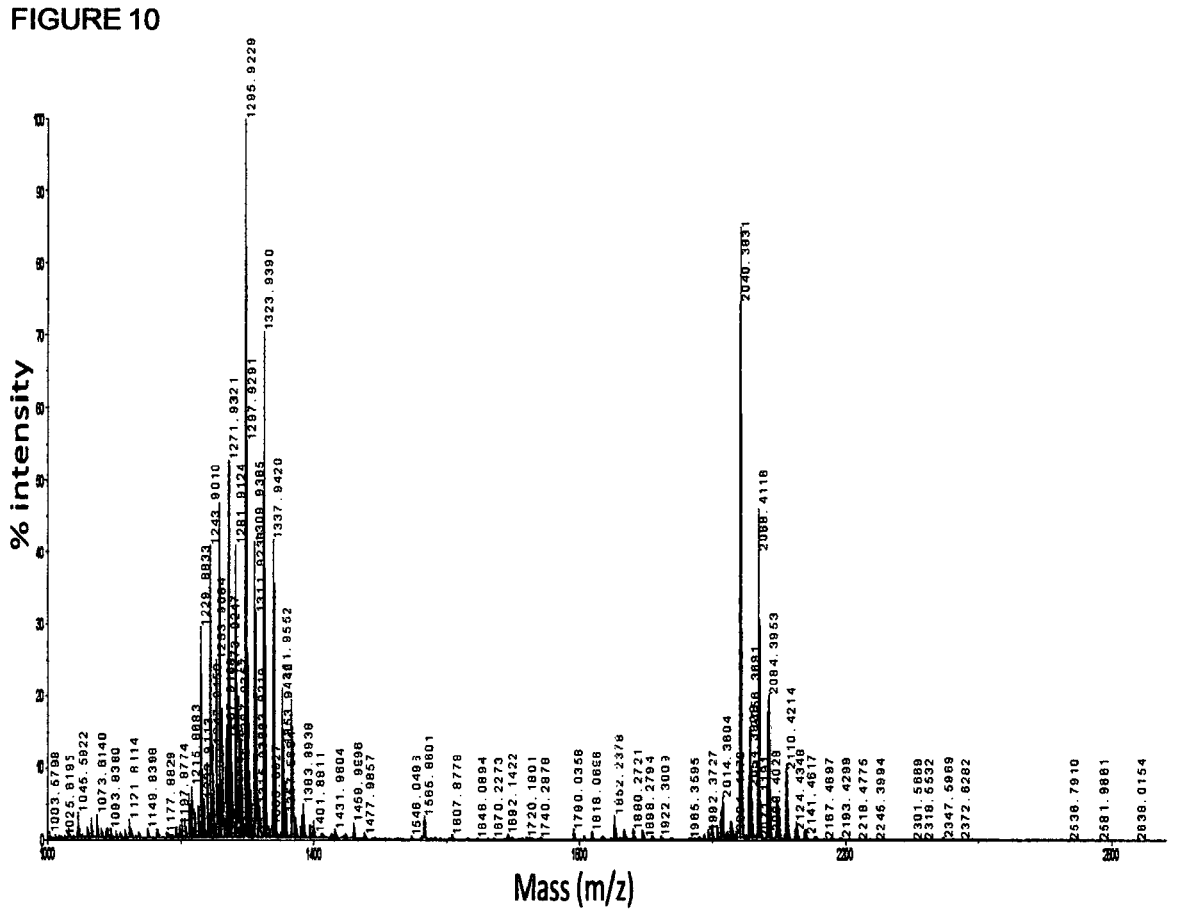
FIG. 10 shows a mass spectrum output having peaks of a seventh peak set (e.g. indicative for *M. chimaera* (BCCM 2015-01546))
Figure 11:
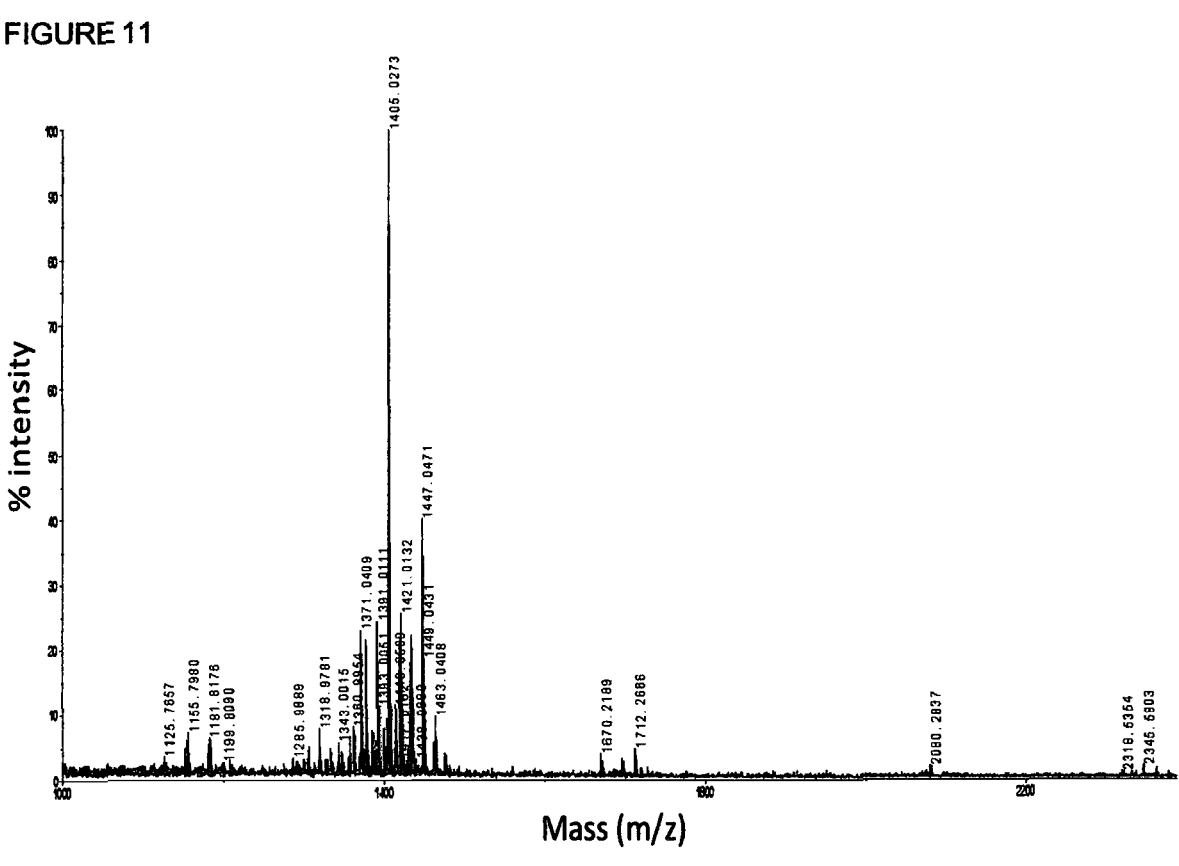
FIG. 11 shows a mass spectrum output having peaks of an eighth peak set (e.g. indicative for *M. fortuitum* (BCCM))
Figure 12:
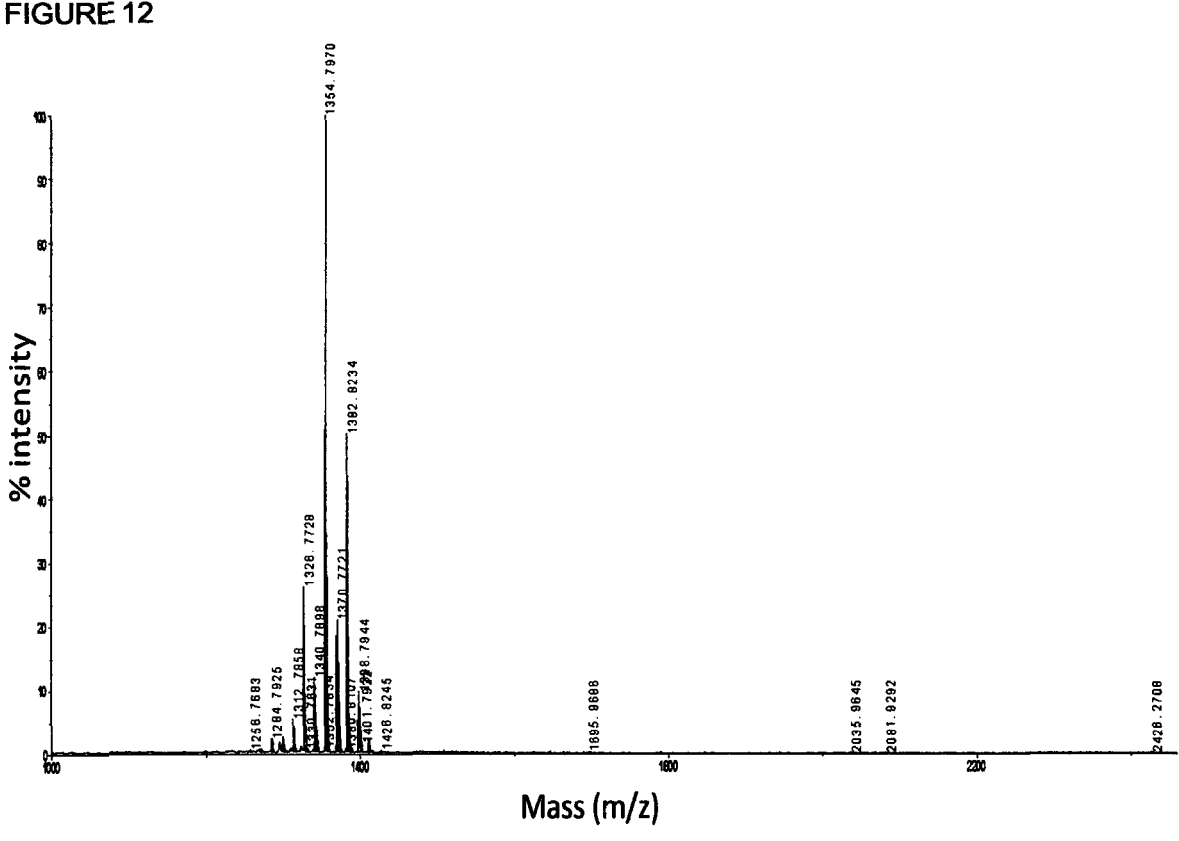
FIG. 12 shows a mass spectrum output having peaks of an eighth peak set (e.g. indicative for *M. fortuitum* (ECDC))
Figure 13:
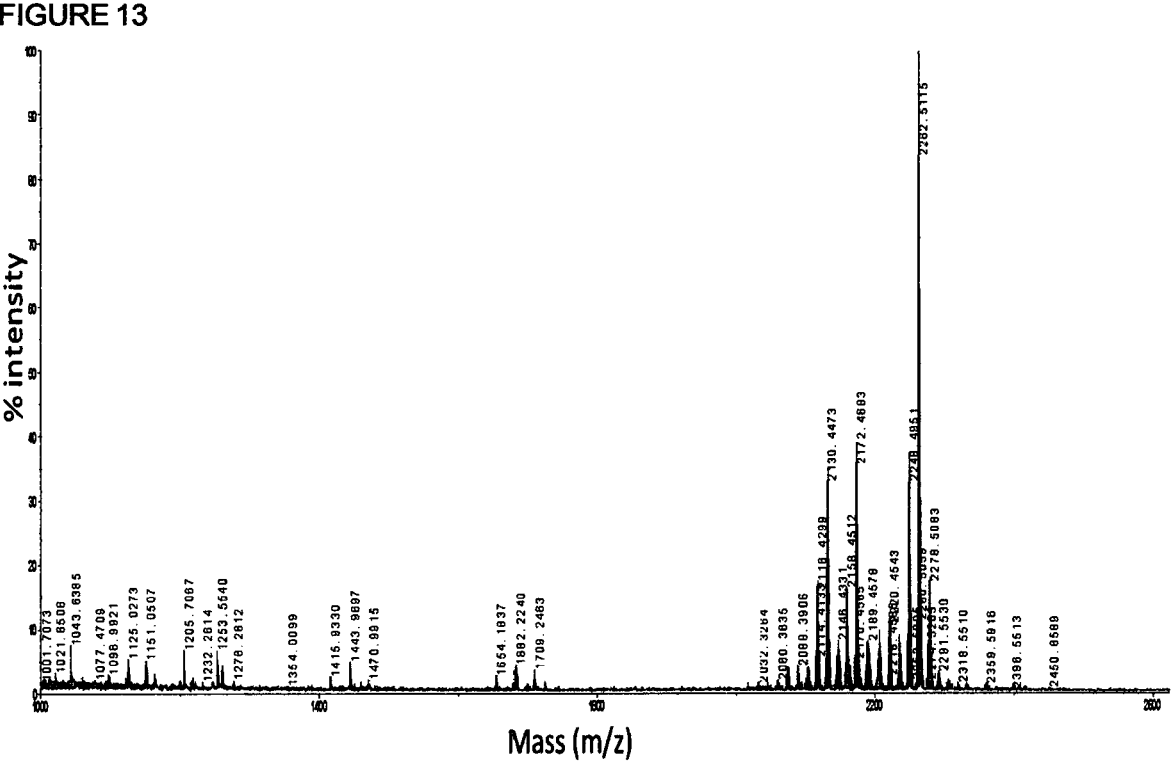
FIG. 13 shows a mass spectrum output having peaks of a ninth peak set (e.g. indicative for *M. gordonae*)
Figure 14:
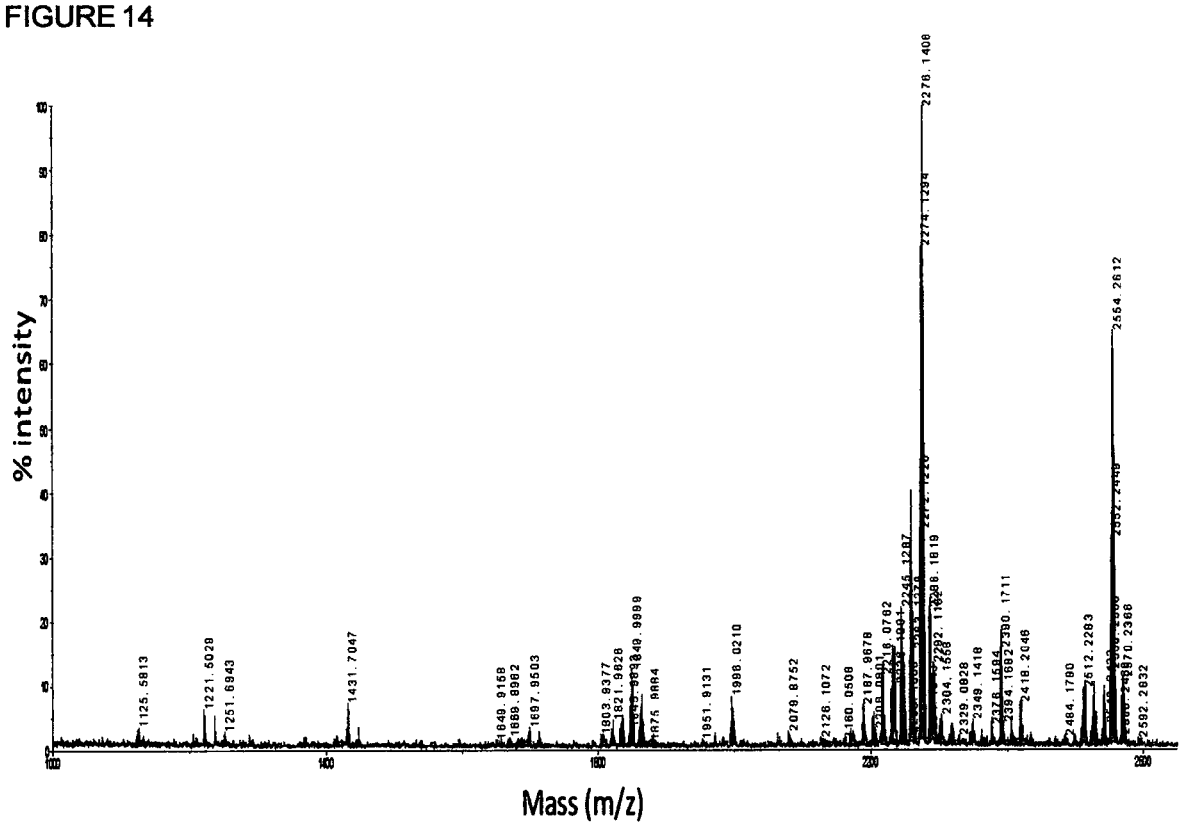
FIG. 14 shows a mass spectrum output having peaks of a tenth peak set (e.g. indicative for *M. interjectum*)
Figure 15:
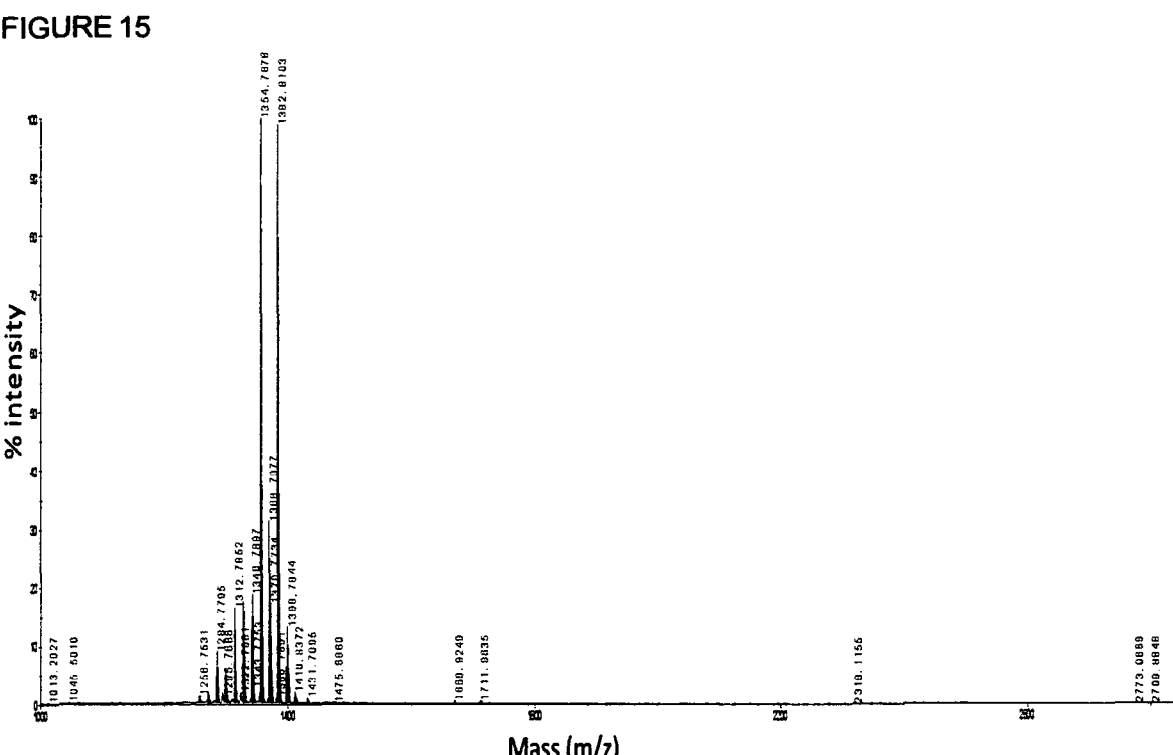
FIG. 15 shows a mass spectrum output having peaks of an eleventh peak set (e.g. indicative for *M. intermedium*)
Figure 16:
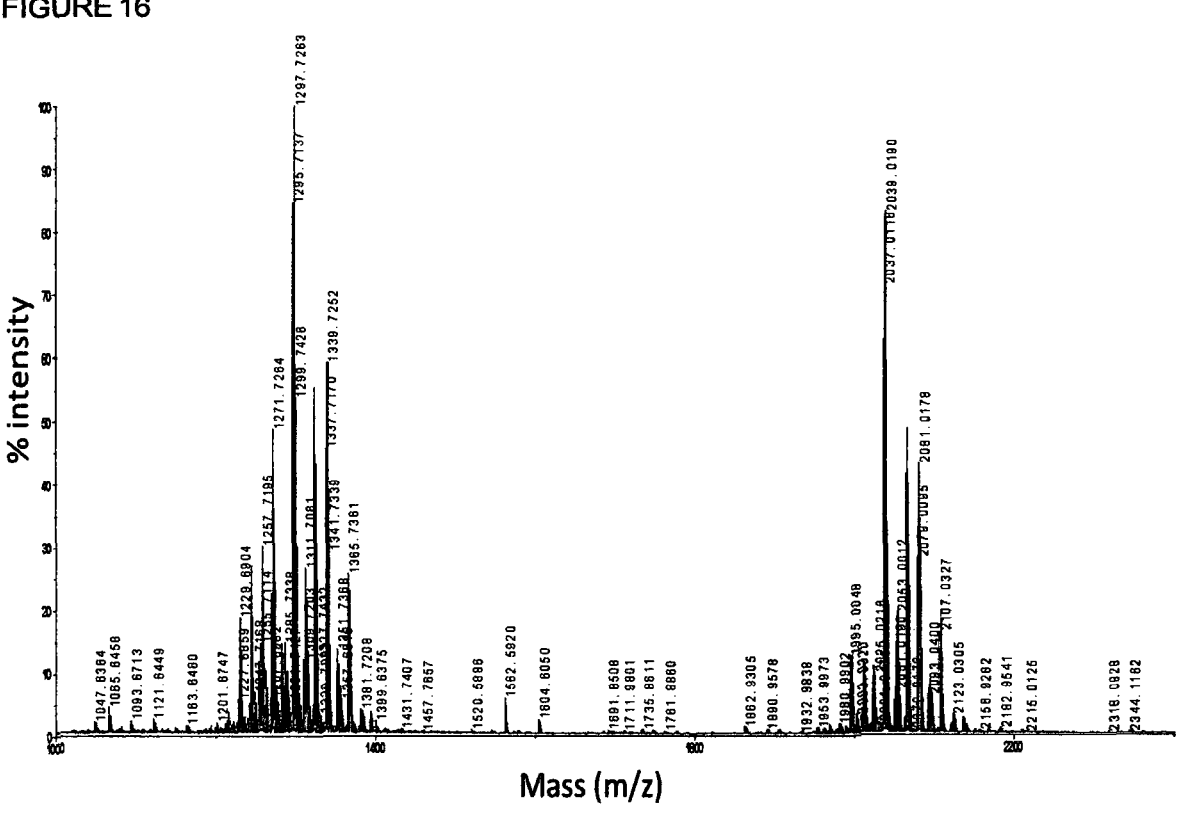
FIG. 16 shows a mass spectrum output having peaks of a twelfth peak set (e.g. indicative for *M. intracellulare* (ECDC))
Figure 17:
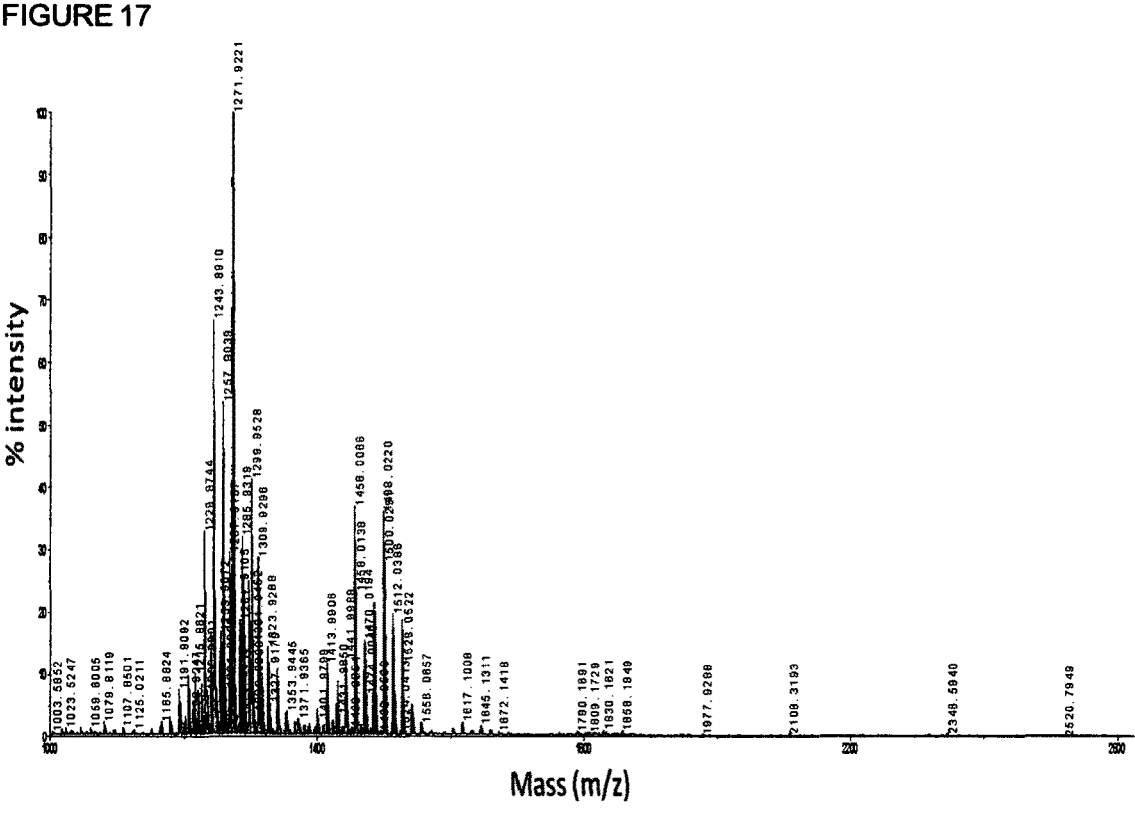
FIG. 17 shows a mass spectrum output having peaks of a twelfth peak set (e.g. indicative for *M. intracellulare* (BCCM))
Figure 18:
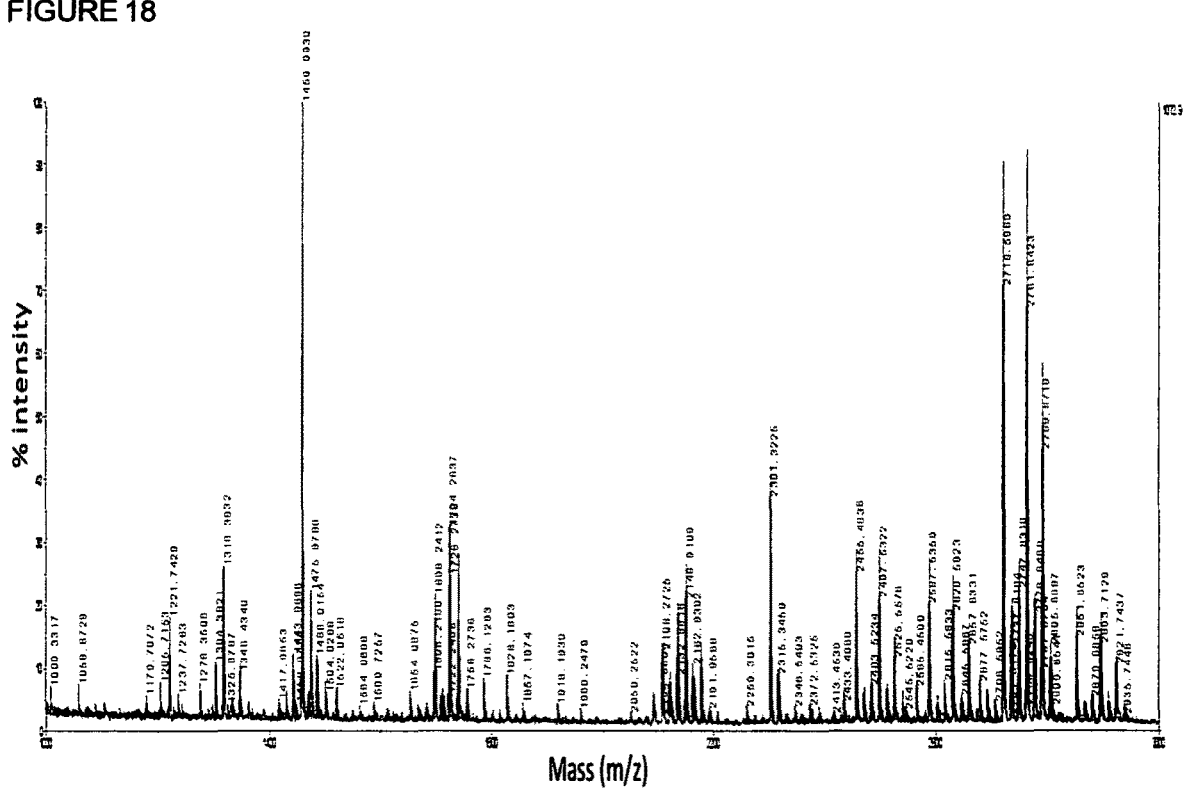
FIG. 18 shows a mass spectrum having peaks of a thirteenth peak set (e.g. output indicative for *M. kansasii*)
Figure 19:
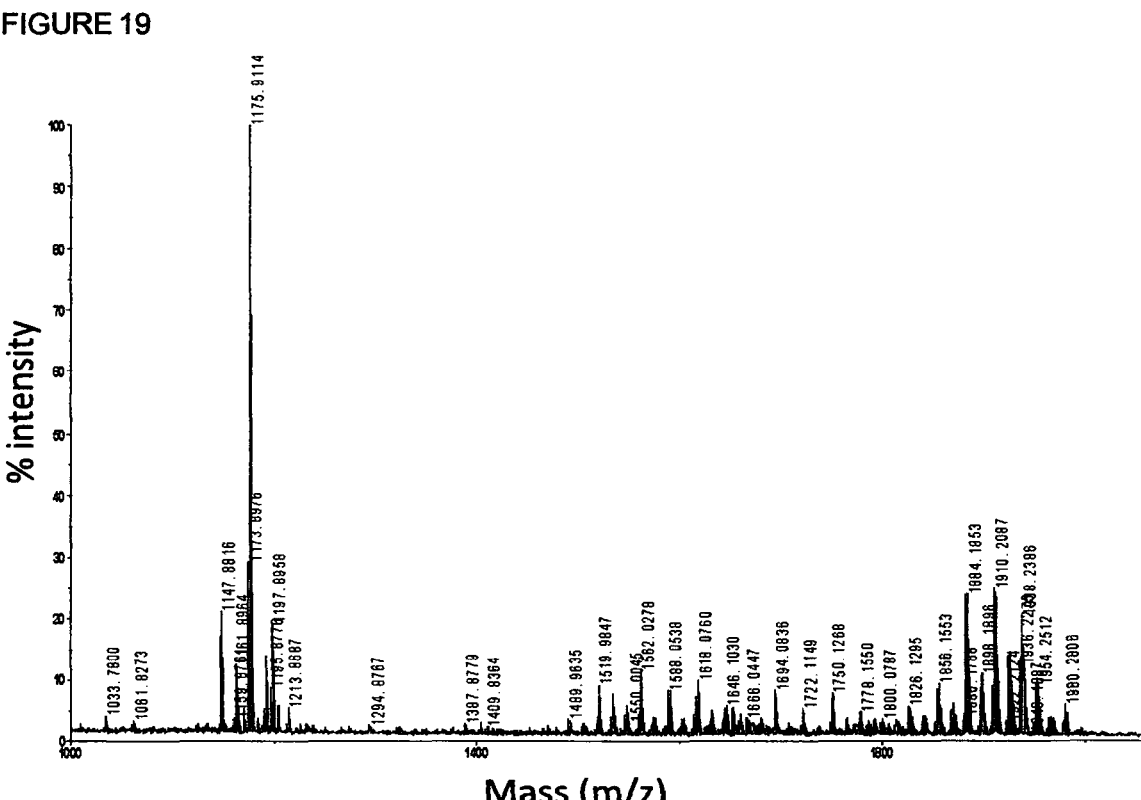
FIG. 19 shows a mass spectrum output having peaks of a fourteenth peak set (e.g. indicative for *M. marinum*)
Figure 20:
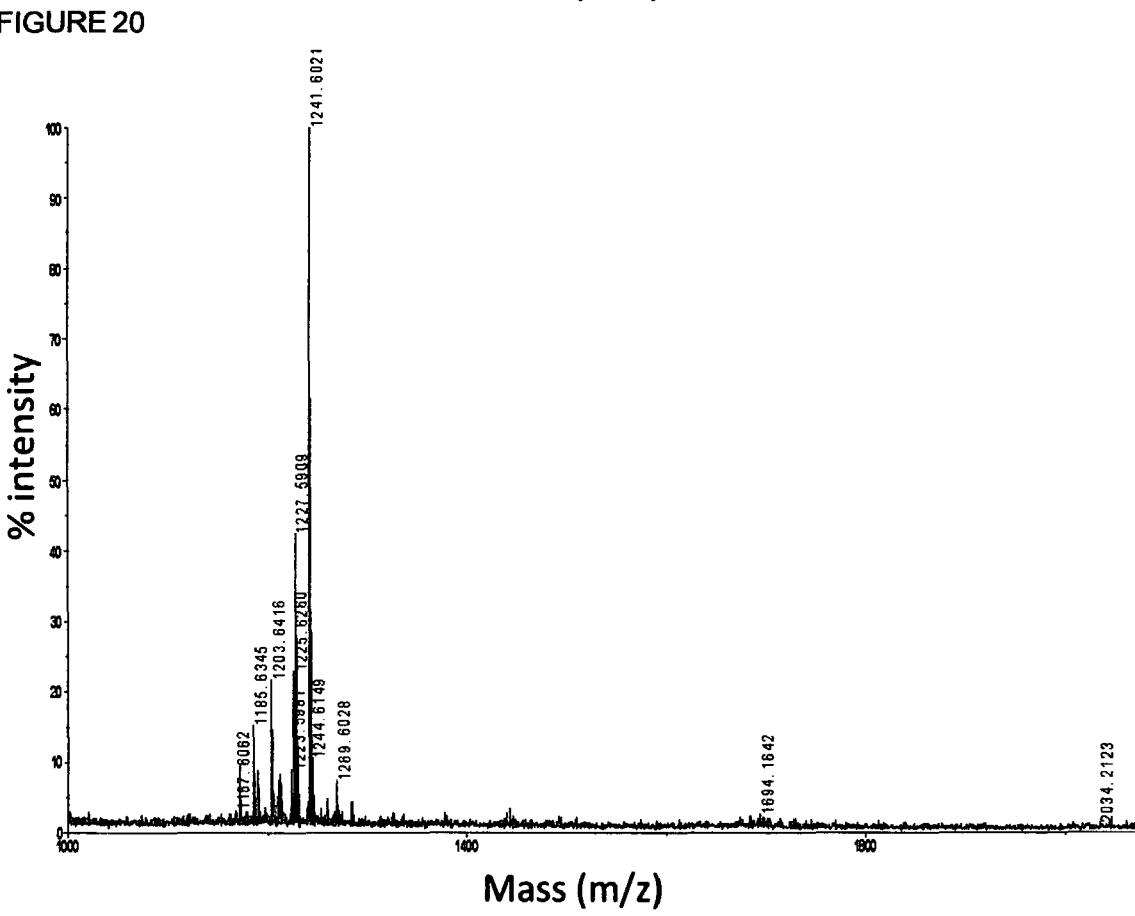
FIG. 20 shows a mass spectrum output having peaks of a fifteenth peak set (e.g. indicative for *M. nonchromogenicum*)
Figure 21:
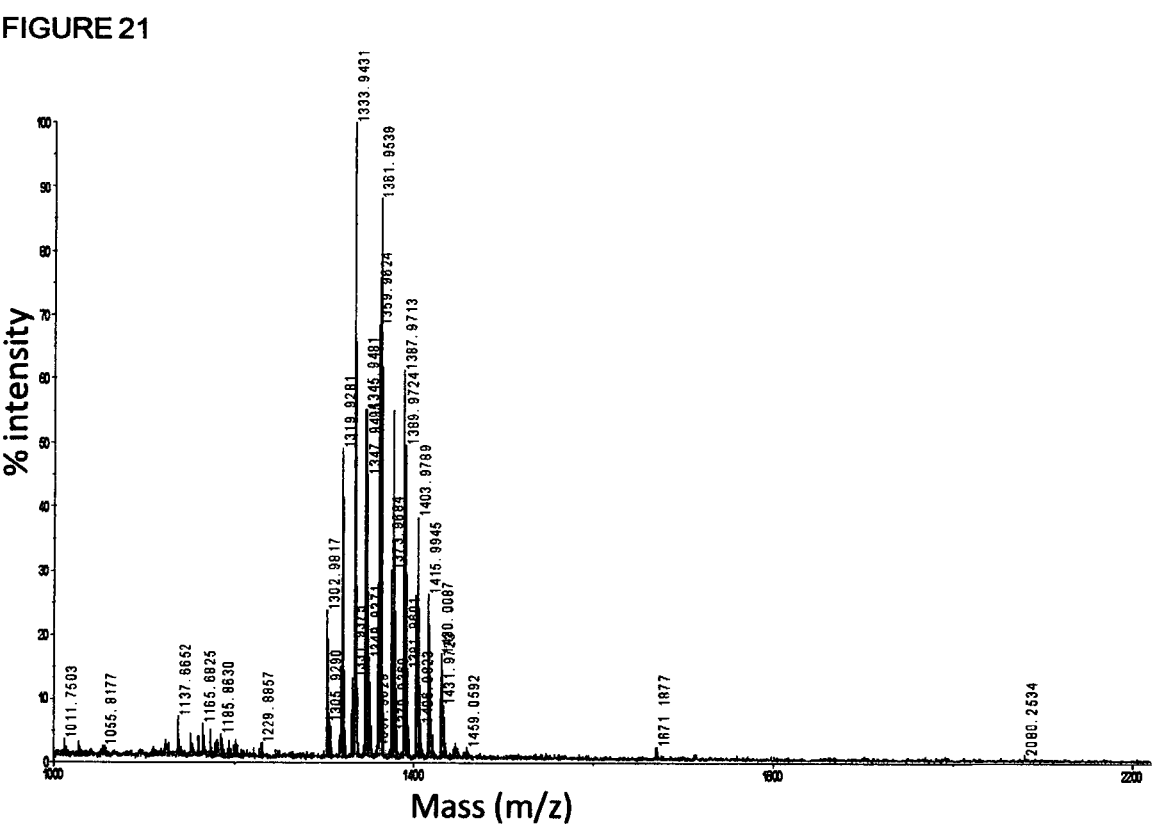
FIG. 21 shows a mass spectrum output having peaks of a sixteenth peak set (e.g. indicative for *M. peregrinum* (BOOM))
Figure 22:
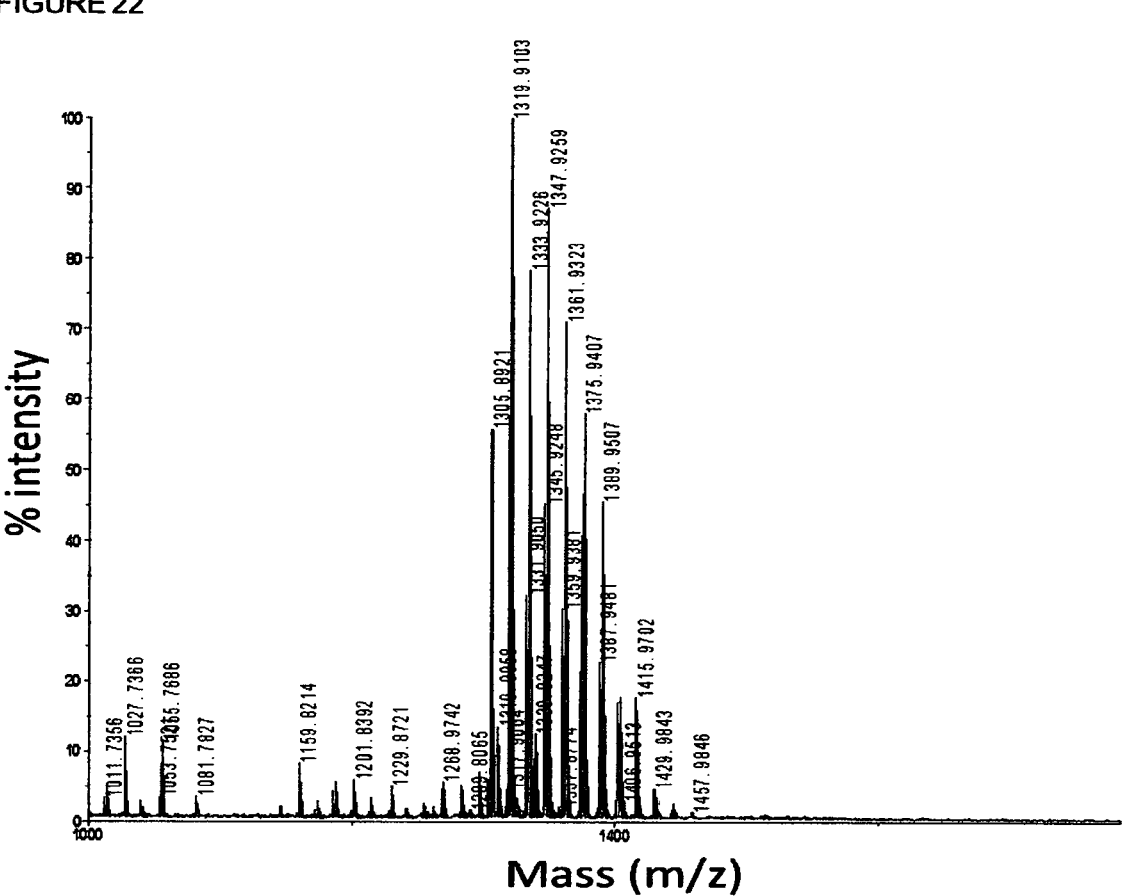
FIG. 22 shows a mass spectrum output having peaks of a sixteenth peak set (e.g. indicative for *M. peregrinum* (ECDC))
Figure 23:
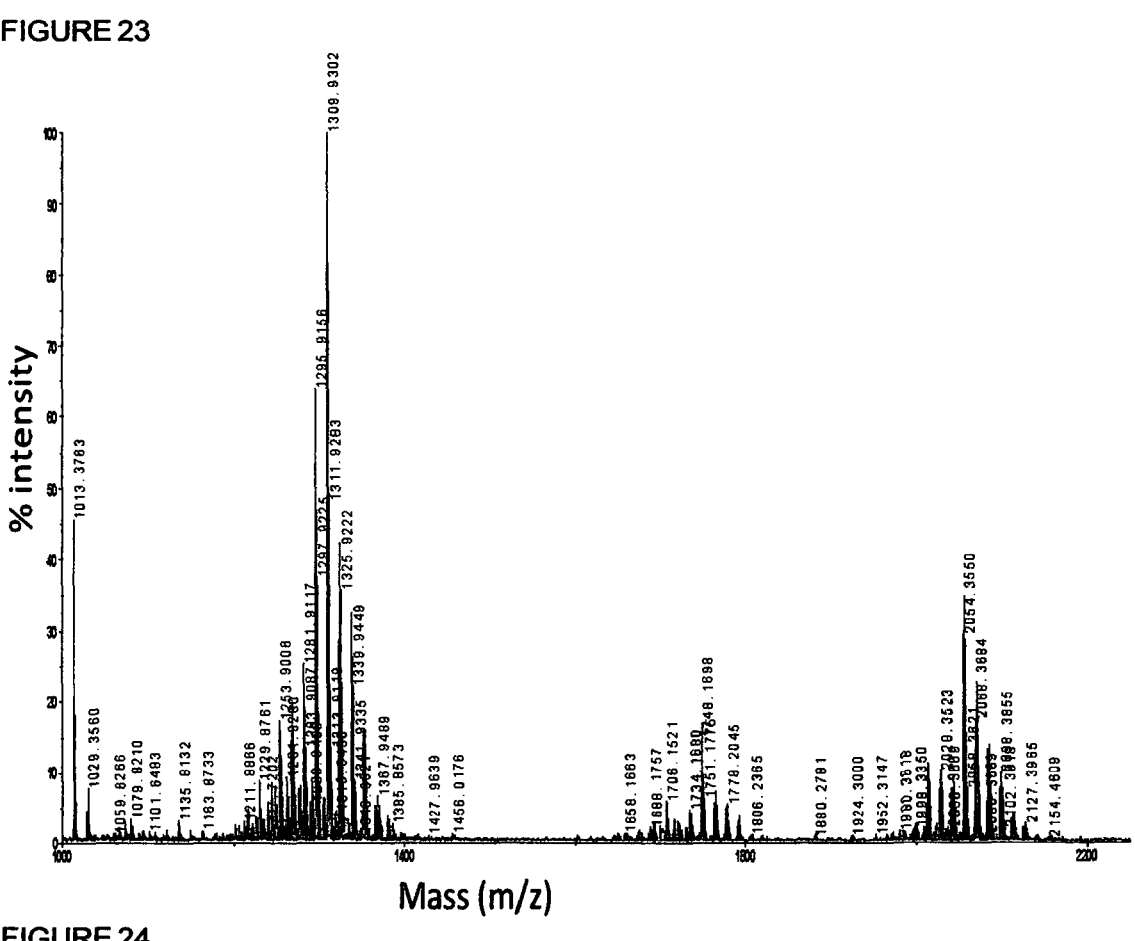
FIG. 23 shows a mass spectrum output having peaks of a seventeenth peak set (e.g. indicative for *M. scrofulaceum* (BOOM))
Figure 24:
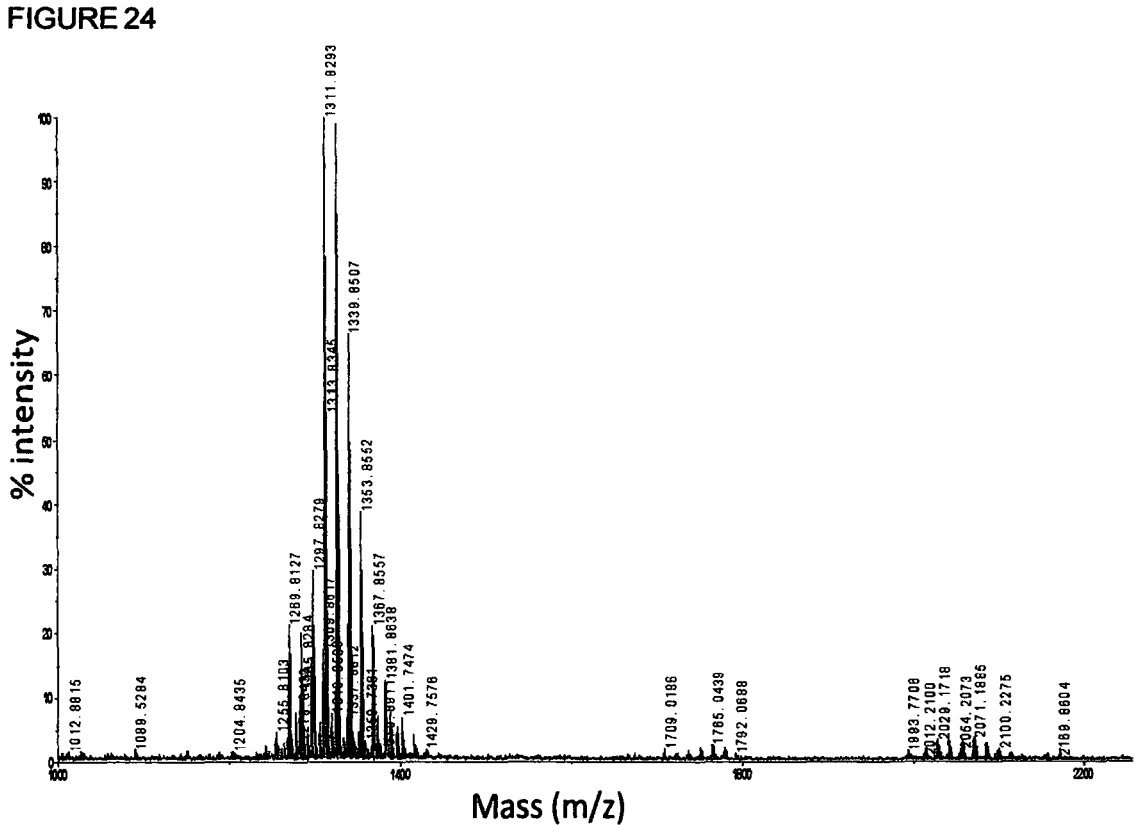
FIG. 24 shows a mass spectrum output having peaks of a seventeenth peak set (e.g. indicative for *M. scrofulaceum* (ECDC))
Figure 25:
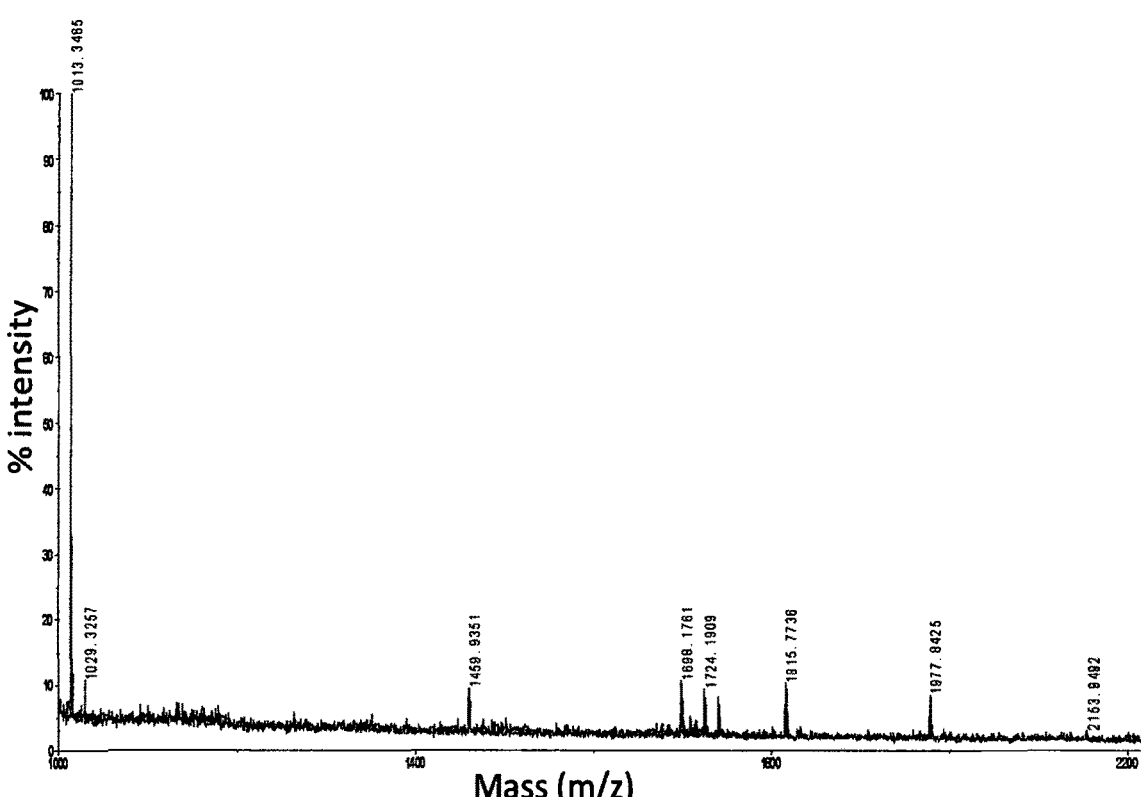
FIG. 25 shows a mass spectrum output having peaks of an eighteenth peak set (e.g. indicative for *M. shimoidei*)
Figure 26:
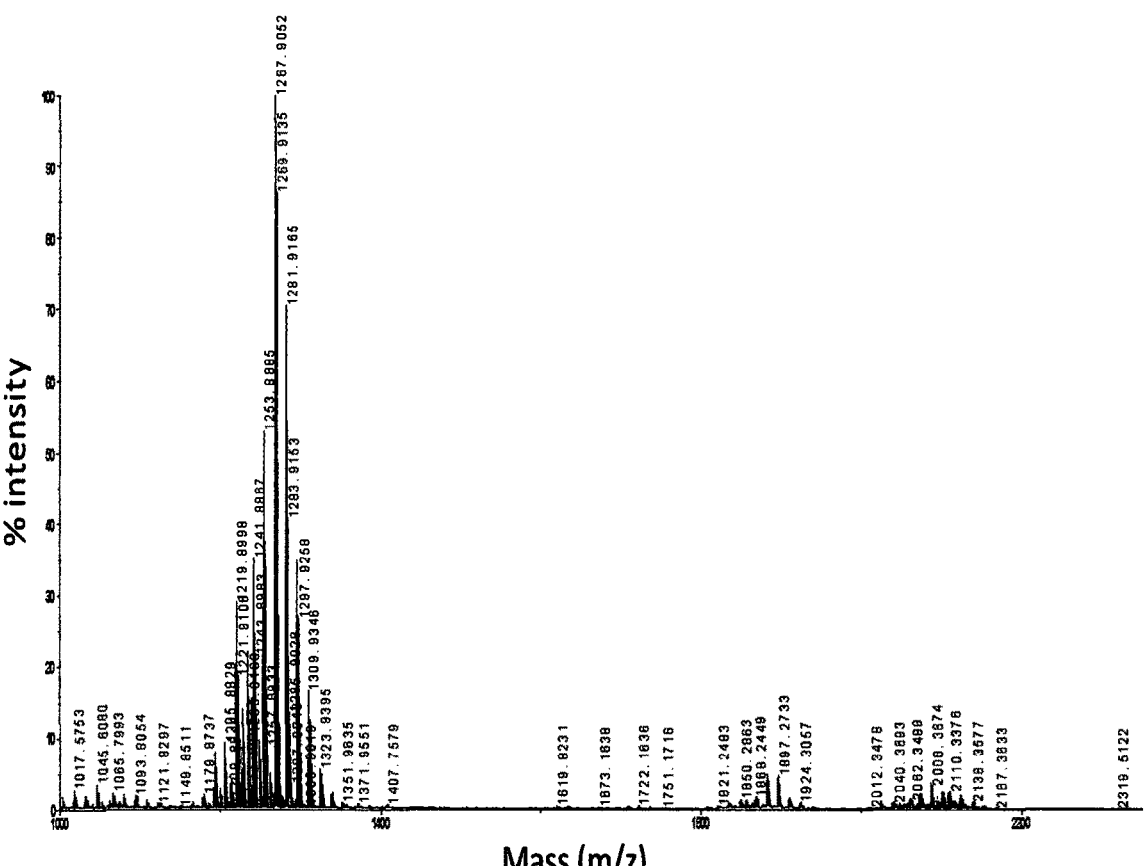
FIG. 26 shows a mass spectrum output having peaks of a nineteenth peak set (e.g. indicative for *M. simiae* (BOOM))
Figure 27:
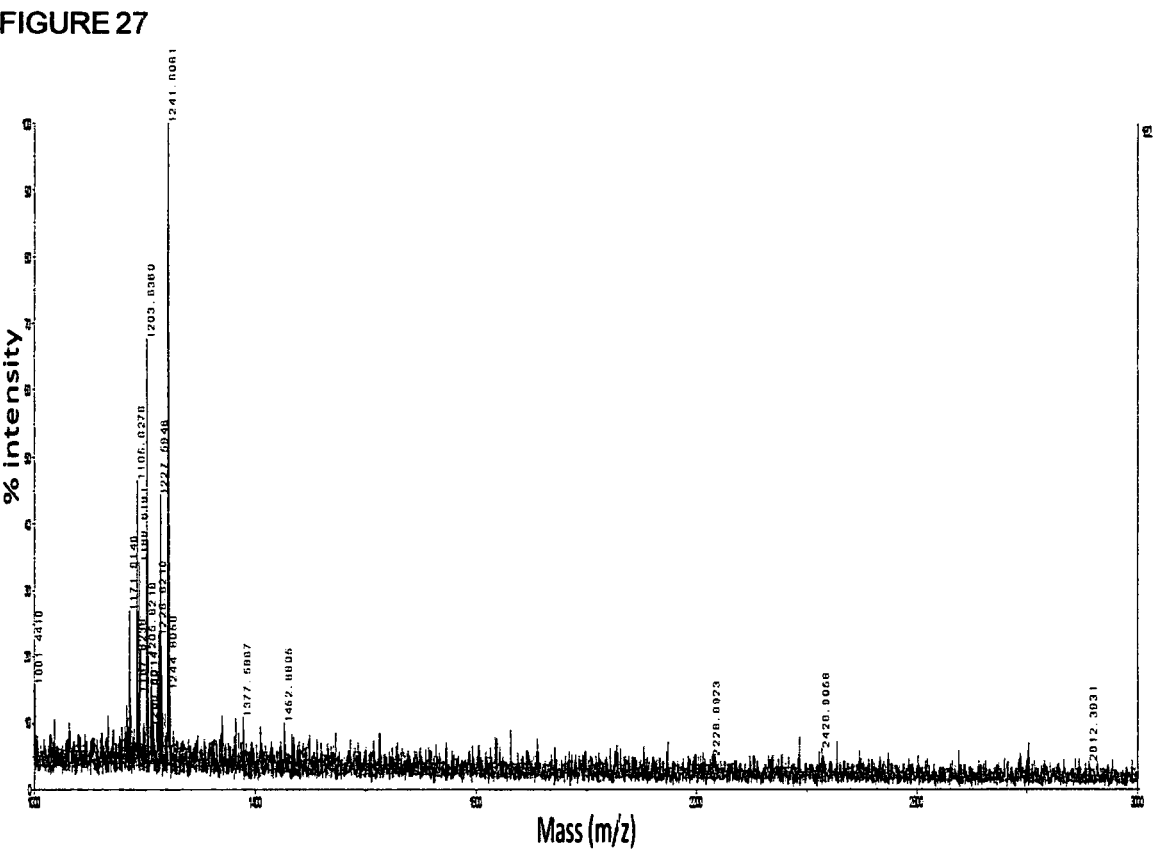
FIG. 27 shows a mass spectrum output having peaks of a nineteenth peak set (e.g. indicative for *M. simiae* (ECDC))
Figure 28:
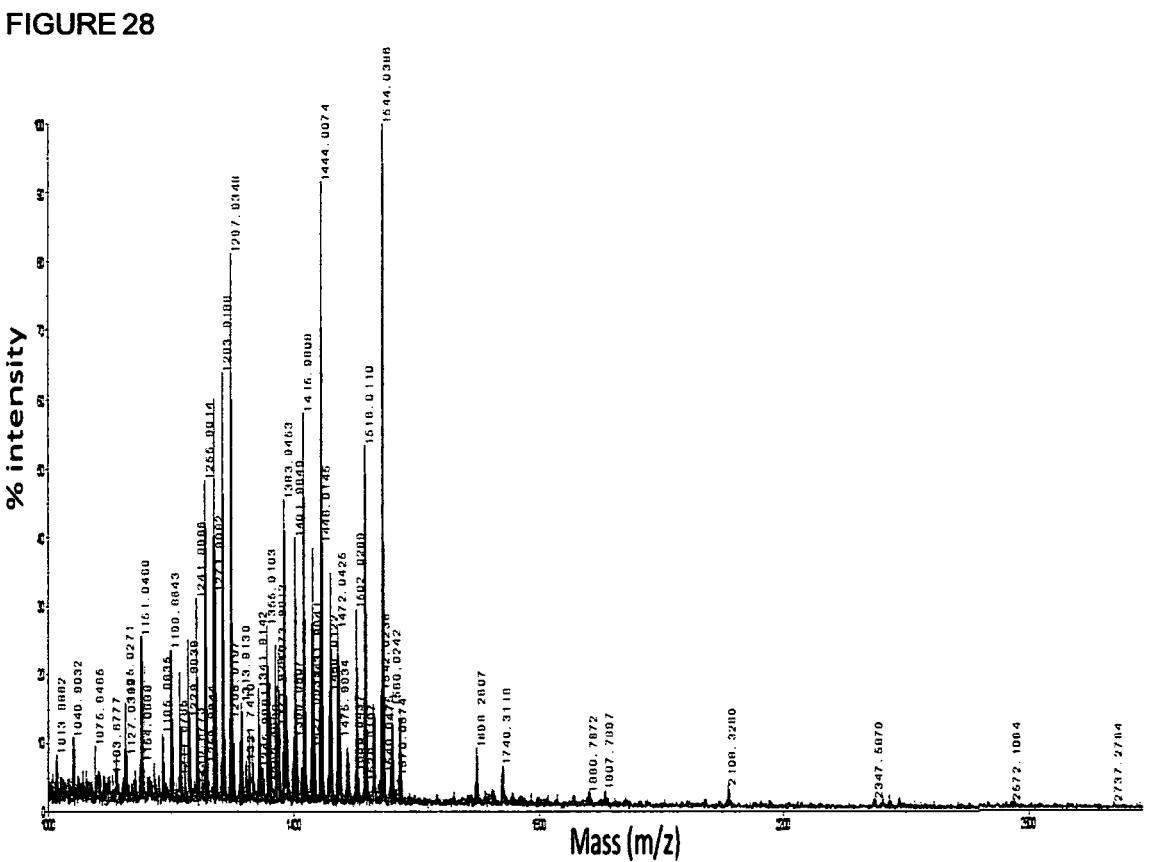
Figure 29:
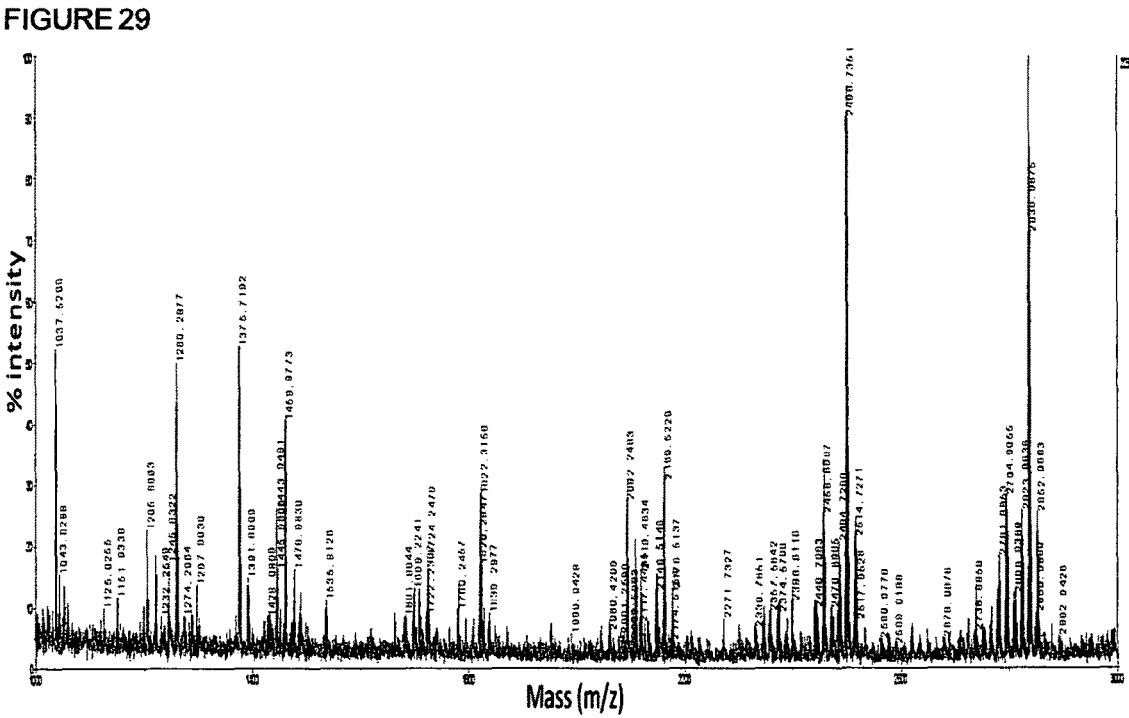
Figure 30:
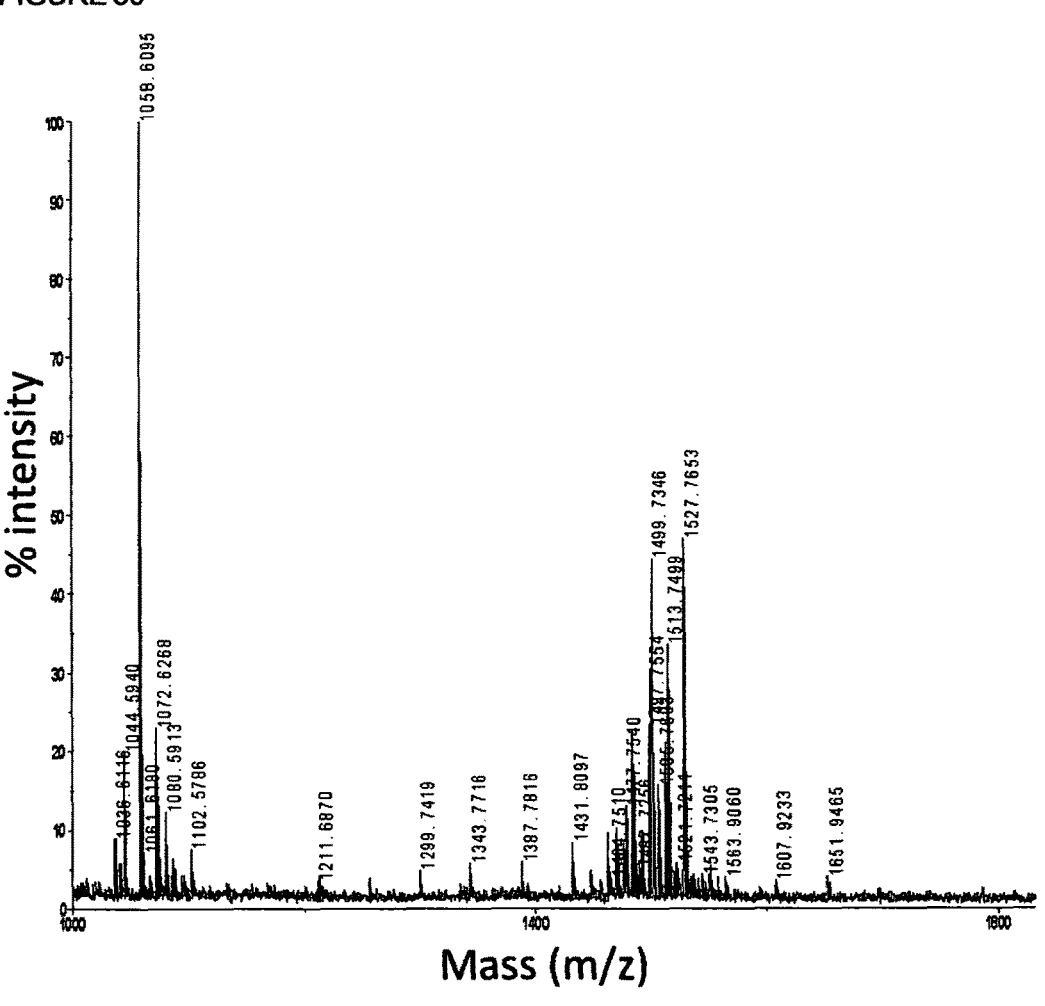
Figure 31:
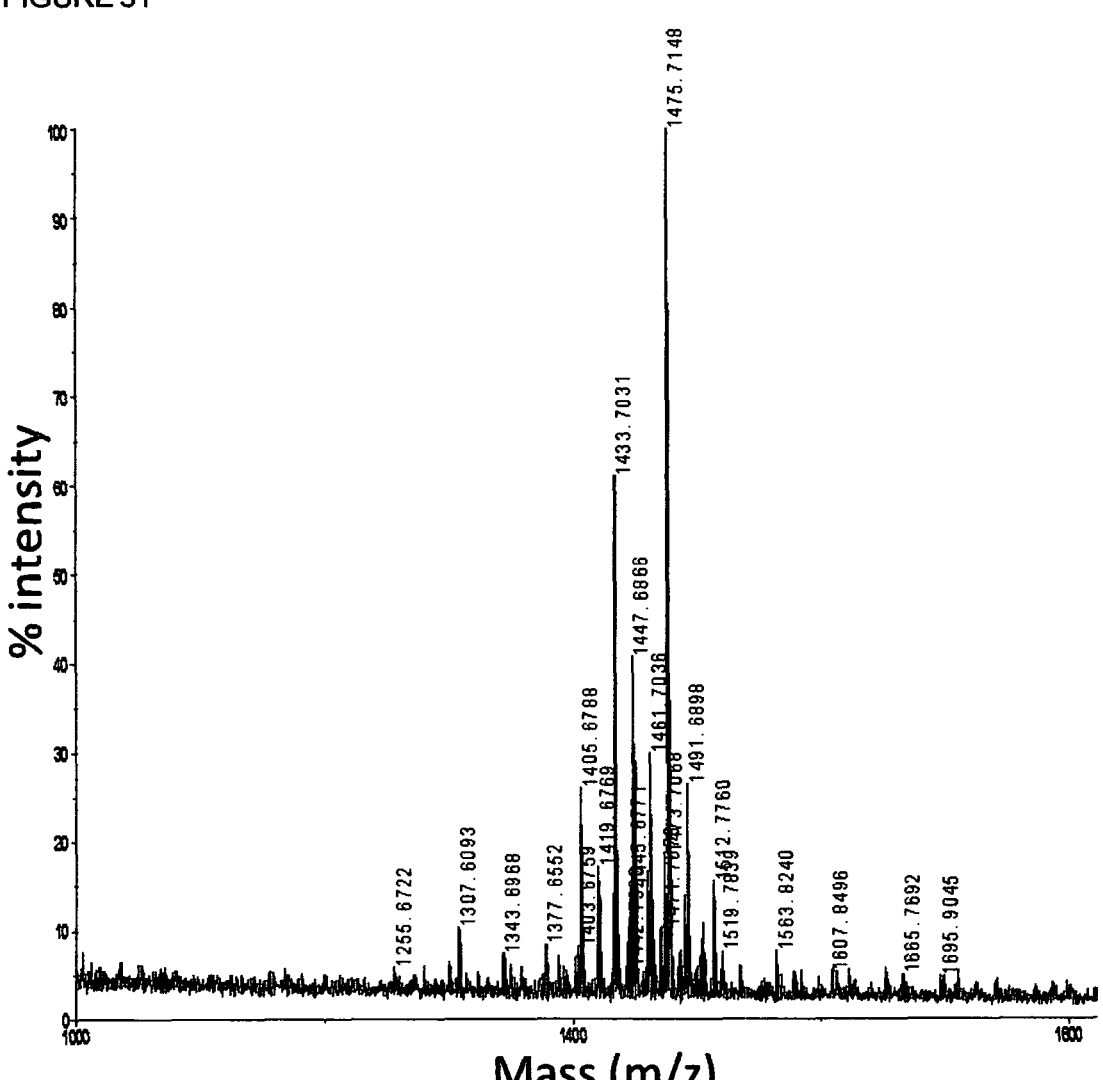

FIG. 28 shows a mass spectrum output having peaks of a twentieth peak set (e.g. indicative for *M. smegmatis*);

FIG. 29 shows a mass spectrum output having peaks of a twenty-first peak set (e.g. indicative for *M. szulgai*);

FIG. 30 shows a mass spectrum output having peaks of a twenty-second peak set (e.g. indicative for *M. ulcerans*);

FIG. 31 shows a mass spectrum output having peaks of a twenty-third peak set (e.g. indicative for *M. xenopi*).

Figure 32:
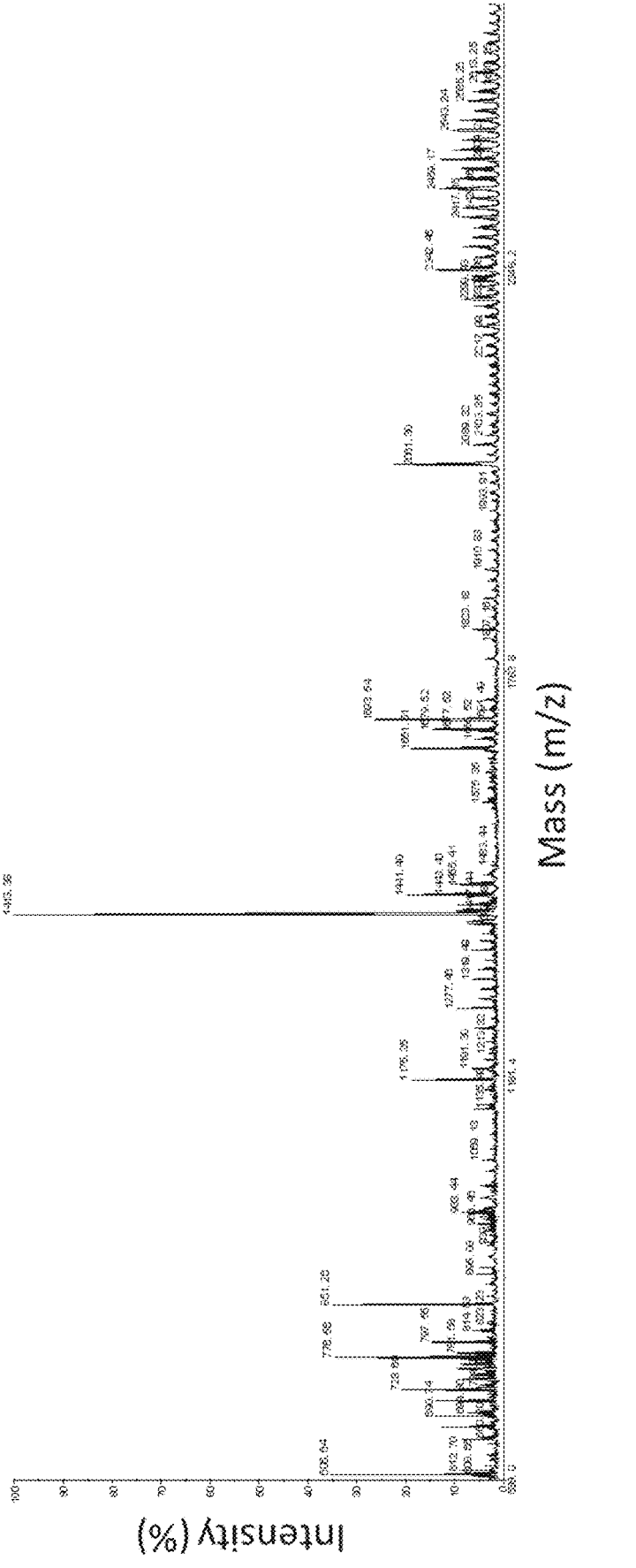
Figure 33:
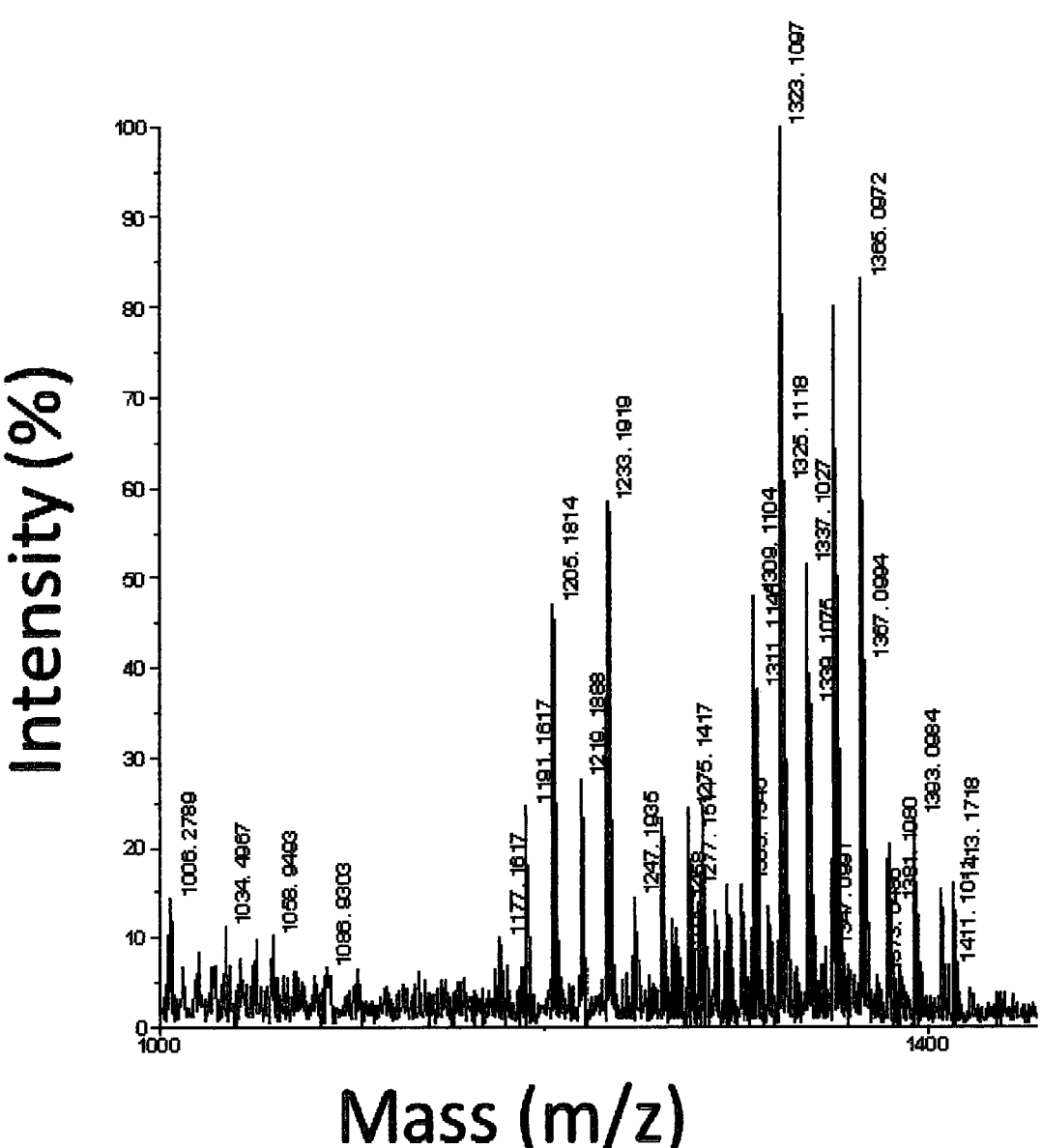
Figure 34:
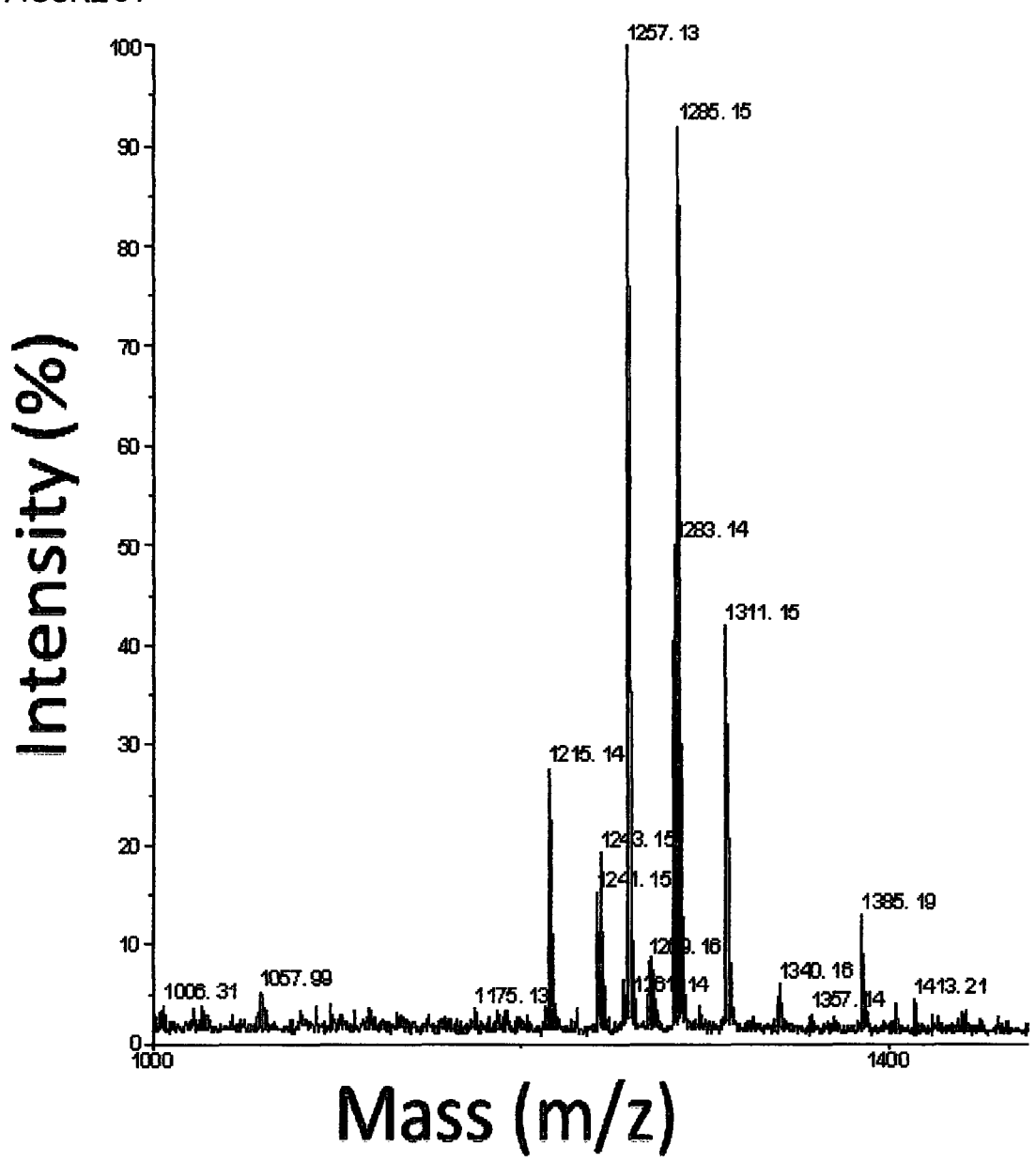
FIG. 34 shows a mass spectrum output (negative ion mode) having peaks of a fortieth peak set (e.g. indicative for *M. peregrinum*)

FIG. 32 shows a mass spectrum output (negative ion mode) having peaks of a thirty-eighth peak set (e.g. indicative for *M. tuberculosis* H37Rv);

FIG. 33 shows a mass spectrum output (negative ion mode) having peaks of a thirty-ninth peak set (e.g. indicative for *M. avium* serovar 4);

The lyophilized BCCM strains were revived by re-suspending in a small amount (~10 μL) of liquid medium, Middlebrook 7H9 (Sigma Aldrich). All isolates were incubated in 5 mL of 7H9 with OADC (oleic acid-albumin-dextrose-catalase) for 2-4 weeks and then 1 ml of bacterial biomass of each strain was frozen at −20° C. Then, 100 μL was cultured again on selected media and incubated at 37° C. from 5 days up to 5 weeks. Collected bacteria may be heat killed at 95° C. for 30 minutes (e.g. before leaving the BSL3 containment area) prior to mass spectrometry.

Clinical Isolates

Thirty-two anonymized *M. abscessus* complex clinical isolates were (originally) collected from the lung of UK cystic fibrosis (CF) patients (recovered from sputum samples), and were grown from frozen stocks in 7H9 liquid media with OADC in 37° C. for 2 weeks before testing on MALDI-ToF MS. Previously those isolates were rpoB sequenced and the data indicated 3 clusters corresponded to three *M. abscessus* subspecies: *abscessus sensu stricto, bolletii*, and *massiliense*.

Sample Preparation

Three variables were selected for initial evaluation of NTM strains via MALDI-ToF MS.

(i) Phase of culture growth (ii) Growth media. Three media were used for mycobacterial growth Middlebrook 7H9 (Sigma Aldrich) with OADC—liquid medium Middlebrook 7H11 (Sigma Aldrich) with OADC—solid medium Kirchner (Sigma Aldrich)—liquid medium (iii) Matrix solution (composition): 10 mg/ml of 2,5-dihydroxybenzoic acid (DHB) diluted in four types of solvents to check the best performance:

A—in chloroform:methanol (95:5) (C/M)

B—in 50% Ethanol (EtOH)

C—in 25% Ethanol (EtOH)

D—in 50% Methanol (MeOH)

Additional concentrations of EtOH were also analysed, as per FIG. 35 and Example 6.

About 0.5 ml-1 mL of liquid mycobacterial biomass from the bottom of the tube was pipetted to the 1 mL Eppendorf and heated in water bath at 95° C. for 30 min in containment level 3 laboratory. The samples then were transported into a containment level 2 laboratory where all further work was performed. The liquid mycobacterial biomass was centrifuged at 15,000×g for 5 min and the supernatant was discarded. The bacterial pellet was washed 4 times with 200 μL of ultra-purified water. After each washing the pellet was centrifuged and the supernatant was removed. After the last washing around 50 μL of mycobacterial biomass was left, to be used for mass spectrometry analysis (and the remaining culture was frozen at −20° C. till the further testing).

Next, 0.4 μL of sample (resuspended bacteria) was pipetted onto the MALDI-ToF target slide and mixed with 0.6 μL of matrix solution (DHB in organic solvent, as described above).

The mixtures were dried at room temperature. Samples were analyzed on 4800 MALDI TOF/TOF™ Analyzer.

An exemplary way to carry out the invention is as follows:

Step 1: mycobacteria were isolated and grown on Middlebrook 7H9 liquid medium (without glycerol) and supplemented with 10% OADC (without any detergent). The culture was incubated (with shaking as appropriate) for 2-6 weeks at 37° C. One hundred microliters (e.g. having $10^4$ to $10^7$ bacteria) of bacteria are collected and transferred into an Eppendorf tube (0.5 to 2 mL) containing 100 microliter of water (distilled or double-distilled);

Step 2: Bacteria are then heat inactivated (facultative step) using a dry bath or water bath for 30 min at 95° C.;

Step 3: bacteria were pelleted and washed at least once with 100 μl to 1,000 μl double-distilled water to remove salts excess resulting from the culture medium (this optimises removal of background peaks in the mass spectrum output);

Step 4: the washed bacteria are suspended in 50 μl of double-distilled water and 0.4 μl is loaded on the MALDI-TOF target (SmallAnchor MALDI target plate, Bruker).

Step 5: Overlay the 0.4 μl of bacterial suspension with 0.6 μl of the designed matrix solution (DHB in organic solvent, as described above). Here, matrix 2,5-dihydroxybenzoic acid (DHB) suspended in organic solvents (usually Ethanol 25%), with mass spectrometry analysis conduced in the positive ion mode (or negative ion mode).

Step 5: MALDI-TOF MS acquisition (positive or negative ion mode). Classical MALDI-TOF MS machines that are present in clinical microbiology labs are suitable (Bioyper from Bruker Daltonics and VITEK-MS from bioMerieux). The former (Bioyper) was employed here. Samples were analyzed in the positive and negative ion mode operating at 20 kV and were set to acquire mass spectral peaks with mass/charge ratio (m/z) from 400 to 4,000 mass units. Mass spectrometry data were analyzed using Data Explorer® Software version 4.9 from Applied Biosystems and assignment of MTB/NTM was performed blinded, after visual interpretation of spectra following criteria previously published Step 6: From the obtained mass spectrum output having peaks corresponding to species-specific lipids, the inventors were able to discriminate Mtb complex, Non-Tuberculous mycobacteria.

Reproducibility

To check the technical reproducibility and the robustness of the instrument three samples were prepared from a single culture of ten ECDC strains. Additionally the thirty-two *M. abscessus* clinical isolates were tested blindly in duplicates/triplicates to confirm the results.

Organic Solvents Suitable for Use in a Matrix Solution

Examples of suitable solvents for matrix include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethanol, ethyl acetate, ethylene glycol, glycerine, heptane, Hexamethylphosphoramide (HMPA), Hexamethylphosphorous triamide (HMPT), hexane, methanol, methyl t-butyl ether (MTBE), methylene chloride, N-methyl pyrrolidinone (NMP), pentane, Petroleum ether (ligroine), 1-propanol, 2-propanol, pyridine, tetrahydrofuran (THF), toluene, triethyl amine, water, water heavy ($D_2O$), o-xylene, m-xylene, and p-xylene.

Example 1

Detection of Mycobacterial Lipid on Intact Bacteria

Samples of reference strains of mycobacteria were prepared as detailed above and subjected to mass spectrometry analysis (MALDI-TOF). Peaks corresponding to a number of mycobacterial membrane lipids (e.g. C-mycosides and phosphatidyl-myo-inositols) were readily detectable in the expected range of m/z.

These results demonstrate the applicability of the methods of the invention in detecting an intact mycobacteria in a sample (e.g. a crude sample).

Detection of mycobacteria by methods of the invention was possible for both bacteria in the stationary phase of growth and the logarithmic phase of growth (although a better mass spectral signal was achieved for stationary bacteria). Our samples were kept in incubator till the relevant growth was reached.

Furthermore, any differences in the mass spectrum output based on the tested media, Middlebrook 7H11, Middlebrook 7H9, and Kirchner, were very minor. However, among media used the best quality of biomass was generated by Middlebrook 7H11 agar. For practical purposes, it is useful to note that Middlebrook 7H9 medium works well, because this is the same medium employed in commercial MGIT tubes (*Mycobacterium* growth indicator tube) (Becton-Dickinson Microbiology Systems, Cockeysville, MD) used in diagnostics laboratories for drug susceptibility testing of Mycobacteria species.

Example 2

Detection of Specific Species of Mycobacteria Via Species-Specific Membrane Lipid Fingerprints The inventors selected a panel of 29 strains of NTMs comprising 22 commonly isolated species (Table 1). They were grown on different media (see above) and tested on DHB matrix diluted with four different solvents (A, B, C, and D). This collection of isolates included 7 RGM and 15 SGM species (Table 1).

First, the 10 ECDC reference strains was grown on Middlebrook 7H9 media with OADC and three samples were prepared from a single culture to check the lipid signature and reproducibility. The isolates were tested on MALDI-TOF MS with matrixes (DHB) solubilized in solvent A, or B. The reproducibility was high with both solvents. We also noticed that the same quality or better of mass spectra was generated with matrix diluted in the solvent B (50% EtOH) (better than A (C/M 95:5)).

We further compared another two solvents, C (25% EtOH) and D (50% MeOH). All results were comparable but the best quality was obtained from samples admixed with DHB matrix diluted in solvent B and C and analyzed on MALDI-ToF in positive ion mode.

Surprisingly, not only is it possible to distinguish between *M. tuberculosis* and NTMs, it is also possible to detect and discriminate between individual species based on the lipid fingerprints detectable on intact bacteria. Indeed, every strain tested was associated with a readily detectable, unique lipid fingerprint. Thus, the invention makes it possible to detect specific species, such as those associated with disease or with antibiotic resistance, from a crude sample of intact bacteria without any need for lengthy and expensive lipid extraction/purification. Given the unique compatibility of the methods with clinical laboratories, the invention will have a large impact on healthcare and the assessment of clinical infections.

Example 3

Detection of the Presence of a *Mycobacterium* Infection in Lung Transplant Candidate The 32 clinical isolates (of *M. abscessus* complex) obtained from the lung of cystic fibrosis (e.g. via recovery from sputum) were pipetted on the MALDI-ToF target slide (*M. abscessus,* 24; *M. bolletii,* 3; *M. massiliense,* 5). The analysis generated a strong signal with DHB matrix diluted in solvent A (Chloroform/Ethanol 95:5), B (50% Ethanol), and C (25% EtOH) (the latter is exemplified in the Figures)).

We repeated the test on the same number of frozen pellets again to test the technical reproducibility. There was 100% match to the previous results.

All *M. abscessus* complex isolates in this study were correctly identified to the species level.

The positive ion mass spectrum with DHB matrix diluted in solvent A, B and C is dominated by two sets of peaks. The first set of peaks from 1199.7 m/z to 1313.7 m/z with the most intense peaks at 1257.7, 1271.7, and 1285.7 m/z. And another set of peaks from 1389.7 m/z to 1459.8 m/z with the most intense peaks vary at 1389.7, 1403.8, 1431.8 m/z.

Example 4

Detection of the Presence of *Mycobacterium* Associated with Complications During Heart Surgery Detection of a number of *Mycobacterium* infections following cardiothoracic surgery has recently become a high priority (e.g. for Public Health England). Indeed, extra measures are generally put in place prior to open heart surgery to prevent infection with mycobacteria, in particular *Mycobacterium* chimaera (part of the *M. avium* complex).

*M. avium* complex (MAC) comprises mainly three very closely related species, *M. avium, M. intracellulare,* and *M. chimaera.* Existing diagnostic methods attempt to distinguish between *M. avium* and *M. intracellulare,* however *M. chimaera* is very difficult to differentiate from *M. intracellulare.* Visual analysis of the MALDI-TOF mass spectra of the MAC reference strains showed characteristic peaks for all of the species. In addition, a set of peaks present in *M. intracellulare* from 1443 m/z to 1569 m/z with the most intense peaks at 1471 m/z, 1499 m/z and 1513 m/z were absent in both strains of *M. chimaera* isolates—thus, the present invention advantageously allows for specific detection (e.g. distinction) of MAC species.

Both *M. chimaera* strains shared a lipid fingerprint based on a range of peaks between about 1200 m/z and 1400 m/z. Surprisingly, it was further possible to discriminate between strains of *M. chimaera.* The *M. chimaera* 20215-01546 has additional set of peaks at 2040-2068-2096 m/z and the *M. chimaera* 130444 at 1546-1560-1588-1602-1616 m/z. These peaks advantageously allow further differentiation from *M. intracellulare.*

Example 5

Detection of *Mycobacterium* Infection in Candidate for a Lung Transplant

The ability to detect mycobacteria infection in lung transplant candidates is of vital importance, as any existing infection can spread to and colonise the transplanted lung, significantly increasing the chance of organ rejection. In particular, an infection with *M. abscessus* is compromises selection for a lung transplant (i.e. such infection is considered to be a contraindication for a lung transplant).

A candidate for a lung transplant, suffering from Cystic Fibrosis, was investigated for the presence of a lung infection with *Mycobacterium* (as per Example 3). The present invention allowed for rapid detection of a NTM in the patient, and indeed the lipid fingerprint detected was indicative of the presence of an *M. abscessus.* The subject was therefore marked as an unsuitable candidate for a lung transplant, and the lung could be allocated to be given to a different candidate (shown to lack a mycobacterial infection by the method of the invention) who would be at a much lower risk of rejecting the transplant.

Furthermore, the inventors have demonstrated that the following positive ion mode peaks are specific to *M. abscessus* subsp. *massiliense* 1072-1075 m/z (e.g. about 1073.6 m/z), 1248-1251 m/z (preferably about 1249.9 m/z), 1260-1263 m/z (e.g. about 1261.9 m/z), 1262-1265 m/z (e.g. about 1263.9 m/z), 1274-1277 m/z (e.g. about 1275.9 m/z), 1276-

1279 m/z (e.g. about 1277.9 m/z), 1288-1291 m/z (e.g. about 1289.9 m/z), 1290-1293 m/z (e.g. about 1291.9 m/z), 1294-1297 m/z (e.g. about 1295.9 m/z), 1304-1307 m/z (e.g. about 1305.9 m/z), 1308-1311 m/z (e.g. about 1309.9 m/z), 1310-1313 m/z (e.g. about 1311.9 m/z), 1314-1317 m/z (e.g. about 1315.9 m/z), 1318-1321 m/z (e.g. about 1319.9 m/z), 1320-1323 m/z (e.g. about 1321.9 m/z), 1322-1325 m/z (e.g. about 1323.9 m/z), 1324-1327 m/z (e.g. about 1325.9 m/z), 1332-1335 m/z (e.g. about 1333.9 m/z), 1336-1339 m/z (e.g. about 1337.9 m/z), 1338-1341 m/z (e.g. about 1339.9 m/z), 1719-1722 m/z (e.g. about 1720.1 m/z), 1735-1738 m/z (e.g. about 1736.1 m/z), 1747-1750 m/z (e.g. about 1748.1 m/z), 1761-1764 m/z (e.g. about 1762.1 m/z), 1764-1767 m/z (e.g. about 1765.1 m/z), and 1789-1792 m/z (e.g. about 1790.1 m/z). Thus, detecting the absence one or more of said peaks indicates that the patient is infected with a subspecies (e.g. *M. abscessus* subsp. *abscessus* or *M. abscessus* subsp. *bolletii*) that is less susceptible (or resistant) to key antibiotics such as clarithromycin.

The first candidate was subsequently given a dose (e.g. prolonged course) of antibiotics, and removal of the infection was monitored by the methods of the invention.

Example 6

Demonstrating Utility of Matrix Solution

Colonies of *M. abscessus* were picked from solid agar medium (e.g. McFarland 20, 30 or 40) and subjected to mass spectrometry analysis according to a method of the invention (FIG. 35B); or a sterile loop was used to collect *M. abscessus* from a liquid culture (e.g. in McFarland 20, 30 or 40) and the collected liquid culture was subjected directly to mass spectrometry. Matrix solution comprising super-DHB matrix solubilised in different % of organic solvent (more particularly, EtOH) was employed. The different % values (of organic solvent) were 10%, 25%, 50%, 70%, 100% (v/v). The signal-to-noise ratio of the defined peaks on the resulting mass spectrum output was analysed. Surprisingly, it was found that an organic solvent concentration of <50% (v/v) provided improved signal-to-noise ratios (see FIG. 35). A concentration in the region of 25% was demonstrated to be particularly advantageous.

All publications mentioned in the above specification are herein incorporated by reference.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for detecting the presence or absence of a *Mycobacterium* in a sample, the method comprising:
   a. admixing a sample with a matrix solution comprising a super 2,5-dihydroxybenzoic acid matrix suspended in ethanol to provide an admixture, subjecting the admixture to mass spectrometry analysis in the positive ion mode and generating a mass spectrum output; and
   b. detecting one or more peak set in said mass spectrum output;

wherein said one or more peak set is selected from:
   i. a second peak set comprising at least two defined peaks selected from: a peak having a mass-to-charge ratio (m/z) of from 1220-1223 m/z, a peak having a m/z of from 1459-1462 m/z, a peak having a m/z of from 1739-1742 m/z, and a peak having a m/z of from 1741-1744 m/z;
   ii. a first peak set comprising at least two defined peaks selected from: a peak having a m/z of from 1256-1259 m/z, a peak having a m/z of from 1284-1287 m/z, a peak having a m/z of from 1402-1405 m/z, and a peak having a m/z of from 1430-1433 m/z;
   iii. a third peak set comprising at least two defined peaks selected from: a peak having a m/z of from 1242-1245 m/z, a peak having a m/z of from 1280-1283 m/z, a peak having a m/z of from 1294-1297 m/z, and a peak having a m/z of from 1923-1926 m/z;
   iv. a fourth peak set comprising at least two defined peaks selected from: a peak having a m/z of from 1012-1015 m/z, a peak having a m/z of from 1121-1124 m/z, a peak having a m/z of from 1122-1125 m/z, a peak having an m/z of from 1123-1126 m/z, and a peak having a m/z of from 1149-1152 m/z, and one or more further defined peak having a m/z of from 1021-1024 m/z, 1131-1134 m/z, 1134-1137 m/z, 1147-1150 m/z, 1150-1153 m/z, 1198-1201 m/z, 1878-1881 m/z, 1880-1883 m/z, 2131-2134 m/z, 2275-2278 m/z, 2553-2556 m/z, or a combination thereof;
   v. a fifth peak set comprising at least two defined peaks selected from: a peak having a m/z of from 1311-1314 m/z, a peak having a m/z of from 1339-1342 m/z, a peak having a m/z of from 1474-1477 m/z, a peak having a m/z of from 1488-1491 m/z, and a peak having a m/z of from 1823-1826 m/z;
   vi. a sixth peak set comprising at least two defined peaks selected from: a peak having a m/z of from 1242-1245 m/z, a peak having a m/z of from 1256-1259 m/z, a peak having a m/z of from 1270-1273 m/z, a peak having a m/z of from 1318-1321 m/z, and a peak having a m/z of from 1346-1349 m/z;
   vii. a seventh peak set comprising at least two defined peaks selected from: a peak having a m/z of from 1294-1297 m/z, a peak having a m/z of from 1296-1299 m/z, a peak having a m/z of from 1308-1311 m/z, and a peak having a m/z of from 1322-1325 m/z;
   viii. an eighth peak set comprising at least two defined peaks selected from: a peak having a m/z of from 1370-1373 m/z, and a peak having a m/z of from 1412-1415 m/z;
   ix. a ninth peak set comprising at least two defined peaks selected from: a peak having a m/z of from 2129-2132 m/z, a peak having a m/z of from 2171-2174 m/z, a peak having a m/z of from 2247-2250 m/z, and a peak having a m/z of from 2261-2264 m/z;
   x. a tenth peak set comprising at least two defined peaks selected from: a peak having a m/z of from 2273-2276 m/z, a peak having a m/z of from 2275-2278 m/z, a peak having a m/z of from 2551-2554 m/z, and a peak having a m/z of from 2553-2556 m/z;
   xi. an eleventh peak set comprising at least two defined peaks selected from: a peak having a m/z of from 1339-1342 m/z, a peak having a m/z of from 1353-

1356 m/z, a peak having a m/z of from 1367-1370 m/z, and a peak having an m/z of from 1381-1384 m/z;

xii. a twelfth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1298-1301 m/z, and one or more further defined peak having a m/z of from 1228-1231 m/z, 1252-1255 m/z, 1254-1257 m/z, 1258-1261 m/z, 1268-1271 m/z, 1280-1283 m/z, 1282-1285 m/z, 1284-1287 m/z, 1286-1289 m/z, 1288-1291 m/z, 1294-1297 m/z, 1296-1299 m/z, 1308-1311 m/z, 1310-1313 m/z, 1314-1317 m/z, 1322-1325 m/z, 1324-1327 m/z, 1336-1339 m/z, or a combination thereof;

xiii. a thirteenth peak set comprising at least two defined peaks selected from: a peak having an m/z of from 1458-1461 m/z, a peak having an m/z of from 2718-2721 m/z, a peak having an m/z of from 2760-2763 m/z, and a peak having an m/z of from 2788-2791 m/z;

xiv. a fourteenth peak set comprising at least two, three, four, or five defined peaks selected from: a peak having an m/z of from 1172-1175 m/z, a peak having an m/z of from 1174-1177 m/z, a peak having an m/z of from 1883-1886 m/z, a peak having an m/z of from 1909-1912 m/z, and a peak having an m/z of from 1911-1914 m/z;

xv. a fifteenth peak set comprising at least two defined peaks selected from: a peak having an m/z of from 1202-1205 m/z, a peak having an m/z of from 1224-1227 m/z, a peak having an m/z of from 1226-1229 m/z, and a peak having an m/z of from 1240-1243 m/z;

xvi. a sixteenth peak set comprising at least two defined peaks selected from: a peak having an m/z of from 1318-1321 m/z, a peak having an m/z of from 1332-1335 m/z, a peak having an m/z of from 1346-1349 m/z, a peak having an m/z of from 1360-1363 m/z, and a peak having an m/z of from 1374-1377 m/z;

xvii. a seventeenth peak set comprising at least two defined peaks selected from: a peak having an m/z of from 1308-1311 m/z, a peak having an m/z of from 1310-1313 m/z, a peak having an m/z of from 1324-1327 m/z, and a peak having an m/z of from 1338-1341 m/z;

xviii. an eighteenth peak set comprising at least two defined peaks selected from: a peak having an m/z of from 1012-1015 m/z, a peak having an m/z of from 1028-1031 m/z, a peak having an m/z of from 1697-1700 m/z, and a peak having an m/z of from 1698-1701 m/z;

xix. a nineteenth peak set comprising at least two defined peaks selected from: a peak having an m/z of from 1226-1229 m/z, and a peak having an m/z of from 1240-1243 m/z;

xx. a twentieth peak set comprising at least two defined peaks selected from: a peak having an m/z of from 1414-1417 m/z, a peak having an m/z of from 1443-1446 m/z, a peak having an m/z of from 1445-1448 m/z, a peak having an m/z of from 1515-1518 m/z, and a peak having an m/z of from 1543-1546 m/z;

xxi. a twenty-first peak set comprising at least two defined peaks selected from: a peak having an m/z of from 1036-1039 m/z, a peak having an m/z of from 1259-1262 m/z, a peak having an m/z of from 1374-1377 m/z, a peak having an m/z of from 2497-2500 m/z, and a peak having an m/z of from 2835-2838 m/z;

xxii. a twenty-second peak set comprising at least two defined peaks selected from: a peak having an m/z of from 1057-1060 m/z, a peak having an m/z of from 1498-1501 m/z, a peak having an m/z of from 1512-1515 m/z, and a peak having an m/z of from 1526-1529 m/z;

xxiii. a twenty-third peak set comprising at least two defined peaks selected from: a peak having an m/z of from 1432-1435 m/z, a peak having an m/z of from 1446-1449 m/z, a peak having an m/z of from 1460-1463 m/z, and a peak having an m/z of from 1474-1477 m/z;

xxiv. a twenty-fourth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1284-1287 m/z; and xxv. a twenty-fifth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1284-1287 m/z; and wherein the presence of said one or more peak set is indicative of the presence of a *Mycobacterium*; and wherein the absence of said one or more peak set is indicative of the absence of a *Mycobacterium*.

2. The method according to claim 1, wherein:

a. said second peak set comprises one or more further defined peak having a m/z of from 1025-1028 m/z, 1053-1056 m/z, 1081-1084 m/z, 1109-1112 m/z, 1178-1181 m/z, 1187-1190 m/z, 1206-1209 m/z, 1234-1237 m/z, 1236-1239 m/z, 1248-1251 m/z, 1259-1262 m/z, 1275-1278 m/z, 1287-1290 m/z, 1288-1291 m/z, 1301-1304 m/z, 1302-1305 m/z, 1303-1306 m/z, 1304-1307 m/z, 1445-1448 m/z, 1473-1476 m/z, 1475-1478 m/z, 1480-1483 m/z, 1487-1490 m/z, 1501-1504 m/z, 1517-1520 m/z, 1697-1700 m/z, 1699-1702 m/z, 1711-1714 m/z, 1713-1716 m/z, 1725-1728 m/z, 1753-1756 m/z, 1754-1757 m/z, 1755-1758 m/z, 1756-1759 m/z, 1767-1770 m/z, 2107-2110 m/z, or a combination thereof;

b. said first peak set comprises one or more further peak having a m/z of from 1198-1201 m/z, 1200-1203 m/z, 1214-1217 m/z, 1224-1227 m/z, 1226-1229 m/z, 1228-1231 m/z, 1240-1243 m/z, 1252-1255 m/z, 1254-1257 m/z, 1268-1271 m/z, 1270-1273 m/z, 1282-1285 m/z, 1298-1301 m/z, 1342-1345 m/z, 1356-1359 m/z, 1372-1375 m/z, 1374-1377 m/z, 1386-1389 m/z, 1388-1391 m/z, 1415-1418 m/z, 1429-1432 m/z, or a combination thereof;

c. said third peak set comprises one or more further peak having a m/z of from 1030-1033 m/z, 1210-1213 m/z, 1214-1217 m/z, 1218-1221 m/z, 1224-1227 m/z, 1225-1228 m/z, 1226-1229 m/z, 1228-1231 m/z, 1232-1235 m/z, 1234-1237 m/z, 1236-1239 m/z, 1238-1241 m/z, 1240-1243 m/z, 1245-1248 m/z, 1246-1249 m/z, 1248-1251 m/z, 1250-1253 m/z, 1252-1255 m/z, 1254-1257 m/z, 1256-1259 m/z, 1258-1261 m/z, 1260-1263 m/z, 1262-1265 m/z, 1263-1266 m/z, 1264-1267 m/z, 1266-1269 m/z, 1268-1271 m/z, 1270-1273 m/z, 1272-1275 m/z, 1273-1276 m/z, 1274-1277 m/z, 1282-1285 m/z, 1284-1287 m/z, 1285-1288 m/z, 1286-1289 m/z, 1296-1299 m/z, 1298-1301 m/z, 1308-1311 m/z, 1310-1313 m/z, 1312-1315 m/z, 1322-1325 m/z, 1324-1327 m/z, 1338-1341 m/z, 1368-1371 m/z, 1370-1373 m/z, 1384-1387 m/z, 1897-1900 m/z, 1909-1912 m/z, 1937-1940 m/z, 1939-1942 m/z, 1951-1954 m/z, 1954-1957 m/z, 1965-1968 m/z, 1967-1970 m/z, or a combination thereof;

d. said fifth peak set comprises one or more further defined peak having a m/z of from 1253-1256 m/z, 1267-1270 m/z, 1269-1272 m/z, 1279-1282 m/z, 1281-1284 m/z, 1283-1286 m/z, 1295-1298 m/z, 1297-1300 m/z, 1299-1302 m/z, 1300-1303 m/z, 1307-1310 m/z, 1309-1312 m/z, 1313-1316 m/z, 1323-1326 m/z, 1325-1328 m/z, 1327-1330 m/z, 1329-1332 m/z, 1341-1344 m/z, 1355-1358 m/z, 1357-1360 m/z, 1429-1432 m/z, 1432-1435 m/z, 1442-1445 m/z, 1443-1446 m/z, 1445-1448 m/z, 1446-1449 m/z, 1456-1459 m/z, 1457-1460 m/z, 1458-1461 m/z, 1460-1463 m/z, 1469-1472 m/z, 1471-1474 m/z, 1472-1475 m/z, 1477-1480 m/z, 1484-1487 m/z, 1485-1488 m/z, 1486-1489 m/z, 1497-1500 m/z, 1499-1502 m/z, 1500-1503 m/z, 1502-1505 m/z, 1513-1516 m/z, 1514-1517 m/z, 1516-1519 m/z, 1518-1521 m/z, 1528-1531 m/z, 1529-1532 m/z, 1530-1533 m/z, 1766-1769 m/z, 1781-1784 m/z, 1795-1798 m/z, 1809-1812 m/z, 1811-1814 m/z, 1815-1818 m/z, 1821-1824 m/z, 1829-1832 m/z, 1837-1840 m/z, 1839-1842 m/z, 1849-1852 m/z, 1851-1854 m/z, or a combination thereof;

e. said sixth peak set comprises one or more further peak having a m/z of from 1127-1130 m/z, 1140-1143 m/z, 1144-1147 m/z, 1158-1161 m/z, 1168-1171 m/z, 1169-1172 m/z, 1172-1175 m/z, 1184-1187 m/z, 1186-1189 m/z, 1198-1201 m/z, 1199-1202 m/z, 1200-1203 m/z, 1212-1215 m/z, 1214-1217 m/z, 1224-1227 m/z, 1226-1229 m/z, 1227-1230 m/z, 1228-1231 m/z, 1230-1233 m/z, 1240-1243 m/z, 1252-1255 m/z, 1254-1257 m/z, 1259-1262 m/z, 1268-1271 m/z, 1272-1275 m/z, 1282-1285 m/z, 1284-1287 m/z, 1286-1289 m/z, 1290-1293 m/z, 1296-1299 m/z, 1298-1301 m/z, 1300-1303 m/z, 1304-1307 m/z, 1310-1313 m/z, 1314-1317 m/z, 1316-1319 m/z, 1328-1331 m/z, 1330-1333 m/z, 1331-1334 m/z, 1332-1335 m/z, 1342-1345 m/z, 1344-1347 m/z, 1345-1348 m/z, 1356-1359 m/z, 1358-1361 m/z, 1360-1363 m/z, 1368-1371 m/z, 1370-1373 m/z, 1372-1375 m/z, 1374-1377 m/z, 1386-1389 m/z, 1388-1391 m/z, 1402-1405 m/z, 1414-1417 m/z, 1416-1419 m/z, 1428-1431 m/z, 1430-1433 m/z, 1519-1522 m/z, 1545-1548 m/z, 1547-1550 m/z, or a combination thereof;

f. said seventh peak set comprises one or more further defined peak having a m/z of from 1266-1269 m/z, 1268-1271 m/z, 1310-1313 m/z, 1324-1327 m/z, 1338-1341 m/z, or a combination thereof;

g. said ninth peak set comprises one or more further defined peak having a m/z of from 2115-2118 m/z, 2145-2148 m/z, 2157-2160 m/z, 2187-2190 m/z, 2188-2191 m/z, 2205-2208 m/z, 2219-2222 m/z, 2233-2236 m/z, 2245-2248 m/z, 2259-2262 m/z, 2277-2280 m/z, or a combination thereof;

h. said tenth peak set comprises one or more further defined peak having a m/z of from 1848-1851 m/z, 2215-2218 m/z, 2231-2234 m/z, 2233-2236 m/z, 2235-2238 m/z, 2243-2246 m/z, 2244-2247 m/z, 2245-2248 m/z, 2247-2250 m/z, 2257-2260 m/z, 2260-2263 m/z, 2261-2264 m/z, 2262-2265 m/z, 2271-2274 m/z, 2285-2288 m/z, 2287-2290 m/z, 2289-2292 m/z, 2291-2294 m/z, 2389-2392 m/z, 2511-2514 m/z, 2549-2552 m/z, 2569-2572 m/z, or a combination thereof;

i. said eleventh peak set comprises one or more further defined peak having a m/z of from 1311-1314 m/z, 1325-1328 m/z, 1369-1372 m/z, 1397-1400 m/z, or a combination thereof;

j. said thirteenth peak set comprises one or more further peak having a m/z of from 1220-1223 m/z, 1303-1306 m/z, 1317-1320 m/z, 1345-1348 m/z, 1442-1445 m/z, 1456-1459 m/z, 1474-1477 m/z, 1485-1488 m/z, 1487-1490 m/z, 1695-1698 m/z, 1697-1700 m/z, 1723-1726 m/z, 1725-1728 m/z, 1739-1742 m/z, 2107-2110 m/z, 2132-2135 m/z, 2133-2136 m/z, 2147-2150 m/z, 2161-2164 m/z, 2175-2178 m/z, 2300-2303 m/z, 2316-2319 m/z, 2454-2457 m/z, 2496-2499 m/z, 2524-2527 m/z, 2586-2589 m/z, 2628-2631 m/z, 2656-2659 m/z, 2732-2735 m/z, 2736-2739 m/z, 2746-2749 m/z, 2774-2777 m/z, 2777-2780 m/z, 2786-2789 m/z, 2802-2805 m/z, 2804-2807 m/z, 2850-2853 m/z, 2892-2895 m/z, 2920-2923 m/z, or a combination thereof;

k. said fourteenth peak set comprises one or more further peak having a m/z of from 1146-1149 m/z, 1160-1163 m/z, 1190-1193 m/z, 1196-1199 m/z, 1561-1564 m/z, 1881-1884 m/z, 1885-1888 m/z, 1897-1900 m/z, 1923-1926 m/z, 1925-1928 m/z, 1935-1938 m/z, 1937-1940 m/z, 1939-1942 m/z, 1951-1954 m/z, or a combination thereof;

l. said fifteenth peak set comprises one or more further defined peak having a m/z of from 1184-1187 m/z, 1243-1246 m/z, or a combination thereof;

m. said sixteenth peak set comprises one or more further peak having a m/z of from 1330-1333 m/z, 1344-1347 m/z, 1358-1361 m/z, 1372-1375 m/z, 1386-1389 m/z, 1388-1391 m/z, 1400-1403 m/z, 1402-1405 m/z, 1414-1417 m/z, or a combination thereof;

n. said seventeenth peak set comprises one or more further defined peak having a m/z of from 1294-1297 m/z, 1296-1299 m/z, or a combination thereof;

o. said eighteenth peak set comprises one or more further defined peak having a m/z of from 1723-1726 m/z, 1814-1817 m/z, or a combination thereof;

p. said nineteenth peak set comprises a further defined peak having a m/z of from 1238-1241 m/z;

q. said twentieth peak set comprises one or more further peak having a m/z of from 1039-1042 m/z, 1074-1077 m/z, 1124-1127 m/z, 1150-1153 m/z, 1184-1187 m/z, 1198-1201 m/z, 1212-1215 m/z, 1214-1217 m/z, 1220-1223 m/z, 1226-1229 m/z, 1228-1231 m/z, 1240-1243 m/z, 1242-1245 m/z, 1254-1257 m/z, 1256-1259 m/z, 1268-1271 m/z, 1270-1273 m/z, 1282-1285 m/z, 1284-1287 m/z, 1294-1297 m/z, 1296-1299 m/z, 1299-1302 m/z, 1310-1313 m/z, 1312-1315 m/z, 1313-1316 m/z, 1324-1327 m/z, 1330-1333 m/z, 1340-1343 m/z, 1354-1357 m/z, 1356-1359 m/z, 1357-1360 m/z, 1358-1361 m/z, 1368-1371 m/z, 1370-1373 m/z, 1372-1375 m/z, 1374-1377 m/z, 1382-1385 m/z, 1384-1387 m/z, 1386-1389 m/z, 1388-1391 m/z, 1398-1401 m/z, 1400-1403 m/z, 1417-1420 m/z, 1426-1429 m/z, 1429-1432 m/z, 1430-1433 m/z, 1440-1443 m/z, 1457-1460 m/z, 1459-1462 m/z, 1471-1474 m/z, 1473-1476 m/z, 1474-1477 m/z, 1487-1490 m/z, 1501-1504 m/z, 1529-1532 m/z, 1531-1534 m/z, 1541-1544 m/z, 1559-1562 m/z, 1571-1574 m/z, or a combination thereof;

r. said twenty-first peak set comprises one or more further defined peak having a m/z of from 1042-1045 m/z, 1052-1055 m/z, 1124-1127 m/z, 1150-1153 m/z, 1204-1207 m/z, 1220-1223 m/z, 1244-1247 m/z, 1273-1276 m/z, 1287-1290 m/z, 1296-1299 m/z, 1390-1393 m/z, 1392-1395 m/z, 1427-1430 m/z, 1430-1433 m/z, 1442-1445 m/z, 1444-1447 m/z, 1458-1461 m/z, 1474-1477 m/z, 1475-1478 m/z, 1488-1491 m/z, 1534-1537 m/z, 1680-1683 m/z, 1697-1700 m/z, 1698-1701 m/z, 1707-1710 m/z, 1722-1725 m/z, 1723-1726 m/z, 1779-1782 m/z, 1819-1822 m/z, 1821-1824 m/z, 1838-1841 m/z, 2091-2094 m/z, 2103-2106 m/z, 2107-2110 m/z, 2117-2120 m/z, 2118-2121 m/z, 2119-2122 m/z, 2145-2148 m/z, 2159-2162 m/z, 2175-2178 m/z, 2356-2359 m/z, 2373-2376 m/z, 2397-2400 m/z, 2439-2442 m/z, 2455-2458 m/z, 2483-2486 m/z, 2495-2498 m/z, 2512-2515 m/z, 2513-2516 m/z, 2777-2780 m/z, 2780-2783 m/z, 2793-2796 m/z, 2807-2810 m/z, 2809-2812 m/z, 2821-2824 m/z, 2822-2825 m/z, 2834-2837 m/z, 2849-2852 m/z, 2851-2854 m/z, or a combination thereof;

s. said twenty-second peak set comprises one or more further defined peak having a m/z of from 1043-1046 m/z, 1071-1074 m/z, 1073-1076 m/z, 1079-1082 m/z, 1468-1471 m/z, 1474-1477 m/z, 1476-1479 m/z, 1482-1485 m/z, 1484-1487 m/z, 1490-1493 m/z, 1496-1499 m/z, 1504-1507 m/z, 1510-1513 m/z, or a combination thereof;

t. said twenty-third peak set comprises one or more further peak having a m/z of from 1306-1309 m/z, 1404-1407 m/z, 1418-1421 m/z, 1420-1423 m/z, 1430-1433 m/z, 1444-1447 m/z, 1448-1451 m/z, 1458-1461 m/z, 1462-1465 m/z, 1472-1475 m/z, 1488-1491 m/z, 1490-1493 m/z, 1502-1505 m/z, 1511-1514 m/z, or a combination thereof;

u. said twenty-fourth peak set further comprises one or more peak having a m/z of from 1198-1201 m/z, 1312-1315 m/z, 1388-1391 m/z, 1402-1405 m/z, 1430-1433 m/z, 1458-1461 m/z, or a combination thereof; and/or v. said twenty-fifth peak set comprises one or more further defined peak having an m/z of from 1198-1201 m/z, 1224-1227 m/z, 1228-1231 m/z, 1242-1245 m/z, 1256-1259 m/z, 1252-1255 m/z, 1268-1271 m/z, 1270-1273 m/z, 1284-1287 m/z, 1374-1377-m/z, 1388-1391 m/z, 1402-1405 m/z, 1416-1419 m/z, 1430-1433 m/z, or a combination thereof.

3. A kit for use in a method for detecting the presence or absence of a *Mycobacterium*; the kit comprising:
a. super 2,5-dihydroxybenzoic acid;
b. ethanol; and
c. instructions to perform a method according to claim 1.

4. The method according to claim 1, wherein said sample is an isolated sample obtained from a subject that is a candidate for receiving a lung transplant, and:
wherein the presence of said one or more peak set indicates that the subject is not a suitable candidate for receiving a lung transplant; or
wherein the absence of said one or more peak set indicates that the subject is a suitable candidate for receiving a lung transplant.

5. The method according to claim 1, wherein said sample is obtained from operating theatre equipment, and:
wherein the presence of said one or more peak set indicates that the operating theatre equipment is not suitable to be used during cardiothoracic surgery of a subject; or
wherein the absence of said one or more peak set indicates that the operating theatre equipment is suitable to be used during cardiothoracic surgery of a subject.

6. The method according to claim 1, wherein said sample is an isolated sample obtained from a subject that has received cardiothoracic surgery, and:
wherein the presence of said one or more peak set is indicative of the presence of a bacterial infection in the subject subsequent to receiving cardiothoracic surgery; or
wherein the absence of said one or more peak set is indicative of the absence of a bacterial infection in a subject subsequent to receiving cardiothoracic surgery.

7. The method according to claim 1, wherein the sample is subjected to mass spectrometry in the positive ion mode, and confirming the presence or absence of one or more of the following defined peak(s) in the mass spectrum output: a peak having a m/z of from 1210-1213 m/z, 1326-1329 m/z, 1356-1359 m/z, 1370-1373 m/z, 1384-1387 m/z, 1398-1401 m/z, 1400-1403 m/z, 1412-1415 m/z, 1414-1417 m/z, 1426-1429 m/z, 1428-1431 m/z, 1442-1445 m/z, 1444-1447 m/z, 1456-1459 m/z, 1458-1461 m/z, and/or 1472-1475 m/z;
wherein the presence of said one or more peak confirms the presence of *M. abscessus* subsp. *abscessus* and wherein the absence of said one or more peak is indicative of the absence of *M. abscessus* subsp. *abscessus*; and/or
wherein said sample is an isolated sample obtained from a subject that is a candidate for receiving a lung transplant, wherein the presence of said one or more peak indicates that the subject is not a suitable candidate for receiving a lung transplant and wherein the absence of said one or more peak indicates that the subject is a suitable candidate for receiving a lung transplant; and/or
wherein said sample is obtained from operating theatre equipment, wherein the presence of said one or more peak indicates that the operating theatre equipment is not suitable to be used during cardiothoracic surgery of a subject and wherein the absence of said one or more peak indicates that the operating theatre equipment is suitable to be used during cardiothoracic surgery of a subject; and/or
wherein said sample is an isolated sample obtained from a subject that has received cardiothoracic surgery, wherein the presence of said one or more peak is indicative of the presence of a bacterial infection in the subject subsequent to receiving cardiothoracic surgery and wherein the absence of said one or more peak is indicative of the absence of a bacterial infection in the subject subsequent to receiving cardiothoracic surgery.

8. The method according to claim 1, wherein the sample is subjected to mass spectrometry in the negative ion mode, and the method further comprises confirming the presence or absence of one or more of the following defined peak(s) in the mass spectrum output: a peak having a m/z of from 681-684 m/z and/or 696-699 m/z;
wherein the presence of said one or more peak confirms the presence of *M. abscessus* subsp. *abscessus* and wherein the absence of said one or more peak is indicative of the absence of *M. abscessus* subsp. *abscessus*; and/or
wherein said sample is an isolated sample obtained from a subject that is a candidate for receiving a lung transplant, wherein the presence of said one or more peak indicates that the subject is not a suitable candidate for receiving a lung transplant and wherein the absence of said one or more peak indicates that the subject is a suitable candidate for receiving a lung transplant; and/or wherein said sample is obtained from operating theatre equipment, wherein the presence of said one or more peak indicates that the operating theatre equipment is not suitable to be used during cardiothoracic surgery of a subject and wherein the absence of said one or more peak indicates that the operating theatre equipment is suitable to be used during cardiothoracic surgery of a subject; and/or wherein said sample is an isolated sample obtained from a subject that has received cardiothoracic surgery, wherein the presence of said one or more peak is indicative of the presence of a bacterial infection in the subject subsequent to receiving cardiothoracic surgery and wherein the absence of said one or more peak is indicative of the absence of a bacterial infection in the subject subsequent to receiving cardiothoracic surgery.

9. The method according to claim 1, wherein the sample is subjected to mass spectrometry in the negative ion mode, and confirming the presence or absence of one or more of the following defined peak(s) in the mass spectrum output: a peak having a m/z of from 520-523 m/z, 534-537 m/z, 535-538 m/z, 1403-1406 m/z, 1565-1568 m/z, 1568-1571 m/z, 1578-1581 m/z, 1581-1584 m/z, 1621-1624 m/z, 1623-1626 m/z, 1637-1640 m/z, 1638-1641 m/z, 1647-1650 m/z, 1648-1651 m/z, 1649-1652 m/z, 1663-1666 m/z, 1664-1667 m/z, 2296-2299 m/z, and/or 2297-2300 m/z;

wherein the presence of said one or more peak confirms the presence of *M. abscessus* subsp. *bolletii* and wherein the absence of said one or more peak is indicative of the absence of *M. abscessus* subsp. *bolletii*; and/or wherein said sample is an isolated sample obtained from a subject that is a candidate for receiving a lung transplant, wherein the presence of said one or more peak indicates that the subject is not a suitable candidate for receiving a lung transplant and wherein the absence of said one or more peak indicates that the subject is a suitable candidate for receiving a lung transplant; and/or wherein said sample is obtained from operating theatre equipment, wherein the presence of said one or more peak indicates that the operating theatre equipment is not suitable to be used during cardiothoracic surgery of a subject and wherein the absence of said one or more peak indicates that the operating theatre equipment is suitable to be used during cardiothoracic surgery of a subject; and/or wherein said sample is an isolated sample obtained from a subject that has received cardiothoracic surgery, wherein the presence of said one or more peak is indicative of the presence of a bacterial infection in the subject subsequent to receiving cardiothoracic surgery and wherein the absence of said one or more peak is indicative of the absence of a bacterial infection in the subject subsequent to receiving cardiothoracic surgery.

10. The method according to claim 1, wherein the sample is subjected to mass spectrometry in the positive ion mode, and a method of the invention may further comprise confirming the absence of one or more of the following defined peak(s) in the mass spectrum output: a peak having a m/z of from 1072-1075 m/z, 1248-1251 m/z, 1260-1263 m/z, 1262-1265 m/z, 1274-1277 m/z, 1276-1279 m/z, 1288-1291 m/z, 1290-1293 m/z, 1294-1297 m/z, 1304-1307 m/z, 1308-1311 m/z, 1310-1313 m/z, 1314-1317 m/z, 1318-1321 m/z, 1320-1323 m/z, 1322-1325 m/z, 1324-1327 m/z, 1332-1335 m/z, 1336-1339 m/z, 1338-1341 m/z, 1719-1722 m/z, 1735-1738 m/z, 1747-1750 m/z, 1761-1764 m/z, 1764-1767 m/z, and/or 1789-1792 m/z;

wherein the presence of said one or more peak confirms the presence of *M. abscessus* subsp. *massiliense* and wherein the absence of said one or more peak confirms the absence of *M. abscessus* subsp. *massiliense*; and/or wherein said sample is an isolated sample obtained from a subject that is a candidate for receiving a lung transplant, wherein the absence of said one or more peak indicates that the subject is a suitable candidate for receiving a lung transplant and wherein the absence of said one or more peak indicates that the subject is a suitable candidate for receiving a lung transplant; and/or wherein said sample is obtained from operating theatre equipment, wherein the absence of said one or more peak indicates that the operating theatre equipment is suitable to be used during cardiothoracic surgery of a subject and wherein the absence of said one or more peak indicates that the operating theatre equipment is suitable to be used during cardiothoracic surgery of a subject; and/or wherein said sample is an isolated sample obtained from a subject that has received cardiothoracic surgery, wherein the absence of said one or more peak is indicative of the absence of a *M. abscessus* subsp. *massiliense* infection in the subject subsequent to receiving cardiothoracic surgery and wherein the absence of said one or more peak is indicative of the absence of a bacterial infection in the subject subsequent to receiving cardiothoracic surgery.

11. The method according to claim 1, wherein the sample is subjected to mass spectrometry in the negative ion mode, and method of the invention may further comprise confirming the absence of one or more of the following defined peak(s) in the mass spectrum output: a peak having a m/z of from 408-411 m/z, 490-493 m/z, and/or 512-515 m/z;

wherein the presence of said one or more peak confirms the absence of *M. abscessus* subsp. *massiliense* and wherein the absence of said one or more peak confirms the absence of *M. abscessus* subsp. *massiliense*; and/or wherein said sample is an isolated sample obtained from a subject that is a candidate for receiving a lung transplant, wherein the absence of said one or more peak indicates that the subject is a suitable candidate for receiving a lung transplant and wherein the absence of said one or more peak indicates that the subject is a suitable candidate for receiving a lung transplant; and/or wherein the absence of said one or more peak indicates that the operating theatre equipment is suitable to be used during cardiothoracic surgery of a subject and wherein the absence of said one or more peak indicates that the operating theatre equipment is suitable to be used during cardiothoracic surgery of a subject; and/or wherein said sample is an isolated sample obtained from a subject that has received cardiothoracic surgery, wherein the absence of said one or more peak is indicative of the absence of a *M. abscessus* subsp. *massiliense* infection in the subject subsequent to receiving cardiothoracic surgery and wherein the absence of said one or more peak is indicative of the absence of a bacterial infection in the subject subsequent to receiving cardiothoracic surgery.

12. The method according to claim 1, wherein said matrix solution comprises <50% v/v ethanol.

13. The method according to claim 1, wherein said matrix solution comprises 20-30% v/v ethanol.

14. A method of assaying a sample by mass spectrometry, the method comprising:

a. providing a sample comprising, or suspected of com- prising, a *Mycobacterium;* b. admixing the sample with a matrix solution comprising a super 2,5-dihydroxybenzoic acid matrix suspended in ethanol to provide an admixture, subjecting the admixture to mass spectrometry analysis in the positive ion mode and generating a mass spectrum output; and c. detecting the presence or absence of one or more peak set in said mass spectrum output;

wherein said one or more peak set is selected from:

i. a second peak set comprising at least two defined peaks selected from: a peak having a mass-to-charge ratio (m/z) of from 1220-1223 m/z, a peak having a m/z of from 1459-1462 m/z, a peak having a m/z of from 1739-1742 m/z, and a peak having a m/z of from 1741-1744 m/z;

ii. a first peak set comprising at least two defined peaks selected from: a peak having a m/z of from 1256-1259 m/z, a peak having a m/z of from 1284-1287 m/z, a peak having a m/z of from 1402-1405 m/z, and a peak having a m/z of from 1430-1433 m/z;

iii. a third peak set comprising at least two defined peaks selected from: a peak having a m/z of from 1242-1245 m/z, a peak having a m/z of from 1280-1283 m/z, a peak having a m/z of from 1294-1297 m/z, and a peak having a m/z of from 1923-1926 m/z;

iv. a fourth peak set comprising at least two defined peaks selected from: a peak having a m/z of from 1012-1015 m/z, a peak having a m/z of from 1121-1124 m/z, a peak having a m/z of from 1122-1125 m/z, a peak having an m/z of from 1123-1126 m/z, and a peak having a m/z of from 1149-1152 m/z, and one or more further defined peak having a m/z of from 1021-1024 m/z, 1131-1134 m/z, 1134-1137 m/z, 1147-1150 m/z, 1150-1153 m/z, 1198-1201 m/z, 1878-1881 m/z, 1880-1883 m/z, 2131-2134 m/z, 2275-2278 m/z, 2553-2556 m/z, or a combination thereof;

v. a fifth peak set comprising at least two defined peaks selected from: a peak having a m/z of from 1311-1314 m/z, a peak having a m/z of from 1339-1342 m/z, a peak having a m/z of from 1474-1477 m/z, a peak having a m/z of from 1488-1491 m/z, and a peak having a m/z of from 1823-1826 m/z;

vi. a sixth peak set comprising at least two defined peaks selected from: a peak having a m/z of from 1242-1245 m/z, a peak having a m/z of from 1256-1259 m/z, a peak having a m/z of from 1270-1273 m/z, a peak having a m/z of from 1318-1321 m/z, and a peak having a m/z of from 1346-1349 m/z;

vii. a seventh peak set comprising at least two defined peaks selected from: a peak having a m/z of from 1294-1297 m/z, a peak having a m/z of from 1296-1299 m/z, a peak having a m/z of from 1308-1311 m/z, and a peak having a m/z of from 1322-1325 m/z;

viii. an eighth peak set comprising at least two defined peaks selected from: a peak having a m/z of from 1370-1373 m/z, and a peak having a m/z of from 1412-1415 m/z;

ix. a ninth peak set comprising at least two defined peaks selected from: a peak having a m/z of from 2129-2132 m/z, a peak having a m/z of from 2171-2174 m/z, a peak having a m/z of from 2247-2250 m/z, and a peak having a m/z of from 2261-2264 m/z;

x. a tenth peak set comprising at least two defined peaks selected from: a peak having a m/z of from 2273-2276 m/z, a peak having a m/z of from 2275-2278 m/z, a peak having a m/z of from 2551-2554 m/z, and a peak having a m/z of from 2553-2556 m/z;

xi. an eleventh peak set comprising at least two defined peaks selected from: a peak having a m/z of from 1339-1342 m/z, a peak having a m/z of from 1353-1356 m/z, a peak having a m/z of from 1367-1370 m/z, and a peak having an m/z of from 1381-1384 m/z;

xii a twelfth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1298-1301 m/z, and one or more further defined peak having a m/z of from 1228-1231 m/z, 1252-1255 m/z, 1254-1257 m/z, 1258-1261 m/z, 1268-1271 m/z, 1280-1283 m/z, 1282-1285 m/z, 1284-1287 m/z, 1286-1289 m/z, 1288-1291 m/z, 1294-1297 m/z, 1296-1299 m/z, 1308-1311 m/z, 1310-1313 m/z, 1314-1317 m/z, 1322-1325 m/z, 1324-1327 m/z, 1336-1339 m/z, or a combination thereof;

xiii. a thirteenth peak set comprising at least two defined peaks selected from: a peak having an m/z of from 1458-1461 m/z, a peak having an m/z of from 2718-2721 m/z, a peak having an m/z of from 2760-2763 m/z, and a peak having an m/z of from 2788-2791 m/z;

xiv. a fourteenth peak set comprising at least two, three, four, or five defined peaks selected from: a peak having an m/z of from 1172-1175 m/z, a peak having an m/z of from 1174-1177 m/z, a peak having an m/z of from 1883-1886 m/z, a peak having an m/z of from 1909-1912 m/z, and a peak having an m/z of from 1911-1914 m/z;

xv. a fifteenth peak set comprising at least two defined peaks selected from: a peak having an m/z of from 1202-1205 m/z, a peak having an m/z of from 1224-1227 m/z, a peak having an m/z of from 1226-1229 m/z, and a peak having an m/z of from 1240-1243 m/z;

xvi. a sixteenth peak set comprising at least two defined peaks selected from: a peak having an m/z of from 1318-1321 m/z, a peak having an m/z of from 1332-1335 m/z, a peak having an m/z of from 1346-1349 m/z, a peak having an m/z of from 1360-1363 m/z, and a peak having an m/z of from 1374-1377 m/z;

xvii. a seventeenth peak set comprising at least two defined peaks selected from: a peak having an m/z of from 1308-1311 m/z, a peak having an m/z of from 1310-1313 m/z, a peak having an m/z of from 1324-1327 m/z, and a peak having an m/z of from 1338-1341 m/z;

xviii. an eighteenth peak set comprising at least two defined peaks selected from: a peak having an m/z of from 1012-1015 m/z, a peak having an m/z of from 1028-1031 m/z, a peak having an m/z of from 1697-1700 m/z, and a peak having an m/z of from 1698-1701 m/z;

xix. a nineteenth peak set comprising at least two defined peaks selected from: a peak having an m/z of from 1226-1229 m/z, and a peak having an m/z of from 1240-1243 m/z;

xx. a twentieth peak set comprising at least two defined peaks selected from: a peak having an m/z of from 1414-1417 m/z, a peak having an m/z of from 1443-1446 m/z, a peak having an m/z of from 1445-1448 m/z, a peak having an m/z of from 1515-1518 m/z, and a peak having an m/z of from 1543-1546 m/z;

xxi. a twenty-first peak set comprising at least two defined peaks selected from: a peak having an m/z of from 1036-1039 m/z, a peak having an m/z of from 1259-1262 m/z, a peak having an m/z of from 1374-1377 m/z, a peak having an m/z of from 2497-2500 m/z, and a peak having an m/z of from 2835-2838 m/z;

xxii. a twenty-second peak set comprising at least two defined peaks selected from: a peak having an m/z of from 1057-1060 m/z, a peak having an m/z of from 1498-1501 m/z, a peak having an m/z of from 1512-1515 m/z, and a peak having an m/z of from 1526-1529 m/z;

xxiii. a twenty-third peak set comprising at least two defined peaks selected from: a peak having an m/z of from 1432-1435 m/z, a peak having an m/z of from 1446-1449 m/z, a peak having an m/z of from 1460-1463 m/z, and a peak having an m/z of from 1474-1477 m/z;

xxiv. a twenty-fourth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1284-1287 m/z; and xxv. a twenty-fifth peak set comprising at least two defined peaks selected from: a peak having an m/z of from 1242-1245 m/z, a peak having an m/z of from 1256-1259 m/z, a peak having an m/z of from 1270-1273 m/z, and a peak having an m/z of from 1284-1287 m/z.

15. The method according to claim 14, wherein said matrix solution comprises <50% v/v ethanol.

16. The method according to claim 14, wherein said matrix solution comprises 20-30% v/v ethanol.

\* \* \* \* \*